US012721892B2

(12) United States Patent
Dotti et al.

(10) Patent No.: US 12,721,892 B2
(45) Date of Patent: Sep. 1, 2026

(54) METHODS AND COMPOSITIONS FOR CHIMERIC ANTIGEN RECEPTOR TARGETING CANCER CELLS

(71) Applicant: The University of North Carolina at Chapel Hill, Chapel Hill, NC (US)

(72) Inventors: Gianpietro Dotti, Chapel Hill, NC (US); Chuang Sun, Hangzhou (CN); Peishun Shou, Cary, NC (US); Yang Xu, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 951 days.

(21) Appl. No.: 17/773,281

(22) PCT Filed: Oct. 30, 2020

(86) PCT No.: PCT/US2020/058083
§ 371 (c)(1),
(2) Date: Apr. 29, 2022

(87) PCT Pub. No.: WO2021/087183
PCT Pub. Date: May 6, 2021

(65) Prior Publication Data

US 2024/0156864 A1 May 16, 2024

Related U.S. Application Data

(60) Provisional application No. 62/928,675, filed on Oct. 31, 2019.

(51) Int. Cl.

| | |
|---|---|
| ***A61K 40/42*** | (2025.01) |
| ***A61K 40/11*** | (2025.01) |
| ***A61K 40/31*** | (2025.01) |
| ***A61P 35/00*** | (2006.01) |
| ***C07K 7/64*** | (2006.01) |
| ***C07K 16/28*** | (2006.01) |
| ***C12N 9/12*** | (2006.01) |
| *A61K 38/00* | (2006.01) |

(52) U.S. Cl.
CPC .......... *A61K 40/4202* (2025.01); *A61K 40/11* (2025.01); *A61K 40/31* (2025.01); *A61K 40/4211* (2025.01); *A61K 40/4258* (2025.01); *A61K 40/4261* (2025.01); *A61P 35/00* (2018.01); *C07K 7/64* (2013.01); *C07K 16/28* (2013.01); *C12N 9/1205* (2013.01); *A61K 38/00* (2013.01); *A61K 2239/17* (2023.05); *A61K 2239/21* (2023.05); *A61K 2239/31* (2023.05); *A61K 2239/38* (2023.05); *A61K 2239/47* (2023.05); *C12Y 207/01112* (2013.01)

(58) Field of Classification Search
CPC .... A61K 40/11; A61K 40/31; A61K 40/4211; C07K 2317/622; C07K 14/705
USPC ........................................................ 424/93.21
See application file for complete search history.

(56) References Cited

U.S. PATENT DOCUMENTS

| | | | |
|---|---|---|---|
| 4,946,778 | A | 8/1990 | Ladner et al. |
| 5,258,498 | A | 11/1993 | Huston et al. |
| 6,420,377 | B1 | 7/2002 | Lee et al. |
| 6,537,988 | B2 | 3/2003 | Lee |
| 2016/0175359 | A1 | 6/2016 | Spencer et al. |
| 2018/0237533 | A1 | 8/2018 | Juillerat et al. |

OTHER PUBLICATIONS

Sterner, Blood Cancer Journal (2021) 11:69, 11 pages.*
Drent et al. "Combined CD28 and 4-1BB Costimulation Potentiates Affinity-tuned Chimeric Antigen Receptor-engineered T Cells" Clinical Cancer Research, 25(13):4014-4025 (2019).
GenBank Accession No. AAP36481.1 "*Homo sapiens* protein tyrosine phosphatase, non-receptor type 6, partial [syntheticconstruct]" https://www.ncbi.nlm.nih.gov/ (2 pages) (Jul. 25, 2016).
International Search Report and the Written Opinion of the International Searching Authority corresponding to International Patent Application No. PCT/US2020/058083 (14 pages) (mailed Feb. 24, 2021).
Juillerat et al. "Design of chimeric antigen receptors with integrated controllable transient functions" Scientific Reports, 6(18950):1-7 (2016).
Sun et al. "THEMIS-SHP1 Recruitment by 4-1BB Tunes LCK-Mediated Priming of Chimeric Antigen Receptor-Redirected T Cells" Cancer Cell, 37:216-225 (2020).
Bayle et al. "Rapamycin Analogs with Differential Binding Specificity Permit Orthogonal Control of Protein Activity" Chemistry & Biology, 13:99-107 (2006).
Diaconu et al. "Inducible Caspase-9 Selectively Modulates the Toxicities of CD19-Specific Chimeric Antigen Receptor-Modified T Cells" Molecular Therapy, 25(3):580-592 (2017).
Du et al. "Antitumor Responses in the Absence of Toxicity in Solid Tumors by Targeting B7-H3 via Chimeric Antigen Receptor T Cells" Cancer Cell, 35(2):221-237 (2019).
Huston et al. "Protein engineering of single-chain Fv analogs and fusion proteins" Methods in Enzymology, 203:46-88 (1991).
International Preliminary Report on Patentability corresponding to International Patent Application No. PCT/US2020/058083 (8 pages) (dated May 12, 2022).
Kawalekar et al. "Distinct Signaling of Coreceptors Regulates Specific Metabolism Pathways and Impacts Memory Development in CAR T Cells" Immunity, 44(2):380-390 (2016).
Long et al. "4-1BB costimulation ameliorates T cell exhaustion induced by tonic signaling of chimeric antigen receptors" Nature Medicine, 21:581-590 (2015).
Luik et al. "Oligomerization of STIM1 couples ER calcium depletion to CRAC channel activation" Nature, 454 (7203):538-542 (2008).
NCBI Reference Sequence: NM_001042771.2 "*Homo sapiens* LCK proto-oncogene, Src family tyrosine kinase (LCK), transcript variant 1, mRNA" www.ncbi.nlm.nih.gov (5 pages) (Jul. 26, 2020).
NCBI Reference Sequence: NM_001164685.1 "*Homo sapiens* thymocyte selection associated (THEMIS), transcript variant 1, mRNA" www.ncbi.nlm.nih.gov (5 pages) (Feb. 13, 2021).

(Continued)

*Primary Examiner* — Valarie E Bertoglio
(74) *Attorney, Agent, or Firm* — Myers Bigel, P.A.

(57) ABSTRACT

The present invention provides chimeric antigen receptors (CAR) and methods of use in the treatment of diseases and disorders.

12 Claims, 20 Drawing Sheets

Specification includes a Sequence Listing.

(56) References Cited

OTHER PUBLICATIONS

NCBI Reference Sequence: NM_002831.5 "*Homo sapiens* protein tyrosine phosphatase, non-receptor type 6 (PTPN6), transcript variant 1, mRNA" www.ncbi.nlm.nih.gov (6 pages) (Nov. 18, 2018).
Rosenberg et al. "Use of Tumor-Infiltrating Lymphocytes and Interleukin-2 in the Immunotherapy of Patients with Metastatic Melanoma" New England Journal of Medicine, 319:1676-1680 (1988).
Salter et al. "Phosphoproteomic analysis of chimeric antigen receptor signaling reveals kinetic and quantitative differences that affect cell function" Science Signaling, 11:544 (2018).
Shu et al. "Secretion of a single-gene-encoded immunoglobulin from myeloma cells" Proceedings of the National Academy of Sciences USA, 90:7995-7999 (1993).
Skerra et al. "Assembly of a Functional Immunoglobulin Fv Fragment in *Escherichia coli*" Science, 240(4855):1038-1041 (1988).
Van Der Stegen et al. "The pharmacology of second-generation chimeric antigen receptors" Nature Reviews Drug Discovery, 14(7):499-509 (2015).
Zhao et al. "Structural Design of Engineered Costimulation Determines Tumor Rejection Kinetics and Persistence of CAR T Cells" Cancer Cell, 28(4):415-428 (2015).
Liu, et al., "Engineering switchable and programmable universal CARs for CAR T therapy", Journal of Hematology & Oncology 12:69, 2019 (9 pages).

* cited by examiner

FIG. 2C

METHODS AND COMPOSITIONS FOR CHIMERIC ANTIGEN RECEPTOR TARGETING CANCER CELLS

STATEMENT OF PRIORITY

This patent application is a 35 U.S.C. § 371 national phase application of PCT Application PCT/US2020/058083 filed Oct. 30, 2020, which claims the benefit, under 35 U.S.C. § 119(e), of U.S. Provisional Application No. 62/928,675, filed on Oct. 31, 2019, the entire contents of each of which are incorporated by reference herein

STATEMENT OF GOVERNMENT SUPPORT

This invention was made with government support under Grant Number CA193140 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-862_ST25.txt, 15.432 bytes in size, generated on Apr. 27, 2022 and filed via EFS-Web, is provided in lieu of a paper copy. This Sequence Listing is hereby incorporated herein by reference into the specification for its disclosures.

FIELD OF THE INVENTION

The present invention is directed to chimeric antigen receptor (CAR) compositions and methods of their use in cancer immunotherapy.

BACKGROUND OF THE INVENTION

This invention describes compositions and methods for a chimeric antigen receptor (CAR) that reduce or enhance CAR kinetics of activity and activation threshold.

CARs are synthetic molecules composed of a single chain variable fragment (scFv), co-stimulatory moieties (either CD28 or 4-1BB) and a CD3ζ signaling domain that when expressed by T lymphocytes trigger their lytic machinery and costimulation upon antigen engagement. In clinical studies, CAR co-stimulation plays an essential role in promoting the expansion of CAR-redirected T cells, and both CD28 and 4-1BB lead to equally significant clinical responses in B cell malignancies. However, CD28- and 4-1BB-mediated costimulation in CAR-T cells has been associated with distinct antitumor kinetics as CD28 endodomain promotes faster antitumor activity as compared to 4-1BB endodomain. This phenomenon correlates with the observed pronounced glycolytic metabolism and higher susceptibility to exhaustion of the CD28-mediated costimulation as opposed to the predominantly oxidative metabolism and lower susceptibility to exhaustion of the 4-1BB-mediated co-stimulation.

Phosphatidylinositol-4,5-bisphosphate 3-kinase (PI3K) and tumor necrosis factor receptor associated factors (TRAFs) are known downstream signaling molecules recruited by CD28 and 4-1BB, respectively. However, PI3K and TRAF signaling do not explain the observed functional differences between CD28 and 4-1BB co-stimulation and it remains elusive whether key signaling events occur within the CAR synapse causing the observed kinetics of antitumor activity.

The present invention overcomes previous shortcomings in the art by providing chimeric antigen receptors with more predictable activity and safer clinical profile and methods of their use in treating cancer.

SUMMARY OF THE INVENTION

The present invention provides methods and compositions for the treatment of cancer, including treatment of cancer employing immunotherapy. In particular cases, the immunotherapy includes T lymphocytes engineered to target certain cancers.

Thus, one aspect of the present invention provides chimeric antigen receptors (CAR) comprising a hinge region, a transmembrane domain, a CD3ζ domain, a scFv, a CD28 costimulatory molecule, and an FKBP-rapamycin binding domain (FRB).

Another aspect of the present invention provides polypeptides comprising an FKBP sequence linked to SHP1.

An additional aspect of the present invention provides compositions comprising: a CAR comprising a 4-1BB costimulatory molecule; and a lymphocyte-specific protein tyrosine kinase (LCK) protein.

Further provided herein are related nucleic acid molecules, recombinant expression vectors, host cells, populations of cells, antibodies or antigen binding portions thereof, antibody fragments and pharmaceutical compositions relating to the CARs of the invention.

A further aspect of the present invention provides methods of reducing a T cell-mediated immune stimulation to a target cell population or tissue in a subject, comprising administering to the subject an effective amount of a cell of the present invention (e.g., a cell comprising a CAR of the present invention), and administering (e.g., concurrently with, prior to, and/or afterward) an effective amount of AP21967 and/or functional analogue thereof, wherein the AP21967 and/or functional analogue thereof dimerizes the CAR and the polynucleotide, thereby reducing the T cell-mediated immune stimulation.

A further aspect of the present invention provides methods of reducing CAR T cell-mediated immune stimulation bystander cytotoxicity in a subject having cancer, comprising a) administering to the subject an effective amount of a cell of the present invention, wherein said cells induce an unacceptable level of bystander cytotoxicity; and b) administering (e.g., concurrently with, prior to, and/or afterward) an effective amount of AP21967 and/or functional analogue thereof, wherein the AP21967 and/or functional analogue thereof dimerizes the CAR and the polynucleotide, thereby reducing the CAR T cell-mediated immune stimulation and bystander cytotoxicity.

An additional aspect of the present invention provides methods of enhancing T cell-mediated immune stimulation to a target cell population or tissue in a subject, comprising administering to the subject an effective amount of a cell of the present invention (e.g., a cell comprising a CAR of the present invention), wherein the exogenous LCK is overexpressed in the cell as compared to wildtype LCK, thereby enhancing the T cell-mediated immune stimulation.

Another aspect of the present invention provides methods of enhancing T cell-mediated immune stimulation to a target cell population or tissue in a subject, comprising administering to the subject an effective amount of a cell comprising a CAR comprising a 4-1BB costimulatory molecule and an exogenous LCK protein, wherein the exogenous LCK is overexpressed in the cell as compared to wildtype LCK, thereby enhancing the T cell-mediated immune stimulation.

A further aspect of the present invention provides methods of stimulating a T cell-mediated immune response to a target cell population or tissue in a subject, comprising administering to the subject an effective amount of a cell of the present invention (e.g., a cell comprising a CAR of the present invention), thereby stimulating a T cell-mediated immune response to the target cell population or tissue in the subject.

Another aspect of the present invention provides methods of treating a subject having a disease or disorder associated with elevated expression of a target antigen by a cell of the subject, comprising administering to the subject an effective amount of a cell of the present invention (e.g., a cell comprising a CAR of the present invention), thereby treating the subject having the disease or disorder associated with elevated expression of the target antigen by the cell of the subject.

Another aspect of the present invention provides methods of generating a population of genetically engineered cells in a subject, comprising administering to the subject a cell genetically engineered to express a CAR of the present invention, wherein the population of genetically engineered cells persists in the subject for a period of time following administration.

An additional aspect of the present invention provides methods of generating a population of genetically engineered cells in a subject, comprising administering to the subject a cell of the present invention (e.g., a cell comprising a CAR of the present invention), wherein the cell expands into and persists as a population of genetically engineered cells in the subject for a period of time following administration.

A further aspect of the present invention provides methods of expanding a population of genetically engineered cells in a subject, comprising administering to the subject a cell genetically engineered to express a CAR of the present invention, wherein the administered genetically engineered cell produces a population of progeny cells in the subject.

An additional aspect of the present invention provides methods of expanding a population of genetically engineered cells in a subject, comprising administering to the subject a cell of the present invention (e.g., a cell comprising a CAR of the present invention), wherein the cell produces a population of progeny cells in the subject.

Another aspect of the present invention provides methods of treating cancer in a subject, comprising administering to the subject an effective amount of a cell of the present invention (e.g., a cell comprising a CAR of the present invention), thereby treating cancer in the subject.

Another aspect of the present invention provides methods of targeting a cancer cell and/or a cancer initiating cell (CIC) having a target antigen, comprising providing to the cancer cell and/or the CIC a cell comprising a CAR of the present invention.

Another aspect of the present invention provides methods of targeting a cancer cell and/or a cancer initiating cell (CIC) having a target antigen, comprising providing to the cancer cell and/or the CIC a cell of the present invention (e.g., a cell comprising a CAR of the present invention).

Another aspect of the present invention provides methods of detecting cancer cells and/or cancer initiating cells (CICs) in a cell sample, comprising: a) contacting the cell sample with a CAR of the present invention under conditions whereby a binding complex can form; and b) detecting formation of the binding complex, wherein detection of the binding complex is indicative of cancer cells and/or CICs in the cell sample.

Another aspect of the present invention provides methods of detecting cancer cells and/or cancer initiating cells (CICs) in a subject, comprising: a) contacting a cell sample obtained from the subject with a CAR of the present invention under conditions whereby a binding complex can form; and b) detecting formation of the binding complex, wherein detection of the binding complex is indicative of the presence of cancer cells and/or CICs in the subject.

A further aspect of the present invention provides methods of stimulating a T cell-mediated immune response to a target cell population or tissue in a subject, comprising administering to the subject an effective amount of a CAR composition selected from the group consisting of: a) a CAR composition comprising: a CAR comprising a hinge region, a transmembrane domain, a CD3ζ domain, an scFv, a CD28 costimulatory molecule, and an FRB; b) a CAR composition comprising: (i) a CAR comprising a hinge region, a transmembrane domain, a CD3ζ domain, an scFv, a CD28 costimulatory molecule, and an FRB; and (ii) a polypeptide comprising an FKBP linked to SHP1; c) a CAR composition comprising: (i) a CAR comprising a 4-1BB costimulatory molecule; and (ii) an LCK protein; d) a CAR composition comprising: (i) a CAR comprising a hinge region, a transmembrane domain, a CD3ζ domain, an scFv, a CD28 costimulatory molecule, and an FRB; (ii) a CAR comprising a 4-1BB costimulatory molecule; and (iii) an LCK protein; e) a CAR composition comprising: (i) a CAR comprising a hinge region, a transmembrane domain, a CD3ζ domain, an scFv, a CD28 costimulatory molecule, and an FRB; (ii) a polypeptide comprising an FKBP linked to SHP1; (iii) a CAR comprising a 4-1BB costimulatory molecule; and (iv) n LCK protein; thereby stimulating a T cell-mediated immune response to the CD19 expressing target cell population or tissue in the subject.

A further aspect of the present invention provides methods of treating a subject having a disease or disorder associated with elevated expression of a target antigen by a cell of the subject, comprising administering to the subject an effective amount of a CAR composition selected from the group consisting of: a) a CAR composition comprising: a CAR comprising a hinge region, a transmembrane domain, a CD3ζ domain, an scFv, a CD28 costimulatory molecule, and an FRB; b) a CAR composition comprising: (i) a CAR comprising a hinge region, a transmembrane domain, a CD3ζ domain, an scFv, a CD28 costimulatory molecule, and an FRB; and (ii) a polypeptide comprising an FKBP linked to SHP1; c) a CAR composition comprising: (i) a CAR comprising a 4-1BB costimulatory molecule; and (ii) an LCK protein; d) a CAR composition comprising: (i) a CAR comprising a hinge region, a transmembrane domain, a CD3ζ domain, an scFv, a CD28 costimulatory molecule, and an FRB; (ii) a CAR comprising a 4-1BB costimulatory molecule; and (iii) an LCK protein; e) a CAR composition comprising: (i) a CAR comprising a hinge region, a transmembrane domain, a CD3ζ domain, an scFv, a CD28 costimulatory molecule, and an FRB; (ii) a polypeptide comprising an FKBP linked to SHP1; (iii) a CAR comprising a 4-1BB costimulatory molecule; and (iv) an LCK protein; thereby treating the subject having the disease or disorder associated with elevated expression of the target antigen by the cell of the subject.

BRIEF DESCRIPTION OF THE DRAWINGS

FIG. 1D shows CAR19.28ζ-T and CAR19.BBζ-T cells stimulated with the $CD19^+$ BV173 cell line at different tumor to T cell ratios (T:E). IFNγ levels in the culture supernatants were measured (n=4, two-way ANOVA; representative of 6 donors). For FIGS. 1E and 1F, NSG mice engrafted with the $CD19^+$ Daudi cell line were infused with differentially labeled CAR19.28ζ-T and CAR19.BBζ-T cells mixed at a 1:1 ratio. Samples were collected 6 hours after infusion. Non-tumor bearing NSG mice, infused with mixed CAR19.28ζ-T and CAR19.BBζ-T cells, were used as a negative control. FIG. 1E shows a summary of CD69 expression in T cells (n=5, two-tailed unpaired t-test). FIG. 1F shows representative flow cytometry plots showing T cells (CD45+CD3+) and Daudi tumor cells (CD45+$CD3^-$) identified in the peripheral blood, bone marrow, lung, and spleen. FIG. 1G shows phosphorylation of CAR-CD3ζ, ZAP70, and LAT in CAR19.28ζ-T and CAR19.BBζ-T cells after stimulation with the anti-CAR19 Ab at 10 μg/ml. Cells were incubated with the anti-CAR19 Ab followed by incubation with a goat anti-mouse IgG secondary antibody on ice. CAR-T cells were then transferred to 37° C. for indicated time to be activated (n=3). FIG. 1H shows CAR-CD3ζ phosphorylation of CAR19.28ζ-T and CAR.19.BBζ-T cells in the absence of CAR crosslinking. Total CAR detected by the CD3ζ chain Ab was used as equal loading. Results of 3 representative donors were shown. FIG. 1J shows representative flow plots showing the expression of CARGD2 (targeting the GD2 antigen) and CAR138 (targeting the CD138 antigen) in T cells of one representative donor at day 6 of culture (FIG. 1J, top panel) and (FIG. 1J, bottom panel) CAR-CD3ζ Y142 phosphorylation in CARGD2-T cells and CAR138-T cells collected at day 10 of culture. Results of 3 representative donors are shown. FIG. 1J shows a schema of CAR19 constructs with different hinge (CD8α vs. IgG1h) or transmembrane (CD8α vs. CD28) domains (FIG. 1J, top panel) and representative flow plots of the expression of CARs in one representative donor at day 6 of culture (FIG. 1J, left panel). FIG. 1J, right panel shows CAR-CD3ζ Y142 phosphorylation of CAR-T cells with CD28 transmembrane domain as compared to those with CD8α transmembrane domain, and CAR-CD3ζ Y142 phosphorylation in CAR-T cells with the IgG1 hinge as compared to those with the CD8α hinge. Cells were collected at day 10 of culture. Results of 2 representative donors are shown.

FIGS. 2A-2G show that LCK/THEMIS-SHP1 equilibrium determines the basal CAR-CD3ζ phosphorylation and activation magnitude of CAR19.28ζ-T and CAR19.BBζ-T cells. FIG. 2A top panel shows phosphorylation of CAR-CD3ζ in CAR19.28ζ-T and CAR19.BBζ-T cells treated with DMSO (Ctrl), Src family kinase (PP2) or LCK (Inh-II) inhibitors at 10 μM for 16 hours. Results of 2 representative donors were shown. FIG. 2A bottom panel shows high doses of anti-CAR19 Ab partially overcame the PP2-mediated inhibition in CAR19.28ζ-T cells. FIG. 2B shows IFNγ release and CD69 expression in CAR19.28ζ-T and CAR.19.BBζ-T cells pretreated with 10 μM PP2 for 16 hours and then stimulated with anti-CAR19 Ab at various concentrations for 6 hours. CAR19.28ζ-T and CAR19.BBζ-T cells not exposed to PP2 were used as control. An additional negative control is represented by CAR19.CD3Y6Fζ-T cells, which are T cells expressing the CAR19 in which all six tyrosine (Y) residues of the three ITAMs of CAR-CD3ζ were mutated to phenylalanine (F) to completely abrogate tyrosine phosphorylation of the CAR-CD3ζ (n=3 for IFNγ release, n=5 for CD69 expression, two-way ANOVA; p value between CAR19.28ζ-T cells and CAR19.28ζ-T cells+PP2 groups). FIG. 2C shows a schema of the CAR19.28ζ constructs in which specific mutations were included to generate CAR19.28AAAζ, CAR19.28YFζ and CAR19.28AFAAζ (FIG. 2C, top left panel; CAR19.28AAAζ mutation of PYAPP to AYAAA; CAR19.28YFζ mutation of PYAPP to PFAPP; CAR19.28AFAAζ, mutation of PYAPP to AFAAA.) CAR was pulled down from CAR19.28ζ-T and CAR19.28AAAζ-T cells at day 14 of culture. LCK in the IP product was evaluated by western blot using an anti-LCK Ab (FIG. 2C, bottom left panel). CAR-T cells were collected for analysis at day 10 of culture. CAR-CD3ζ Y142 phosphorylation was assessed by western blot. Results of 2 representative donors were shown in FIG. 2C, bottom right panels. FIG. 2C top right panels show cytokine release of CAR-T cells stimulated with the anti-CAR19 Ab at different concentrations for 6 hours. Cells were collected at day 14 of culture (n=3, two-way ANOVA; ns, not significant between CAR19.28ζ-T and CAR19.28AAAζ-T, CAR19.28YFζ-T or CAR19.28AFAAζ-T cells). FIG. 2D top panel shows phosphorylation of CAR-CD3ζ Y142 in $CD4^+$ T cells expressing either CAR19.28ζ or CAR19.BBζ and co-transduced with the CD8α mutant (CD8α-SKS) or wild type CD8α (CD8α-wt). Results of 2 representative donors are shown. FIG. 2D bottom panel shows the wild-type CD4 in both $CD4^+$ and CD8+CAR19.BBζ-T cells increased the basal phosphorylation of CAR-CD3ζ. FIG. 2E shows phosphorylation of CAR-CD3ζ Y142 in CAR19.28ζ-T and CAR19.BBζ-T cells treated with 200 μM phosphatase inhibitor $Na_3VO_4$. Results of 2 representative donors are shown. FIG. 2F shows THEMIS expression and CAR-CD3ζ Y142 phosphorylation in CAR19.28ζ-T and CAR19.BBζ-T cells co-transduced with vectors encoding siRNAs specific for THEMIS. Results of 2 representative donors are shown. FIG. 2G shows phosphorylation of CAR-CD3ζ Y142 in CAR19.BBζ-T and CAR19.BBζ-ΔC10-T cells. Results of 2 representative donors are shown.

DETAILED DESCRIPTION OF THE INVENTION

Figure 1A:
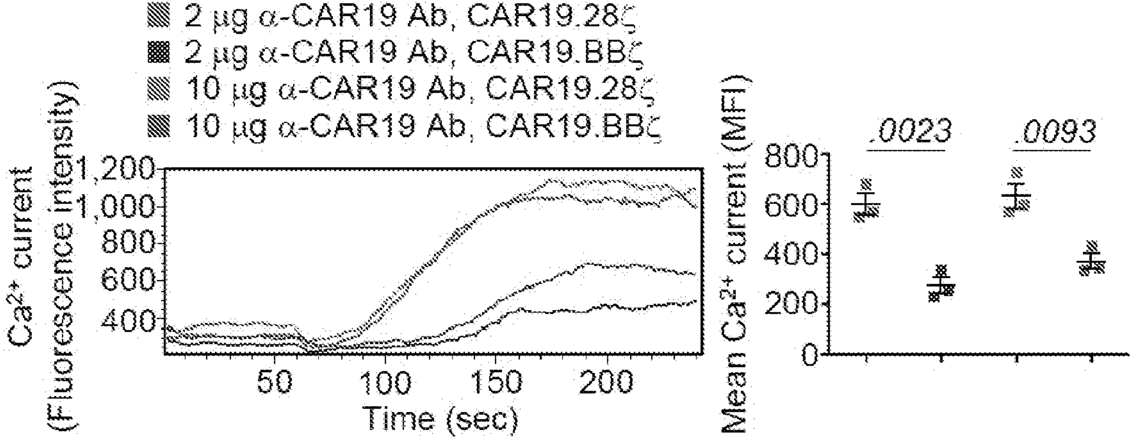
FIGS. 1A-1J show CAR19.28ζ-T cells show higher magnitude of activation than CAR19.BBζ-T cells after CAR crosslinking. CAR19.28ζ-T and CAR19.BBζ-T cells were stimulated with different concentrations of anti-CAR19 Ab and $Ca^{2+}$ influx (FIG. 1A), CD69 expression in $CD4^+$ and $CD8^+$ T cells (FIG. 1B), and IFNγ release (FIG. 1C) were measured (n=3 in a, one-way ANOVA; n=17 in b, n=3 in c, two-way ANOVA).

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

In the following description, certain details are set forth such as specific quantities, sizes, etc. so as to provide a thorough understanding of the present embodiments disclosed herein. However, it will be obvious to those skilled in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

Unless otherwise defined, all technical and scientific terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention.

All publications, patent applications, patents and other references mentioned herein are incorporated by reference in their entirety. In case of a conflict in terminology, the present specification is controlling.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for production of recombinant and synthetic polypeptides, antibodies or antigen-binding fragments thereof, manipulation of nucleic acid sequences, production of transformed cells, the construction of rAAV constructs, modified capsid proteins, packaging vectors expressing the AAV rep and/or cap sequences, and transiently and stably transfected packaging cells. Such techniques are known to those skilled in the art. See, e.g., SAMBROOK et al., MOLECULAR CLONING: A LABORATORY MANUAL 2nd Ed. (Cold Spring Harbor, NY, 1989); F. M. AUSUBEL et al. CURRENT PROTOCOLS IN MOLECULAR BIOLOGY (Green Publishing Associates, Inc. and John Wiley & Sons, Inc., New York).

Definitions

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

"Optional" or "optionally" means that the subsequently described event or circumstance can or cannot occur, and that the description includes instances where the event or circumstance occurs and instances where it does not.

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

Also as used herein, "one or more" means one, two, three, four, five, six, seven, eight, nine, ten, 11, 12, 13, 14, 15, 16, 17, 18, 19, 20, etc.

As used herein, the transitional phrase "consisting essentially of" is to be interpreted as encompassing the recited materials or steps and those that do not materially affect the basic and novel characteristic(s) of the claimed invention. Thus, the term "consisting essentially of" as used herein should not be interpreted as equivalent to "comprising."

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence or between the two ends (e.g., between domains) such that the function of the polynucleotide or polypeptide is not materially altered. The total of ten or less additional nucleotides or amino acids includes the total number of additional nucleotides or amino acids added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in biological activity of at least about 50% or more as compared to the activity of a polypeptide consisting of the recited sequence.

Amino acid as used herein refers to a compound having a free carboxyl group and a free unsubstituted amino group on the a carbon, which may be joined by peptide bonds to form a peptide active agent as described herein. Amino acids may be standard or non-standard, natural or synthetic, with examples (and their abbreviations) including but not limited to:

Asp=D=Aspartic Acid
Ala=A=Alanine
Arg=R=Arginine
Asn=N=Asparagine
Cys=C=Cysteine
Gly=G=Glycine
Glu=E=Glutamic Acid
Gln=Q=Glutamine
His=H=Histidine
Ile=I=Isoleucine
Leu=L=Leucine
Lys=K=Lysine
Met=M=Methionine
Phe=F=Phenylalanine
Pro=P=Proline
Ser=S=Serine
Thr=T=Threonine
Trp=W=Tryptophan
Tyr=Y=Tyrosine
Val=V=Valine
Orn=Ornithine Nal=2-napthylalanine
Nva=Norvaline
Nle=Norleucine
Thi=2-thienylalanine
Pcp=4-chlorophenylalanine
Bth=3-benzothienyalanine
Bip=4,4'-biphenylalanine
Tic=tetrahydroisoquinoline-3-carboxylic acid
Aib=aminoisobutyric acid
Anb=α-aminonormalbutyric acid
Dip=2,2-diphenylalanine
Thz=4-Thiazolylalanine All peptide sequences mentioned herein are written according to the usual convention whereby the N-terminal amino acid is on the left and the C-terminal amino acid is on the right. A short line (or no line) between two amino acid residues indicates a peptide bond.

"Basic amino acid" refers to any amino acid that is positively charged at a pH of 6.0, including but not limited to R, K, and H.

"Aromatic amino acid" refers to any amino acid that has an aromatic group in the side-chain coupled to the alpha carbon, including but not limited to F, Y, W, and H.

"Hydrophobic amino acid" refers to any amino acid that has a hydrophobic side chain coupled to the alpha carbon, including but not limited to I, L, V, M, F, W and C, most preferably I, L, and V.

"Neutral amino acid" refers to a non-charged amino acid, such as M, F, W, C and A.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well-known to those of skill in the art. See, e.g., Pearson (1994) *Methods Mol. Biol.* 24: 307-331, herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-Isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) *Science* 256: 1443 45, herein incorporated by reference. A "moderately conservative" replacement is any change having a nonnegative value in the PAM250 log-likelihood matrix.

The term "sequence identity," as used herein, has the standard meaning in the art. As is known in the art, a number of different programs can be used to identify whether a polynucleotide or polypeptide has sequence identity or similarity to a known sequence. Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) *J Mol. Biol.* 215: 403 410 and Altschul et al. (1997) *Nucleic Acids Res.* 25:3389 402, each of which is herein incorporated by reference in its entirety.

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer nucleotides than the polynucleotides specifically disclosed herein, it is understood that in one embodiment, the percentage of sequence identity will be determined based on the number of identical nucleotides in relation to the total number of nucleotides. Thus, for example, sequence identity of sequences shorter than a sequence specifically disclosed herein, will be determined using the number of nucleotides in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As used herein, the term "nucleic acid" refers to a single or double-stranded polymer of deoxyribonucleotide or ribonucleotide bases read from the 5' to the 3' end. The "nucleic acid" may also optionally contain non-naturally occurring or modified nucleotide bases. The term "nucleotide sequence" or "nucleic acid sequence" refers to both the sense and antisense strands of a nucleic acid as either individual single strands or in the duplex.

As used herein, the term "modified," as applied to a polynucleotide or polypeptide sequence, refers to a sequence that differs from a wild-type sequence due to one or more deletions, additions, substitutions, or any combination thereof.

The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectible activity (at most, an insignificant amount, e.g., less than about 10% or even 5%).

The term "endogenous" refers to a component naturally found in an environment, i.e., a gene, nucleic acid, miRNA, protein, cell, or other natural component expressed in the subject, as distinguished from an introduced component, i.e., an "exogenous" component.

The terms "polypeptide," "peptide" and "protein" may be used interchangeably to refer to polymers of amino acids of any length. The terms "nucleic acid," "nucleic acid sequence," and "polynucleotide" may be used interchangeably to refer to polymers of nucleotides of any length. As used herein, the terms "nucleotide sequence," "polynucleotide," "nucleic acid sequence," "nucleic acid molecule" and "nucleic acid fragment" refer to a polymer of RNA, DNA, or RNA and DNA that is single- or double-stranded, optionally containing synthetic, non-natural and/or altered nucleotide bases.

The term coding region as used herein, refers to the portion of a polynucleotide, e.g., a gene that encodes a polypeptide.

As used herein with respect to nucleic acids, the term "operably linked" refers to a functional linkage between two or more nucleic acids. For example, a promoter sequence may be described as being "operably linked" to a heterologous nucleic acid sequence because the promoter sequences initiates and/or mediates transcription of the heterologous nucleic acid sequence. In some embodiments, the operably linked nucleic acid sequences are contiguous and/or are in the same reading frame.

As used herein, the terms "target tissue" and "off-target tissue" refer to bodily regions, organs, tissues, structures and/or cells of the subject wherein a specified nucleic acid or protein of interest is expressed. "Target tissues" are those regions, organs, tissues, structures and/or cells of the subject wherein the endogenous nucleic acid or protein of interest is expressed under typical healthy and/or diseased conditions. "Off-target tissues" are those regions, organs, tissues, structures and/or cells of the subject wherein the endogenous nucleic acid or protein of interest is not expressed under typical healthy and/or diseased conditions.

A "vector" refers to a compound used as a vehicle to carry foreign genetic material into another cell, where it can be replicated and/or expressed. A cloning vector containing foreign nucleic acid is termed a recombinant vector. Examples of nucleic acid vectors are plasmids, viral vectors, cosmids, expression cassettes, and artificial chromosomes. Recombinant vectors typically contain an origin of replication, a multicloning site, and a selectable marker. The nucleic acid sequence typically consists of an insert (recombinant nucleic acid or transgene) and a larger sequence that serves as the "backbone" of the vector. The purpose of a vector which transfers genetic information to another cell is typically to isolate, multiply, or express the insert in the target cell. Expression vectors (expression constructs or expression cassettes) are for the expression of the exogenous gene in the target cell, and generally have a promoter sequence that drives expression of the exogenous gene. Insertion of a vector into the target cell is referred to transformation or transfection for bacterial and eukaryotic cells, although insertion of a viral vector is often called transduction. The term "vector" may also be used in general to describe items to that serve to carry foreign genetic material into another cell, such as, but not limited to, a transformed cell or a nanoparticle.

By "pharmaceutically acceptable" it is meant a material that is not toxic or otherwise undesirable, i.e., the material may be administered to a subject without causing any undesirable biological effects.

By the term "treat," "treating," or "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition and/or prevention or delay of the onset of a disease or disorder.

As used herein, the term "prevent," "prevents," or "prevention" (and grammatical equivalents thereof) refers to a delay in the onset of a disease or disorder or the lessening of symptoms upon onset of the disease or disorder. The terms are not meant to imply complete abolition of disease and encompass any type of prophylactic treatment that reduces the incidence of the condition or delays the onset and/or progression of the condition.

A "treatment effective amount", "effective amount", "amount effective to treat" or the like as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

As used herein, "prevent," "preventing" or "prevention" includes prophylactic treatment of the subject to prevent the onset or advancement of a disorder, as determined, e.g., by the absence or delay in the manifestation of symptoms associated with the disorder. As used herein, "prevent," "preventing" or "prevention" is not necessarily meant to imply complete abolition of symptoms. A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The term "administering" or "administration" of a synthetic gene, expression cassette, vector, plasmid, viral vector, transformed cell, nanoparticle, or pharmaceutical composition to a subject includes any route of introducing or delivering to a subject a compound to perform its intended function. Administration can be carried out by any suitable route, including orally, intranasally, parenterally (intravenously, intramuscularly, intraperitoneally, intracisternally, intrathecally, intraventricularly, or subcutaneously), or topically. Administration includes self-administration and the administration by another.

The present invention provides embodiments of the amino acid sequences and nucleotide sequences of this invention wherein the amino acid sequence and/or the nucleotide sequence has at least 70% (e.g., 70, 71, 72, 73, 74, 75, 76, 77, 78, 79, 80, 81, 82, 83, 84, 85, 86, 87, 88, 89, 90, 91, 92, 93, 94 95, 96, 97, 98, 99 or 100%) identity with the amino acid sequence and/or nucleotide sequences described herein. The present invention further encompasses all nucleotide sequences that encode the amino acid sequences described herein.

Compositions

The present invention is based on the discovery that downstream signaling of chimeric antigen receptors (CAR) can be modulated by particular kinases such as lymphocyte-specific protein tyrosine kinase (LCK). While not wishing to be bound to theory, the inventors of the present invention found that the observed phenomena that CAR-T cells with a CD28 costimulatory domain (e.g., CAR.28ζ) show faster kinetics of activity and lower activation threshold than CAR-T cells with a 4-1BB costimulatory domain (e.g., CAR.BBζ) may be due to an imbalance of kinase and phosphatase activity between the CAR.28ζ synapse and CAR.BBζ synapse; specifically, wherein there is more kinase activity in the CAR.28ζ synapse resulting from LCK recruited by co-receptors, while additional recruitment of THEMIS/SHP-I phosphatase complex in the CAR.BBζ synapse counteracts the effects of LCK, thus resulting in faster kinetics of activity and lower activation threshold in CAR-T cells with a 4-1BB costimulatory domain.

Thus, in one embodiment, the present invention provides a chimeric antigen receptor (CAR) comprising a hinge region, a transmembrane domain, a CD3ζ domain, an scFv, and a costimulatory molecule. In some embodiments, the present invention provides a CAR comprising a hinge region, a transmembrane domain, a CD3ζ domain, an scFv, a costimulatory molecule, and a KFBP-rapamycin binding domain (FRB). In some embodiments, the present invention provides a CAR comprising a hinge region, a transmembrane domain, a CD3ζ domain, an scFv, a CD28 costimulatory molecule, and an FRB.

In some embodiments, a CAR of the present invention comprises a transmembrane domain. Non-limiting examples of a transmembrane domain of the present invention include a CD8 (e.g., CD8α and/or CD8β), CD28, or CD4 transmembrane domain.

In some embodiments, a CAR of the present invention comprises an effector domain. As used herein, the term "effector domain" refers to a signaling domain that transduces the event of a receptor ligand binding to an intracellular signal that partially activates the cell (e.g., the T lymphocyte) expressing the CAR. Absent appropriate costimulatory signals, this even is insufficient for useful T cell activation and proliferation. A non-limiting example of an effector domain of this invention is the effector domain of the T cell receptor zeta (ζ) chain, also known as CD3ζ or CD247.

In some embodiments, a CAR of the present invention comprises one or more costimulatory molecules. As used herein, the term "costimulatory molecule" refers to a molecular component that promotes activation, proliferation and effector function of a T cell after engagement of an antigen specific receptor. The skilled artisan recognizes that T cells utilize costimulatory signals that are antigen non-specific to become fully activated. In particular cases they are provided by the interaction between co-stimulatory molecules expressed on the membrane of an antigen presenting cell (APC) and the T cell. Exemplary costimulatory molecules include one or more (e.g., 2, 3, 4, 5, 6, 7, 8, 9, 10, etc.) of the following in any combination: B7-1/CD80; CD28; B7-2/CD86; CTLA-4; B7-H1/PD-L1; ICOS; B7-H2; PD-1; B7-H3; PD-L2; B7-H4; PDCD6; BTLA; 4-1BB/TNFRSF9/CD137; CD40 Ligand/TNFSF5; 4-1BB Ligand/TNFSF9; GITR/TNFRSF18; BAFF/BLyS/TNFSF13B; GITR Ligand/TNFSF18; BAFF R/TNFRSF13C; HVEM/TNFRSF14; CD27/TNFRSF7; LIGHT/TNFSF14; CD27 Ligand/TNF SF7; OX40/TNFRSF4; CD30/TNFRSF8; OX40 Ligand/TNFSF4; CD30 Ligand/TNFSF8; TAC1/TNFRSF13B; CD40/TNFRSF5; 2B4/CD244/SLAMF4; CD84/SLAMF5; BLAME/SLAMF8; CD229/SLAMF3; CD2 CRACC/SLAMF7; CD2F-10/SLAMF9; NTB-A/SLAMF6; CD48/SLAMF2; SLAM/CD150; CD58/LFA-3; CD2; Ikaros; CD53; Integrin alpha 4/CD49d; CD82/Kai-1; Integrin alpha 4 beta 1; CD90/Thy1; Integrin alpha 4 beta 7/LPAM-1; CD96; LAG-3; CD160; LMIR1/CD300A; CRTAM; TCL1A; DAP12; TIM-1/KIM-1/HAVCR; Dectin-1/CLEC7A; TIM-4; DPPIV/CD26; TSLP; EphB6; TSLP R; and HLA-DR, or any other co-stimulatory molecule and/or active fragment thereof now known or later identified, singly or in any combination. In some embodiments, the one or more costimulatory molecules in the CAR may come from the B7/CD28 family, TNF superfamily, or the signaling lymphocyte activation molecule (SLAM) family. In some embodiments, the one or more costimulatory molecules in the CAR may be CD28 or 4-1BB.

In some embodiments, a CAR of the present invention comprises hinge region. In some embodiments, the hinge region of the present invention may comprise a hinge region of an antibody (e.g., IgM, IgD, IgA, IgG, IgE), including any isotypes thereof (e.g., IgG1, IgG2, IgG3, IgG4, etc.). Other non-limiting examples of a hinge region of the present invention include a hinge region of CD8α.

In some embodiments of the invention, a CAR of the present invention comprises a single-chain variable fragment (scFv). The skilled artisan recognizes that scFv is a fusion protein of the variable regions of the heavy (VH) and light chains (VL) of immunoglobulins, connected with a short linker peptide of ten to about 25 amino acids. The linker may be rich in glycine for flexibility and/or it may have serine or threonine for solubility, in certain cases. The scFv may be generated by methods known in the art, and in some embodiments the scFv may be humanized, caninized, felinized, or equinized according to protocols known in the art. The scFv may bind to any target of interest known in the art, such as, for example, proteins known to be expressed exclusively and/or elevated in cancerous or otherwise diseased tissues or environments as compared to healthy tissue. scFv targets (i.e., scFv binding targets) may also include proteins expressed on healthy tissues and/or cells such as immune-related antigens, e.g., in order to identify and/or modulate native host responses. Non-limiting examples of scFv targets include wherein the scFv binds to TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-β, SSEA-4, CD20, FRα, ERBB2(Her2/neu), MUC1, EGFR, NCAM, Prostase, PAP, ELF2M, EphB2, IGF-I receptor, CAIX, LMP2, gp100, bcr-abl, tyrosinase, EphA2, GM1, sLe, GM3, TGSS, HMW- MAA, FRβ, TEM1/CD248, TEM7R, CLDN6, GPRCSD, CXORF61, CD97, CD179a, ALK, PSA, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6,E7, MAGE A1, ETV6-AML, Sp17, XAGE1, Tie 2, MAD-CT-1, MAD-CT-2, FRA1, p53, p53 mutants, prostein, survivin, PCTA-1/Galectin8, MelanA/MART1, Ras, hTERT, ML-IAP, ERG (i.e., TMPRSS2 ETS fusion gene), NA17, PAX3, AR, cyclin B1, MYCN, RhoC, TRP-2, CYP1B1, BORIS, SART3, PAX5, OY-TES1, LCK, AKAP-4, SSX2, RAGE-1, RU1, RU2, CEA, hsp70-2, CD79a, CD79b, CD72, LAIR1, FCAR, LILRA2, CD300LF, CLEC12A, BST2, EMR2, LY75, GPC3, CLN18.2, CLN6, FCRL5, IGLL1, or any variant thereof. In certain aspects, one may use cytokine exodomains or other ligand/receptor molecules as exodomains to provide targeting to the tumor cells.

In some embodiments of the present invention, the CAR of the present invention comprises an FKBP-rapamycin binding domain (FRB). The FRB domain of the mammalian target of rapamycin (mTOR) protein binds with high affinity to FK506-binding proteins (FKBP) to form heterodimers. The FRB domain may be modified, e.g., modified in sequence. Modification of the FRB domain and/or a corresponding FKBP can control dimerization to an FKBP so that it only occurs upon the provision of an additional molecule, such as the small molecule AP201967 and/or a functional analog thereof (e.g., AP20187). Such binding may be referred to inducible binding/dimerization. Non-limiting examples of the use of an FRB modified for inducible dimerization include, e.g., Bayle et al. 2006 *Chemistry & Biology* 13:99-107, and Luik et al. 2008 *Nature* 454:538-42, incorporated herein by reference. The FRB domain may be linked to any of the components of a CAR of the present invention. In some embodiments, the FRB domain may be linked to the CD3ζ domain.

In some embodiments, the sequence of the FRB domain, e.g., the FRB domain modified for inducible dimerization, may be:

(SEQ ID NO: 1)
SRILWHEMWHEGLEEASRLYFGERNVKGMFEVLEPLHAMMERGPQ
TLKETSFNQAYGRDLMEAQEWCRKYMKSGNVKDLLQAWDLYYHVF
RRISK.

(FRB domain)

In some embodiments, the sequence of a corresponding FKBP, e.g., the FKBP modified for inducible dimerization, may be:

(SEQ ID NO: 2)
MLEGVQVETISPGDGRTFPKRGQTCVVHYTGMLEDGKKVDSSRDR
NKPFKFMLGKQEVIRGWEEGVAQMSVGQRAKLTISPDYAYGATGH
PGIIPPHATLVFDVELLKLE.

(FKBP domain)

In some embodiments, the present invention provides a CAR comprising, consisting essentially of, or consisting of the following amino acid sequence or an amino acid sequence at least 70% identical thereto, e.g., at least about 70, 75, 80, 85, 90, 91, 92, 93, 94, 95, 96, 97, 98, or 99% identical thereto:

(SEQ ID NO: 3)
MEFGLSWLFLVAILKGVQCSRDIQMTQTTSSLSASLGDRVTISCR
ASQDISKYLNWYQQKPDGTVKLLIYHTSRLHSGVPSRFSGSGSGT
DYSLTISNLEQEDIATYFCQQGNTLPYTFGGGTKLELKRGGGGSG
GGGSGGGGSGGGGSEVQLQQSGPGLVAPSQSLSVTCTVSGVSLPD
YGVSWIRQPPRKGLEWLGVIWGSETTYYNSALKSRLTIIKDNSKS
QVFLKMNSLQTDDTAIYYCAKHYYYGGSYAMDYWGQGTSVTVSST
RTTTPAPRPPTPAPTIASQPLSLRPEACRPAAGGAVHTRGLDFAC
DIYIWAPLAGTCGVLLLSLVITLYCRSKRSRLLHSDYMNMTPRRP
GPTRKHYQPYAPPRDFAAYRSRVKFSRSADAPAYQQGQNQLYNEL
NLGRREEYDVLDKRRGRDPEMGGKPRRKNPQEGLYNELQKDKMAE
AYSEIGMKGERRRGKGHDGLYQGLSTATKDTYDALHMQALPPRSG
GGSILWHEMWHEGLEEASRLYFGERNVKGMFEVLEPLHAMMERGP
QTLKETSFNQAYGRDLMEAQEWCRKYMKSGNVKDLLQAWDLYYHV
FRRISKDYKDDDDK.

(CAR19.CD28ζ)

The present invention additionally provides a nucleic acid molecule encoding the CAR of this invention. In some embodiments, the nucleic acid molecule can comprise a nucleotide sequence encoding the following amino acid sequence or an amino acid sequence at least 70% identical thereto, e.g., at least about 70, 75, 80, 85, 90, 91, 92, 93, 94, 95, 96, 97, 98, or 99% identical thereto:

(SEQ ID NO: 3)
MEFGLSWLFLVAILKGVQCSRDIQMTQTTSSLSASLGDRVTISCR
ASQDISKYLNWYQQKPDGTVKLLIYHTSRLHSGVPSRFSGSGSGT
DYSLTISNLEQEDIATYFCQQGNTLPYTFGGGTKLELKRGGGGSG
GGGSGGGGSGGGGSEVQLQQSGPGLVAPSQSLSVTCTVSGVSLPD
YGVSWIRQPPRKGLEWLGVIWGSETTYYNSALKSRLTIIKDNSKS
QVFLKMNSLQTDDTAIYYCAKHYYYGGSYAMDYWGQGTSVTVSST
RTTTPAPRPPTPAPTIASQPLSLRPEACRPAAGGAVHTRGLDFAC
DIYIWAPLAGTCGVLLLSLVITLYCRSKRSRLLHSDYMNMTPRRP
GPTRKHYQPYAPPRDFAAYRSRVKFSRSADAPAYQQGQNQLYNEL
NLGRREEYDVLDKRRGRDPEMGGKPRRKNPQEGLYNELQKDKMAE
AYSEIGMKGERRRGKGHDGLYQGLSTATKDTYDALHMQALPPRSG
GGSILWHEMWHEGLEEASRLYFGERNVKGMFEVLEPLHAMMERGP
QTLKETSFNQAYGRDLMEAQEWCRKYMKSGNVKDLLQAWDLYYHV
FRRISKDYKDDDDK.

(CAR19.CD28ζ)

In some embodiments, the present invention provides an FKBP linked to a SHP1. The FKBP may be modified, e.g., modified in sequence. Modification of the FKBP and/or corresponding FRB can control dimerization to an FKBP so that it only occurs upon the presence of (e.g., provision of) an additional molecule, such as the small molecule AP201967 and/or a functional analog thereof (e.g., AP20187). Such binding may be referred to inducible binding/dimerization. Non-limiting examples of the use of an FKBP modified for inducible dimerization include, e.g., Bayle et al. 2006 *Chemistry & Biology* 13:99-107, and Luik et al. 2008 *Nature* 454:538-42.

In some embodiments, a polypeptide comprising an FKBP linked to SHP1 may comprise the follow amino acid sequence or an amino acid sequence at least 70% identical thereto, e.g., at least about 70, 75, 80, 85, 90, 91, 92, 93, 94, 95, 96, 97, 98, or 99% identical thereto:

```
                                        (SEQ ID NO: 4)
MLEGVQVETISPGDGRTFPKRGQTCVVHYTGMLEDGKKVDSSRDR

NKPFKFMLGKQEVIRGWEEGVAQMSVGQRAKLTISPDYAYGATGH

PGIIPPHATL VFDVELLKLESGGGSGVDLSRGWFHRDLSGLDAE

TLLKGRGVHGSFLARPSRKNQGDFSLSVRVGDQVTHIRIQNSGDF

YDLYGGEKFATLTEL VEYYTQQQGVLQDRDGTIIHLKYPLNCSD

PTSERWYHGHMSGGQAETLLQAKGEPWTFLVRESLSQPGDFVLSV

LSDQPKAGPGSPLRVTHIKVMCEGGRYTVGGLETFDSLTDLVEHF

KKTGIEEASGAFVYLRQPYYATRVNAADIENRVLELNKKQESEDT

AKAGFWEEFESLQKQEVKNLHQRLEGQRPENKGKNRYKNILPFDH

SR VILQGRDSNIPGSDYINANYIKNQLLGPDENAKTYIASQGCL

EATVNDFWQMAWQENSRVIVMTTREVEKGRNKCVPYWPEVGMQRA

YGPYSVTNCGEHDTTEYKLRTLQVSPLDNGDLIREIWHYQYLSWP

DHGVPSEPGGVLSFLDQINQRQESLPHAGPIIVHCSAGIGRTGTI

IVIDMLMENISTKGLDCDIDIQKTIQMVRAQRSGMVQTEAQYKFI

YVAIAQFIETTKKKLEVLQSQKGQESEYGNITYPPAMKNAHAKAS

RTSSKHKEDVYENLHTKNKREEKVKKQRSADKEKSKGSLKRK.
```

(FKBP-SHP1 construct)

In some embodiments, the present invention provides a composition comprising: a CAR comprising a 4-1BB costimulatory molecule; and a lymphocyte-specific protein tyrosine kinase (LCK) protein. In some embodiments, the 4-1BB CAR of the composition comprises an FRB domain (e.g., a modified FRB domain, e.g., an FRB domain that undergoes inducible binding to an FKBP protein in the presence of (e.g., provision of) an additional molecule, such as the small molecule AP201967 and/or a functional analog thereof (e.g., AP20187)). In some embodiments, the LCK protein may be linked to an FKBP protein (e.g., a modified FKPB, e.g., an FKPB that undergoes inducible binding to an FRB domain in the presence of (e.g., provision of) an additional molecule, such as the small molecule AP201967 and/or a functional analog thereof (e.g., AP20187). In some embodiments, a composition of the present invention is a vector. In some embodiments, the composition(s) comprise one or more nucleic acid molecules and/or vectors.

Further provided herein is a vector comprising one or more (e.g., 1, 2, 3, 4, 5, 6, 7, 8, 9, 10) nucleic acid molecules and/or compositions of this invention. In some embodiments, a vector of the present invention may comprise a nucleic acid molecule encoding a CAR of the present invention. In some embodiments, a vector of the present invention may comprise a nucleic acid molecule encoding a polypeptide of the present invention. In some embodiments, a vector of the present invention may comprise a nucleic acid molecule encoding a CAR of the present invention and/or a nucleic acid molecule encoding a polypeptide of the present invention. In some embodiments of the present invention, a nucleic acid may encode a CAR of the present invention and a polypeptide of the present invention (e.g., a polypeptide encoding an FKBP linked to SHP1).

In some embodiments, the present invention further provides a cell comprising one or more (e.g., 1, 2, 3, 4, 5, 6, 7, 8, 9, 10) CAR, nucleic acid molecule, polypeptide, vector, and/or composition of this invention. In some embodiments, the present invention provides a cell comprising one or more nucleic acid molecules of this invention. In some embodiments, a cell of the present invention may comprise a vector comprising a nucleic acid molecule encoding the CAR of the present invention, and a second vector comprising a nucleic acid molecule encoding a polypeptide an FKBP (e.g., a modified FKBP) linked to SHP1.

In some embodiments, a cell of the present invention may comprise: a composition comprising a CAR comprising a 4-1BB costimulatory molecule; and a composition comprising an LCK protein (e.g., an exogenous LCK). In some embodiments, a composition comprising an LCK protein may be a nucleic acid molecule comprising an LCK open reading frame, and/or a vector and/or composition comprising the same.

A cell of the present invention may be any type of cell, e.g., an immune cell. In some embodiments, the cell is selected from the group consisting of a $\alpha\beta$T cell, a natural killer (NK) cell, a cytotoxic T lymphocyte (CTL), a regulatory T cell, a natural killer T (NKT) cell, a Th17 cell, a $\gamma\delta$T cell and any combination thereof.

In some embodiments of the present invention, the CAR, nucleic acid molecule, polypeptide, vector, composition, and/or cell of the present invention may comprise further components and or moieties. For example, the CAR, nucleic acid molecule, polypeptide, vector and/or composition may further comprise a detectable moiety. Non-limiting examples of a detectable moiety include a HA-tag and/or a FLAG-tag.

In some embodiments of the present invention, the CAR, nucleic acid molecule, polypeptide, vector, composition, and/or cell of the present invention may further comprise one or more (e.g., 1, 2, 3, 4, 5, 6, 7, 8, 9, 10) effector molecules. Non-limiting examples of an effector molecule include a drug, a toxin, a small molecule, an antibody, a cytokine, an oncolytic virus, an enzyme, a nanoparticle, a biomaterial, a scaffold and any combination thereof.

Methods

The present invention also provides methods employing the CAR, nucleic acid molecule, polypeptide, vector, composition, and/or cell of this invention. Thus, in some embodiments, the present invention provides a method of reducing a T cell-mediated immune stimulation to a target cell (e.g., scFv-binding target expressing target cell) population or tissue in a subject, comprising administering to the subject an effective amount of a cell comprising a CAR of the present invention and a FKBP linked to SHP1 (e.g., a polypeptide and/or a nucleic acid molecule, vector, and/or composition encoding said polypeptide) of the present invention, and administering an effective amount of AP21967 and/or functional analogue thereof (e.g., AP20187), wherein the AP21967 and/or functional analogue thereof dimerizes the CAR and the polypeptide, thereby reducing the T cell-mediated immune stimulation. Administration of an effective amount of AP21976 and/or functional analogue thereof may be concurrent with, prior to, and/or following (e.g., afterward) administration of the cell of the present invention.

A target cell and/or target tissue of the methods herein may be any cell and/or tissue expressing a binding target of an scFv of a CAR of the present invention. scFv targets (i.e., scFv binding targets) may also include proteins expressed on healthy tissues and/or cells such as immune-related antigens, e.g., in order to identify and/or modulate native host responses. Non-limiting examples of scFv targets include wherein the scFv binds to TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-β, SSEA-4, CD20, FRα, ERBB2(Her2/neu), MUC1, EGFR, NCAM, Prostase, PAP, ELF2M, EphB2, IGF-I receptor, CAIX, LMP2, gp100, bcr-abl, tyrosinase, EphA2, GM1, sLe, GM3, TGSS, HMWMAA, FR(3, TEM1/CD248, TEM7R, CLDN6, GPRCSD, CXORF61, CD97, CD179a, ALK, PSA, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6,E7, MAGE A1, ETV6-AML, Sp17, XAGE1, Tie 2, MAD-CT-1, MAD-CT-2, FRA1, p53, p53 mutants, prostein, survivin, PCTA-1/Galectin8, MelanA/MART1, Ras, hTERT, ML-IAP, ERG (i.e., TMPRSS2 ETS fusion gene), NA17, PAX3, AR, cyclin B1, MYCN, RhoC, TRP-2, CYP1B1, BORIS, SART3, PAX5, OY-TES1, LCK, AKAP-4, SSX2, RAGE-1, RU1, RU2, CEA, hsp70-2, CD79a, CD79b, CD72, LAIR1, FCAR, LILRA2, CD300LF, CLEC12A, BST2, EMR2, LY75, GPC3, CLN18.2, CLN6, FCRL5, IGLL1, or any variant thereof. In certain aspects, cytokine exodomains or other ligand/receptor molecules as exodomains may provide targeting to the tumor cells.

In some embodiments, the present invention provides a method of reducing CAR T cell-mediated immune stimulation bystander cytotoxicity in a subject having cancer, comprising: a) administering to the subject an effective amount of a cell comprising a CAR of the present invention and a FKBP linked to SHP1 (e.g., a polypeptide and/or a nucleic acid molecule, vector, and/or composition encoding said polypeptide) of the present invention, and administering an effective amount of AP21967 and/or functional analogue thereof (e.g., AP20187), wherein said cells induce an unacceptable level of bystander cytotoxicity; and b) administering (e.g., concurrently with, prior to, and/or afterward) an effective amount of AP21967 and/or functional analogue thereof (e.g., AP20187), wherein the AP21967 and/or functional analogue thereof dimerizes the CAR and the polypeptide, thereby reducing the CAR T cell-mediated immune stimulation and bystander cytotoxicity.

In some embodiments, the present invention provides a method of enhancing T cell-mediated immune stimulation to a target cell (e.g., scFv binding-target expressing target cell) population or tissue in a subject, comprising administering to the subject an effective amount of a cell comprising a CAR comprising a 4-1BB costimulatory molecule and a composition comprising an LCK protein (e.g., an exogenous LCK, e.g., a nucleic acid molecule comprising an LCK open reading frame, and/or a vector and/or composition comprising the same), wherein the exogenous LCK is overexpressed in the cell as compared to wildtype LCK, thereby enhancing the T cell-mediated immune stimulation.

In some embodiments, the present invention provides a method of enhancing T cell-mediated immune stimulation to a target cell (e.g., an scFv-target expressing target cell) population or tissue in a subject, comprising administering to the subject an effective amount of a cell comprising a CAR comprising a 4-1BB costimulatory molecule and an exogenous LCK protein, wherein the exogenous LCK is overexpressed in the cell as compared to wildtype LCK, thereby enhancing the T cell-mediated immune stimulation.

In some embodiments, the present invention provides a method of stimulating a T cell-mediated immune response to a target cell (e.g., an scFv-target expressing target cell) population or tissue in a subject, comprising administering to the subject an effective amount of a cell of the present invention, thereby stimulating a T cell-mediated immune response to the target cell population or tissue in the subject. The cell may comprise any of the compositions of the present invention. For example, in some embodiments, the cell may comprise a CAR of the present invention (e.g., a CAR comprising a CD28 costimulatory molecule) comprising an FRB domain, and a polypeptide comprising an FKBP linked to SHP1, and/or one or more vector, composition, and/or nucleic acid molecule encoding the same). In some embodiments, the cell may comprise a CAR comprising a 4-1BB costimulatory molecule, and an exogenous LCK protein.

In some embodiments, the present invention provides a method of treating a subject having a disease or disorder associated with elevated expression of a target antigen (e.g., scFv target) by a cell of the subject, comprising administering to the subject an effective amount of a cell of the present invention, thereby treating the subject having the disease or disorder associated with elevated expression of the target antigen by the cell of the subject. The cell may comprise any of the compositions of the present invention. For example, in some embodiments, the cell may comprise a CAR of the present invention (e.g., a CAR comprising a CD28 costimulatory molecule) comprising an FRB domain, and a polypeptide comprising an FKBP linked to SHP1, and/or one or more vector, composition, and/or nucleic acid molecule encoding the same). In some embodiments, the cell may comprise a CAR comprising a 4-1BB costimulatory molecule, and an exogenous LCK protein.

In some embodiments, the present invention provides a method of generating a population of genetically engineered cells in a subject, comprising administering to the subject a cell genetically engineered to express a CAR of the present invention, wherein the population of genetically engineered cells persists in the subject for a period of time following administration.

In some embodiments, the present invention provides a method of generating a population of genetically engineered cells in a subject, comprising administering to the subject a cell of the present invention, wherein the cell expands into and persists as a population of genetically engineered cells in the subject for a period of time following administration. The cell may comprise any of the compositions of the present invention. For example, in some embodiments, the cell may comprise a CAR of the present invention (e.g., a CAR comprising a CD28 costimulatory molecule) comprising an FRB domain, and a polypeptide comprising an FKBP linked to SHP1, and/or one or more vector, composition, and/or nucleic acid molecule encoding the same). In some embodiments, the cell may comprise a CAR comprising a 4-1BB costimulatory molecule, and an exogenous LCK protein.

In some embodiments, the present invention provides a method of expanding a population of genetically engineered cells in a subject, comprising administering to the subject a cell genetically engineered to express a CAR of the present invention, wherein the administered genetically engineered cell produces a population of progeny cells in the subject.

In some embodiments, the present invention provides a method of expanding a population of genetically engineered cells in a subject, comprising administering to the subject a cell of the present invention, wherein the cell produces a population of progeny cells in the subject. The cell may comprise any of the compositions of the present invention. For example, in some embodiments, the cell may comprise a CAR of the present invention (e.g., a CAR comprising a CD28 costimulatory molecule) comprising an FRB domain, and a polypeptide comprising an FKBP linked to SHP1, and/or one or more vector, composition, and/or nucleic acid molecule encoding the same). In some embodiments, the cell may comprise a CAR comprising a 4-1BB costimulatory molecule, and an exogenous LCK protein.

In some embodiments, the present invention provides a method of treating cancer in a subject, comprising administering to the subject an effective amount of a cell of the present invention, thereby treating cancer in the subject. The cell may comprise any of the compositions of the present invention. For example, in some embodiments, the cell may comprise a CAR of the present invention (e.g., a CAR comprising a CD28 costimulatory molecule) comprising an FRB domain, and a polypeptide comprising an FKBP linked to SHP1, and/or one or more vector, composition, and/or nucleic acid molecule encoding the same). In some embodiments, the cell may comprise a CAR comprising a 4-1BB costimulatory molecule, and an exogenous LCK protein.

In some embodiments, the present invention provides a method of targeting a cancer cell and/or a cancer initiating cell (CIC) having a target antigen (e.g., scFv target antigen), comprising providing to the cancer cell and/or the CIC a cell comprising a CAR of the present invention. In some embodiments, the cancer cell and/or CIC may be in vitro and/or in vivo.

In some embodiments, the present invention provides a method of targeting a cancer cell and/or a cancer initiating cell (CIC) having a target antigen (e.g., scFv target antigen), comprising providing to the cancer cell and/or the CIC a cell of the present invention. The cell may comprise any of the compositions of the present invention. For example, in some embodiments, the cell may comprise a CAR of the present invention (e.g., a CAR comprising a CD28 costimulatory molecule) comprising an FRB domain, and a polypeptide comprising an FKBP linked to SHP1, and/or one or more vector, composition, and/or nucleic acid molecule encoding the same). In some embodiments, the cell may comprise a CAR comprising a 4-1BB costimulatory molecule, and an exogenous LCK protein. In some embodiments, the cancer cell and/or CIC may be in vitro and/or in vivo.

In some embodiments, the present invention provides a method of detecting cancer cells and/or cancer initiating cells (CICs) in a cell sample, comprising: a) contacting the cell sample with a CAR of the present invention under conditions whereby a binding complex can form; and b) detecting formation of the binding complex, wherein detection of the binding complex is indicative of cancer cells and/or CICs in the cell sample.

In some embodiments, the present invention provides a method of detecting cancer cells and/or cancer initiating cells (CICs) in a subject, comprising: a) contacting a cell sample obtained from the subject with a CAR of the present invention under conditions whereby a binding complex can form; and b) detecting formation of the binding complex, wherein detection of the binding complex is indicative of the presence of cancer cells and/or CICs in the subject.

In some embodiments, the present invention provides a method of stimulating a T cell-mediated immune response to a target cell (e.g., scFv-target expressing target cell) population or tissue in a subject, comprising administering to the subject an effective amount of a CAR composition selected from the group consisting of: a) a CAR composition comprising: a CAR comprising a hinge region, a transmembrane domain, a CD3ζ domain, an scFv, a CD28 costimulatory molecule, and an FRB; b) a CAR composition comprising: (i) a CAR comprising a hinge region, a transmembrane domain, a CD3ζ domain, an scFv, a CD28 costimulatory molecule, and an FRB; and (ii) a polypeptide comprising an FKBP linked to SHP1; c) a CAR composition comprising: (i) a CAR comprising a 4-1BB costimulatory molecule; and (ii) an LCK protein (e.g., an exogenous LCK protein); d) a CAR composition comprising: (i) a CAR comprising a hinge region, a transmembrane domain, a CD3ζ domain, an scFv, a CD28 costimulatory molecule, and an FRB; (ii) a CAR comprising a 4-1BB costimulatory molecule; and (iii) an LCK protein (e.g., an exogenous LCK protein); e) a CAR composition comprising: (i) a CAR comprising a hinge region, a transmembrane domain, a CD3ζ domain, an scFv, a CD28 costimulatory molecule, and an FRB; (ii) a polypeptide comprising an FKBP linked to SHP1; (iii) a CAR comprising a 4-1BB costimulatory molecule; and (iv) an LCK protein (e.g., an exogenous LCK protein); thereby stimulating a T cell-mediated immune response to the target expressing target cell population or tissue in the subject.

In some embodiments, the present invention provides a method of treating a subject having a disease or disorder associated with elevated expression of a target antigen (e.g., scFv target) by a cell of the subject, comprising administering to the subject an effective amount of a CAR composition selected from the group consisting of: a) a CAR composition comprising: a CAR comprising a hinge region, a transmembrane domain, a CD3ζ domain, an scFv, a CD28 costimulatory molecule, and an FRB; b) a CAR composition comprising: (i) a CAR comprising a hinge region, a transmembrane domain, a CD3ζ domain, an scFv, a CD28 costimulatory molecule, and an FRB; and (ii) a polypeptide comprising an FKBP linked to SHP1; c) a CAR composition comprising: (i) a CAR comprising a 4-1BB costimulatory molecule; and (ii) an LCK protein (e.g., an exogenous LCK protein); d) a CAR composition comprising: (i) a CAR comprising a hinge region, a transmembrane domain, a CD3ζ domain, an scFv, a CD28 costimulatory molecule, and an FRB; (ii) a CAR comprising a 4-1BB costimulatory molecule; and (iii) an LCK protein (e.g., an exogenous LCK protein); e) a CAR composition comprising: (i) a CAR comprising a hinge region, a transmembrane domain, a CD3ζ domain, an scFv, a CD28 costimulatory molecule, and an FRB; (ii) a polypeptide comprising an FKBP linked to SHP1; (iii) a CAR comprising a 4-1BB costimulatory molecule; and (iv) an LCK protein (e.g., an exogenous LCK protein); thereby treating the subject having the disease or disorder associated with elevated expression of the target antigen by the cell of the subject.

For administration in the methods of use described above, the active agent (e.g., the CAR, polypeptide, cell, nucleic acid molecule and/or vector of this invention) will generally be mixed, prior to administration, with a non-toxic, pharmaceutically acceptable carrier substance (e.g., normal saline or phosphate-buffered saline), and will be administered using any medically appropriate procedure, e.g., parenteral administration (e.g., injection) such as by intravenous or intra-arterial injection.

The active agents described above may be formulated for administration in a pharmaceutical carrier in accordance with known techniques. See, e.g., Remington, *The Science*

*And Practice of Pharmacy* (latest edition). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the subject. The carrier may be a liquid and is preferably formulated with the compound as a unit-dose formulation which may contain from 0.01 or 0.5% to 95% or 99% by weight of the active compound. The carrier may be sterile or otherwise free from contaminants that would be undesirable to administer or deliver to a subject.

Formulations of the present invention suitable for parenteral administration comprise sterile aqueous and non-aqueous injection solutions of the active compound, which preparations are preferably isotonic with the blood of the intended subject. These preparations may contain anti-oxidants, buffers, bacteriostats and solutes which render the formulation isotonic with the blood of the intended subject.

The active agents may be administered by any medically appropriate procedure, e.g., normal intravenous or intra-arterial administration. In certain cases, direct administration to a tumor and/or a body cavity, orifice and/or tissue containing a tumor may be desired.

Active agents may be provided in lyophilized form in a sterile aseptic container or may be provided in a pharmaceutical formulation in combination with a pharmaceutically acceptable carrier, such as sterile pyrogen-free water or sterile pyrogen-free physiological saline solution.

CAR-modified T cells of this invention may also serve as a type of vaccine for ex vivo immunization and/or in vivo therapy in a subject of this invention.

In some embodiments involving ex vivo immunization, at least one of the following occurs in vitro prior to administering the cell into a subject: i) expansion of the cells, ii) introducing a nucleic acid encoding a CAR of this invention to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR, polypeptide, and/or nucleic acid molecule of this invention. The resulting CAR-modified cell can be administered to a subject of this invention to provide a therapeutic benefit. In some embodiments, the subject can be a human and the CAR-modified cell can be autologous with respect to the subject who is the recipient of the CAR-modified cells. Alternatively, the cells can be allogeneic, syngeneic or xenogeneic with respect to the subject who is the recipient of the CAR-modified cells.

In addition to using a cell-based vaccine for ex vivo immunization, the present invention also provides compositions and methods for in vivo immunization to elicit and/or enhance an immune response directed against an antigen in a subject of this invention.

Generally, the cells activated and expanded as described herein can be used in the treatment and/or prevention of diseases and/or disorders that arise in subjects; e.g., subjects who are immunocompromised or at risking of becoming immunocompromised.

CAR-modified T cells of the present invention may be administered either alone, or as a pharmaceutical composition in combination with diluents and/or with other components such as IL-2 and/or other cytokines and/or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline, sterile saline and the like; carbohydrates such as glucose, mannose, sucrose or dextrans, mannitol; proteins; polypeptides or amino acids such as glycine; antioxidants; chelating agents such as EDTA and/or glutathione; adjuvants (e.g., aluminum hydroxide) and/or preservatives, singly or in any combination.

Pharmaceutical compositions of the present invention can be administered in a manner appropriate to the disease to be treated and/or prevented. The quantity and frequency of administration will be determined by such factors as the condition of the subject, as well as the type and severity of the subject's disease, although in some embodiments, appropriate dosages may be determined by clinical trials.

When "an immunologically effective amount," "an anti-tumor effective amount," "a tumor-inhibiting effective amount," or a "therapeutic amount" is indicated, the precise amount of the compositions of the present invention to be administered can be determined by a physician with consideration of individual differences in age, weight, tumor size, extent of infection or metastasis, and condition of the patient (subject). In some embodiments, a pharmaceutical composition comprising cells of this invention can be administered at a dosage of about $10^3$ to about $10^{10}$ cells/kg body weight, and in some embodiments, the dosage can be from about $10^5$ to about $10^6$ cells/kg body weight, including all integer values (e.g., $10^4$, $10^5$, $10^6$, $10^7$, $10^8$, $10^9$) within those ranges.

The cell compositions of this invention can also be administered multiple times (e.g., hourly, four times daily, three times daily, two times daily, daily, twice weekly, three times weekly, weekly, monthly, bi-monthly, semi-annually, annually, etc.) at these dosages.

The cells of this invention can be administered by using infusion techniques that are commonly known in immunotherapy (see, e.g., Rosenberg et al. *New Eng. J. of Med.* 319:1676 (1988)). The optimal dosage and treatment regimen for a particular subject can readily be determined by one skilled in the art of medicine by monitoring the subject for signs of disease and adjusting the treatment accordingly.

In some embodiments, it may be desirable to administer activated T cells to a subject and then subsequently redraw blood (or have an apheresis performed), activate T cells therefrom as described herein, and reinfuse the subject with these activated and expanded T cells. This process can be carried out multiple times, e.g., weekly or every few weeks. In certain embodiments, T cells can be activated from blood draws of from about 10 cc to about 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

Administration of the compositions of this invention can be carried out in any manner, including by aerosol inhalation, injection, ingestion, transfusion, implantation and/or transplantation. The compositions of this invention can be administered to a patient subcutaneously, intradermally, intratumorally, intranodally, intramedullary, intramuscularly, by intravenous (i.v.) injection, and/or intraperitoneally. In some embodiments, the cell compositions of the present invention can be administered to a subject by intradermal or subcutaneous injection. In another embodiment, the cell compositions of the present invention can be administered by i.v. injection. In some embodiments, the compositions of cells can be injected directly into a tumor, lymph node and/or site of infection.

In some embodiments of the present invention, cells activated and expanded using the methods described herein, or other methods known in the art where cells are expanded to therapeutic levels, can be administered to a subject in conjunction with (e.g., before, concurrently and/or following) any number of relevant treatment modalities.

In some embodiments, the cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytotoxin, fludaribine, cyclosporin, FK506, rapamycin, mycophenolic acid, steroids, FR901228, cytokines, and/o irradiation.

In some embodiments, the cell compositions of the present invention can be administered to a patient in conjunction with (e.g., before, concurrently and/or following) bone marrow transplantation, T cell ablative therapy using either chemotherapy agents such as fludarabine, external-beam radiation therapy (XRT), cyclophosphamide, or antibodies such as OKT3 or alemtuzumab. In another embodiment, the cell compositions of the present invention can be administered following B-cell ablative therapy such as agents that react with CD20, e.g., rituximab. For example, in one embodiment, subjects may undergo standard treatment with high dose chemotherapy followed by peripheral blood stem cell transplantation. In certain embodiments, following the transplant, subjects can receive an infusion of the expanded immune cells of the present invention. In an additional embodiment, expanded cells can be administered before and/or following surgery.

In the treatment of cancers or tumors the CARs, nucleic acid molecules, polypeptides, and/or vectors of the present invention may optionally be administered in conjunction with other, different, cytotoxic agents such as chemotherapeutic or antineoplastic compounds or radiation therapy useful in the treatment of the disorders or conditions described herein (e.g., chemotherapeutics or antineoplastic compounds). The other compounds may be administered prior to, concurrently and/or after administration of the antibodies or antigen binding fragments thereof of this invention. As used herein, the word "concurrently" means sufficiently close in time to produce a combined effect (that is, concurrently may be simultaneously, or it may be two or more administrations occurring before or after each other)

As used herein, the phrase "radiation therapy" includes, but is not limited to, x-rays or gamma rays which are delivered from either an externally applied source such as a beam or by implantation of small radioactive sources.

Nonlimiting examples of suitable chemotherapeutic agents which may be administered with the antibodies or antigen binding fragments, cells, nucleic acid molecules and/or vectors as described herein include daunomycin, cisplatin, verapamil, cytosine arabinoside, aminopterin, democolcine, tamoxifen, Actinomycin D, Alkylating agents (including, without limitation, nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide; Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine, Natural products and their derivatives (for example, vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, Ara-C, paclitaxel (paclitaxel is commercially available as Taxol®), Mithramycin, Deoxyco-formycin, Mitomycin-C, L-Asparaginase, Interferons (especially IFN-a), Etoposide, and Teniposide; Other anti-proliferative cytotoxic agents are navelbene, CPT-11, anastrazole, letrazole, capecitabine, reloxafine, cyclophosphamide, ifosamide, and droloxafine. Additional anti-proliferative cytotoxic agents include, but are not limited to, melphalan, hexamethyl melamine, thiotepa, cytarabin, idatrexate, trimetrexate, dacarbazine, L-asparaginase, camptothecin, topotecan, bicalutamide, flutamide, leuprolide, pyridobenzoindole derivatives, interferons, and interleukins. Preferred classes of antiproliferative cytotoxic agents are the EGFR inhibitors, Her-2 inhibitors, CDK inhibitors, and Herceptin® (trastuzumab). (see, e.g., U.S. Pat. No. 6,537,988; U.S. Pat. No. 6,420,377). Such compounds may be given in accordance with techniques currently known for the administration thereof.

Examples of techniques which can be used to produce single-chain Fvs (scFv) and antibodies include those described in U.S. Pat. Nos. 4,946,778 and 5,258,498; Huston et al. *Methods in Enzymology* 203:46-88 (1991); Shu et al. PNAS 90:7995-7999 (1993); and Skerra et al. *Science* 240:1038-1040 (1988).

The invention further provides polynucleotides comprising a nucleotide sequence encoding a chimeric antigen receptor of the invention as described above. The polynucleotides may be obtained, and the nucleotide sequence of the polynucleotides determined, by any method known in the art. For example, if the nucleotide sequence of the components of the chimeric antigen receptor are known, a polynucleotide encoding the components may be assembled from chemically synthesized oligonucleotides, which involves the synthesis of overlapping oligonucleotides containing portions of the sequence encoding the components of the chimeric antigen receptor, annealing and ligation of those oligonucleotides, and then amplification of the ligated oligonucleotides by polymerase chain reaction (PCR). Alternatively, a polynucleotide encoding a chimeric antigen receptor may be generated from nucleic acid from a suitable source. Amplified nucleic acids generated by PCR may then be cloned into replicable cloning vectors using any method well known in the art.

The present invention is explained in greater detail in the following non-limiting examples. The following examples are presented in order to more fully illustrate the preferred embodiments of the invention. They should in no way, however, be construed as limiting the broad scope of the invention.

Examples

Example 1: THEMIS-SHP1 Recruitment by 4-1BB Tunes LCK-Mediated Priming of CAR-Redirected T Cells Chimeric antigen receptors (CAR) expressed by T cells recognize tumor cells via single chain antibodies and activate T cell cytotoxic machinery and costimulation. In clinical studies, costimulation mediated by CD28 and 4-1BB endodomains integrated into the CD19-specific CAR has been shown to be essential in causing tumor regression. CD28 and 4-1BB costimulation differentially modulates the kinetics, metabolism and persistence of CAR-T cells, but the mechanisms governing these differences are not fully understood. In this study, it was discovered that LCK is recruited into the immunological synapse of the CD28 encoding CAR by co-receptors, leading to increased antigen-independent CAR-CD3ζ phosphorylation and antigen-dependent T cell activation. In contrast, the synapse formed by the 4-1BB encoding CAR recruits the THEMIS-SHP1 phosphatase complex that attenuates CAR-CD3ζ phosphorylation and T cell activation. This study further shows that the CAR synapse can be engineered to recruit either LCK to enhance the kinetic of tumor killing of 4-1BB costimulated CAR-T cells or SHP1 to tune down the cytokine release of CD28 costimulated CAR-T cells.

Figure 1B:
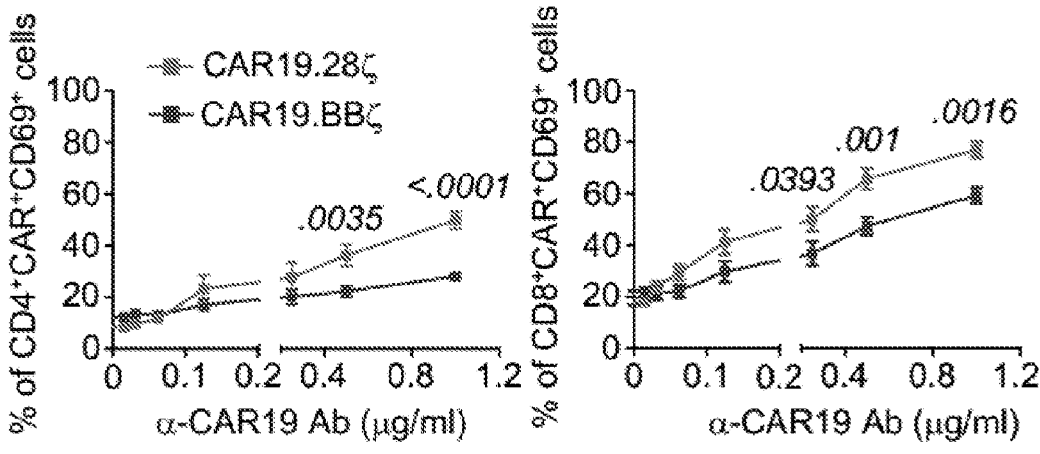
Figure 1C:
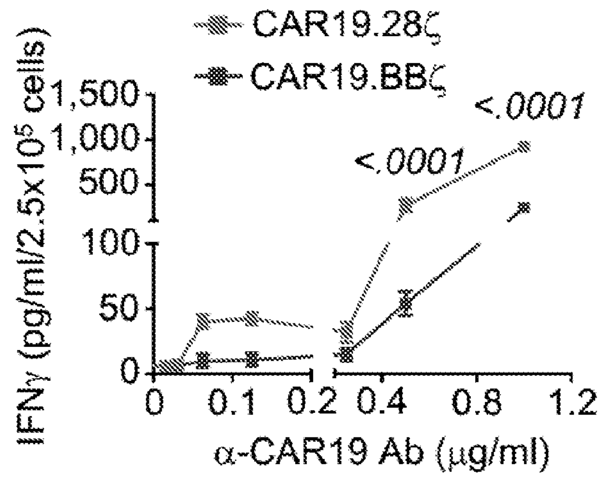
Figure 1D:
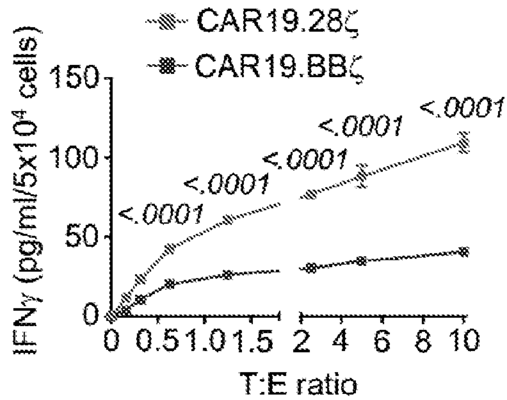
Figure 1E:
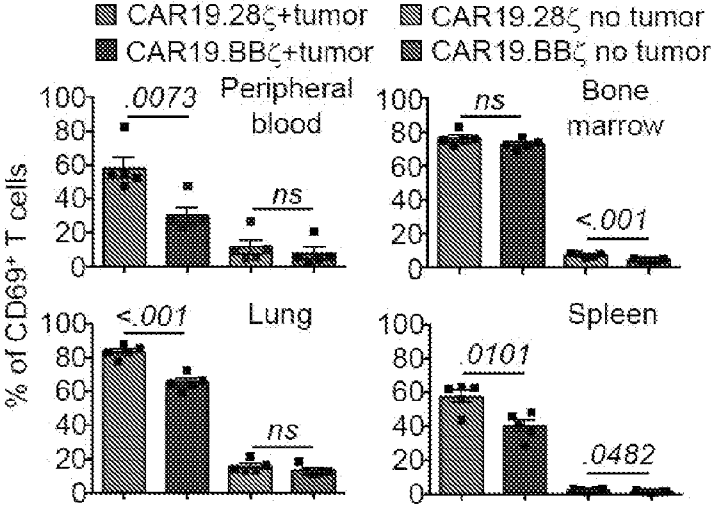
Figure 1F:
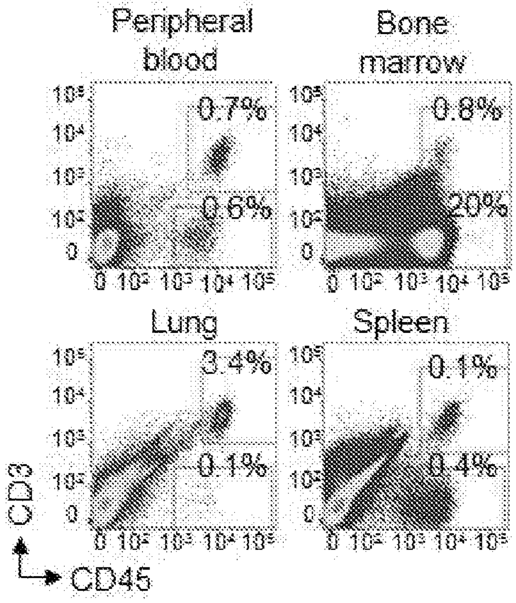

CD28 costimulation promotes higher activation of CAR-T cells via LCK-mediated constitutive phosphorylation of the CAR-CD3c domain. To stringently compare the CD28 and 4-1BB proximal signaling in CAR-T cells, two CARs were generated that encode the same CD19-specific scFv and CD8α stalk, and either the CD28 or the 4-1BB intracytoplasmic co-stimulatory domain followed by the intracytoplasmic tail of the CD3 chain (CAR19.28ζ and CAR19.BBζ). Upon activation, transduction and expansion of CAR-T cells for 10-14 days following clinically validated standard operating procedures, the magnitude of CAR19.28ζ-T and CAR19.BBζ-T cell activation was measured by stimulating them with titrated doses of an anti-idiotype Ab (anti-CAR19 Ab) that crosslinks the CAR. CAR19.28ζ-T cells showed a significantly higher magnitude of activation than CAR19.BBζ-T cells as measured by Ca 2+ influx (FIG. 1A) and higher expression of the early T cell activation marker CD69 in both $CD4^+$ and $CD8^+$ T cells (FIG. 1B). Accordingly, CAR19.28ζ-T cells released more IFNγ than CAR19.BBζ-T cells (FIG. 1C). In contrast, no significant differences in the expression of activation markers and cytokine release were observed when CAR19.28ζ-T and CAR19.BBζ-T cells were stimulated via T-cell-receptor (TCR) crosslinking, indicating that the costimulation associated with the CAR determines the magnitude of activation upon CAR engagement. Similar results were obtained when CAR19.28ζ-T and CAR19.BBζ-T cells were simulated via titration of tumor cells expressing the target antigen (FIG. 1D). To confirm the results in vivo, CAR19.28ζ-T and CAR19.BBζ-T cells were differentially labeled and infused simultaneously in NSG (NOD-scid $IL2Rg^{null}$) mice bearing $CD19^+$ tumor cells. T cells were then harvested six hours after infusion. Tumor cells ($CD45^+CD3^-$) and T cells ($CD45^+CD3^+$) were detected in the peripheral blood, bone marrow, lung, and spleen by flow cytometry. Gating on $CD45^+CD3^+$ T cells and differentially labeled cells, CAR19.28ζ-T cells showed higher expression of CD69 than CAR19.BBζ-T cells in organs that contained less tumor cells such as blood, lung and spleen (FIGS. 1E-1F). The stronger activation of CAR19.28ζ-T cells translated into a more pronounced short-term antitumor activity as compared to CAR19.BBζ-T cells when low doses of CAR-T cells were used.

Figure 1G:
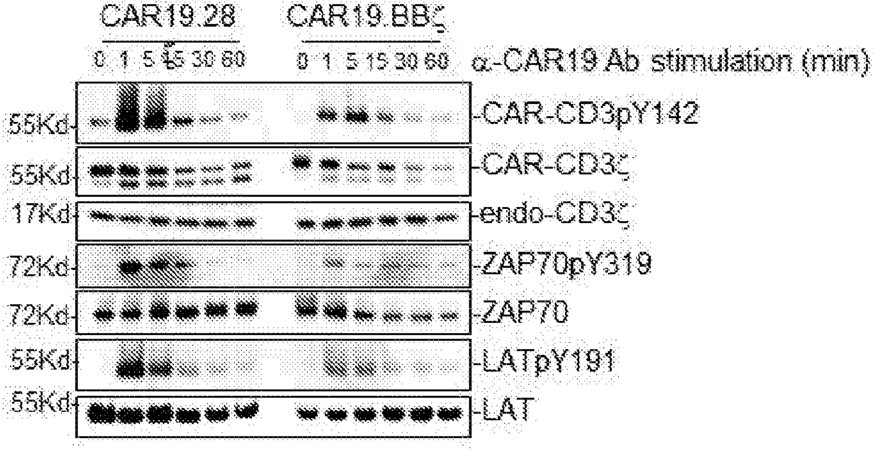
Figure 1H:
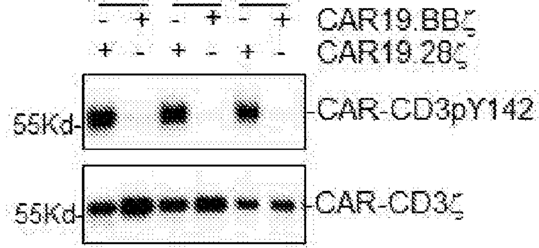
Figure 1I:
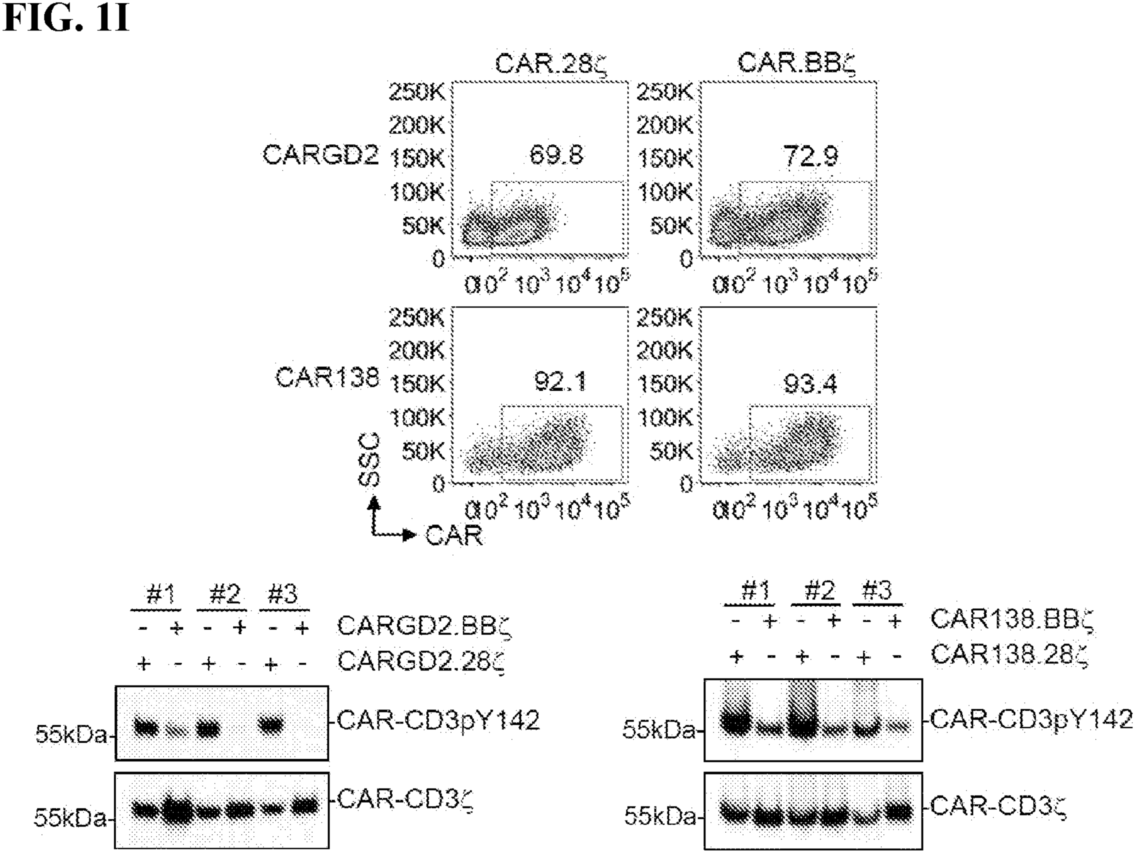
Figure 1J:
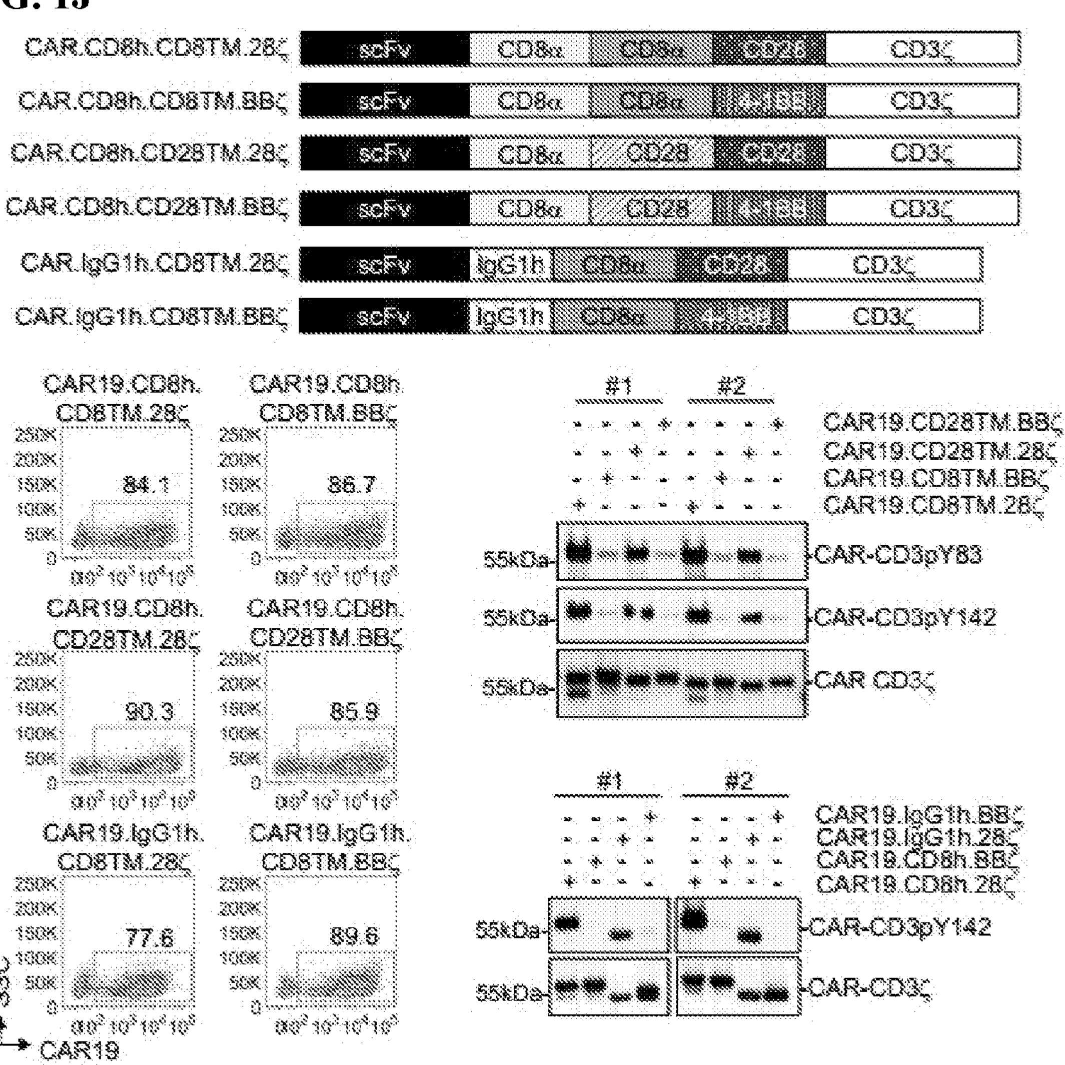

Proximal signaling molecules are rapidly phosphorylated upon TCR activation in T cells. This study observed that CAR19.28ζ-T cells exhibited higher phosphorylation of the downstream proximal signaling molecules CAR-CD3ζ, ZAP70 and LAT when stimulated with the anti-CAR19 Ab as compared to CAR19.BBζ-T cells (FIG. 1G), and CAR19.28ζ-T cells consistently showed higher antigen-independent/basal phosphorylation of the CAR-CD3 (FIG. 1H and Table 1). The latter effect was observed with two other CARs encoding the CD28 endodomain (FIG. 1I), and regardless of the type of hinge or transmembrane domain used within the CAR19 constructs (FIG. 1J). Furthermore, both $CD4^+$ and $CD8^+$ T cells growing with different cytokines (IL-7, IL-15, or IL-2) showed higher basal phosphorylation of CAR-CD3ζ in the CAR encoding the CD28 endodomain.

Figure 2A:
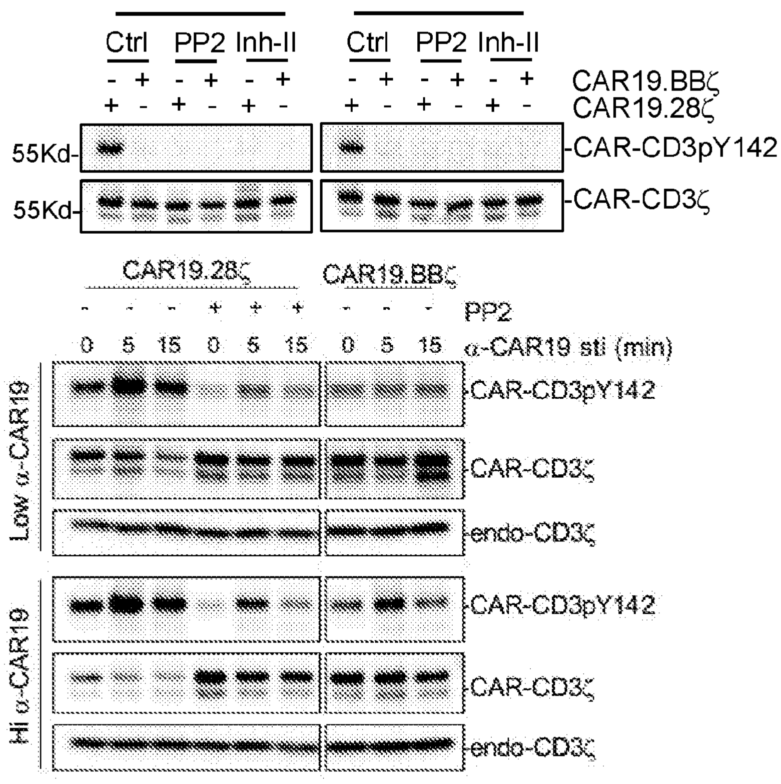
Figure 2B:
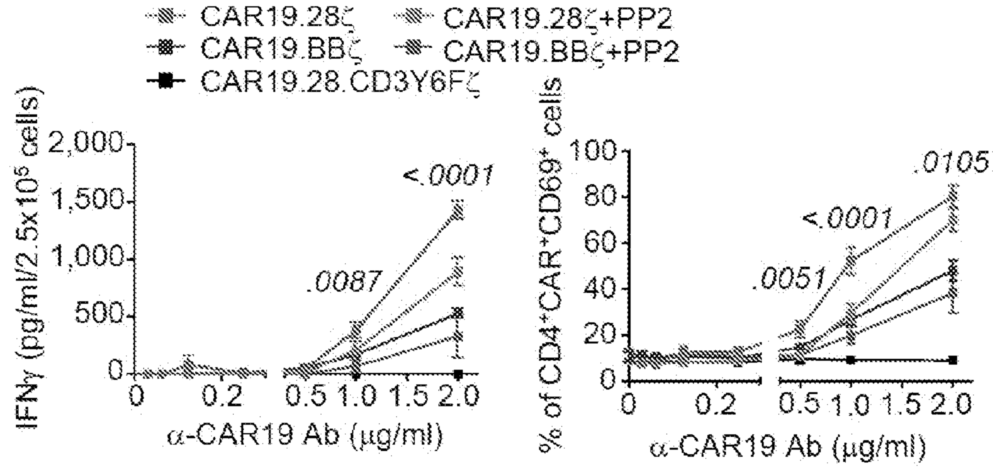

LCK kinase confers more profound phosphorylation events in CAR19.28ζ-T cells as compared with CAR19.BBζ-T cells. We observed that the CAR-CD3ζ basal phosphorylation of CAR19.28ζ-T cells was abrogated by the addition of Src family kinase (PP2) or LCK inhibitor (Inh-II) (FIG. 2A). Furthermore, pretreatment of CAR19.28ζ-T cells with PP2, which significantly decreases the CAR-CD3ζ basal phosphorylation, reduced their responsiveness to CAR crosslinking with low doses of anti-CAR19 antibody to similar levels of CAR19.BBζ-T cells as shown by the expression of CD69 and release of IFNγ and IL-2 (FIG. 2B). In contrast, high doses of anti-CAR19 antibody partially overcame the PP2-mediated inhibition in CAR19.28ζ-T cells. This suggests that LCK is rapidly recruited in the CAR19.28ζ synapse and that a strong CAR aggregation mediated by high doses of anti-CAR19 antibody rapidly overcomes the inhibitory effects of PP2 pretreatment. Collectively, these data indicate that higher CAR-CD3 basal phosphorylation primes CAR19.28ζ-T cells to a higher magnitude of activity in response to low antigen stimulation.

Figure 2C:
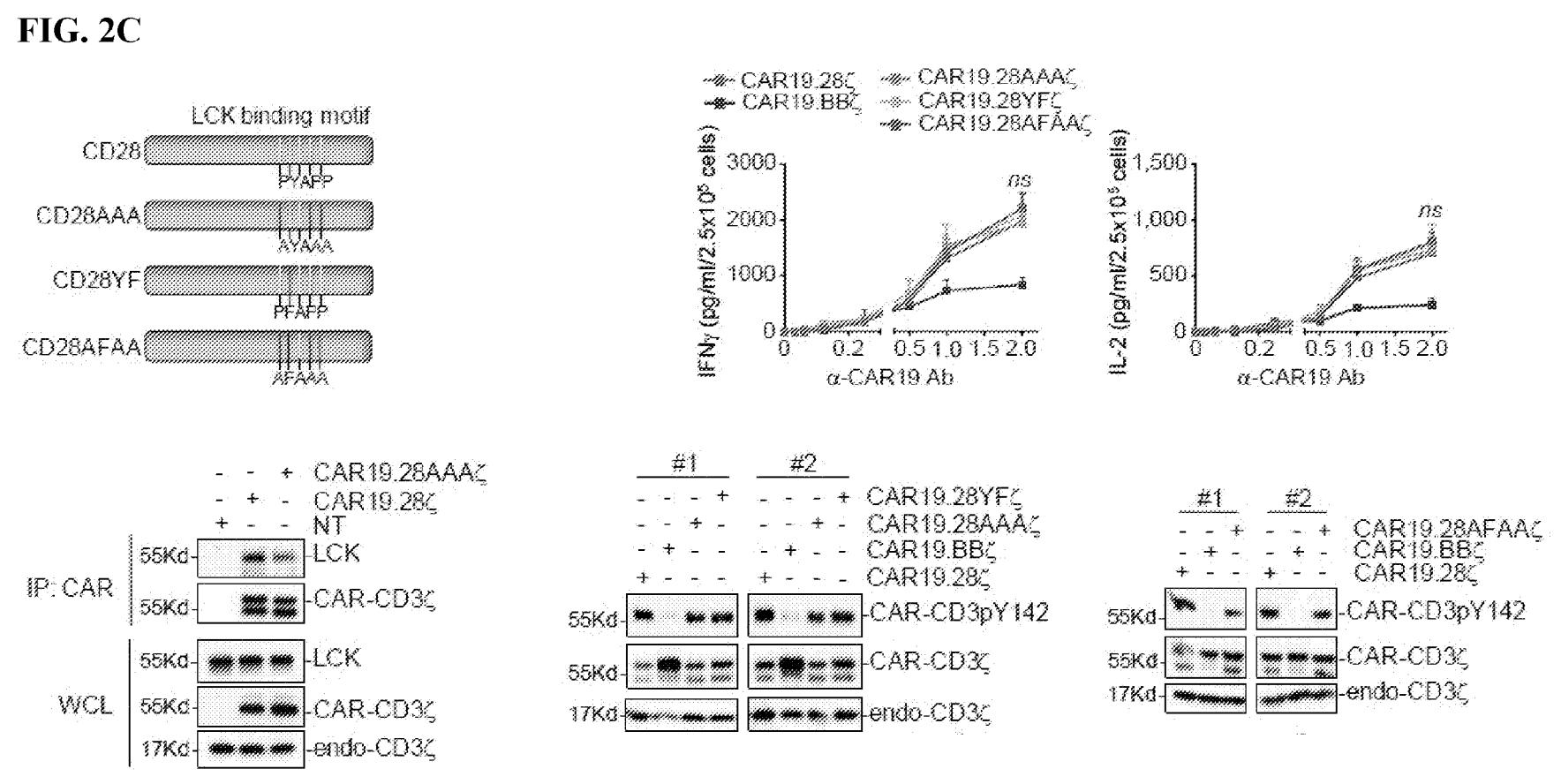
Figure 2D:
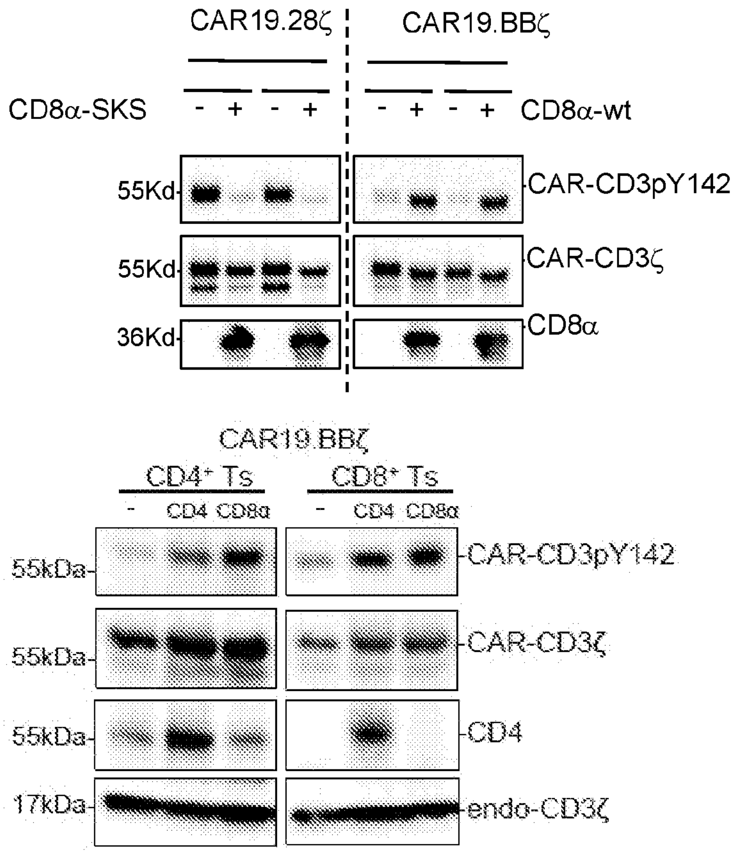

Co-receptors recruits LCK within the CAR synapse. LCK binds to the PYAPP motif of CD28. However, this study observed that introduction of loss-of-function mutations to the PYAPP motif of CAR19.28ζ (CAR19.28AAAζ, CAR19.28YFζ, CAR19.28AFAAζ) did not completely abolish the association of LCK to CAR19.28ζ (FIG. 2C). Similarly, basal CAR-CD3ζ phosphorylation was only modestly reduced and the cytokine production of CAR19.28ζ-T cells remained unaffected (FIG. 2C). Since no significant differences were observed between CD28 mutants and CAR19.28ζ in both phosphorylation of the CAR-CD3ζ and cytokine production, one representative mutant was chosen to monitor CD69 expression after anti-CAR19 activation. There were no significant differences on CD69 levels between CAR19.28ζ and CAR19.28AAAζ mutation either upon CAR or TCR crosslinking. Furthermore, in CAR molecules pulled down from CAR.19.BBζ-T cells the presence of LCK was observed even if the human 4-1BB endodomain does not contain any known LCK binding motifs. These observations suggest that LCK is recruited to the CAR synapse by co-receptors rather than by the CAR-associated CD28 moiety. By co-immunoprecipitation-mass spectrometry (Co-IP-MS), unique CD8α peptides were detected spanning regions absent in the CAR-CD8α stalk in CARs pulled down from both CAR19.28ζ-T and CAR.19.BBζ-T cells (Table 2). Furthermore, overexpression of a CD8α mutant that cannot bind to LCK (CKCP mutated to SKSP; CD8α-SKS) greatly reduced the basal CAR-CD3ζ phosphorylation in $CD4^+$ T cells expressing the CAR19.28ζ, while $CD4^+$ T cells co-expressing CAR.19.BK and the wild type CD8α (CD8α-wt) showed increased basal CAR-CD3ζ phosphorylation (FIG. 2D; top panel). We did not find any peptide of the CD4 co-receptor were found in the CAR29.28ζ pull-down product in Co-IP-MS even if $CD4^+$ T cells were still present at day 10-14 of culture. However, overexpression of the wild-type CD4 in both $CD4^+$ and $CD8^+$ CAR19.-BBζ-T cells increased the basal phosphorylation of CAR-CD3ζ (FIG. 2D; bottom panel). As observed for TCR signaling, these data support the conclusion that LCK recruited to the CAR synapse by either CD8 or CD4 co-receptors plays a major role in triggering the basal CAR-CD3ζ phosphorylation.

Figure 2E:
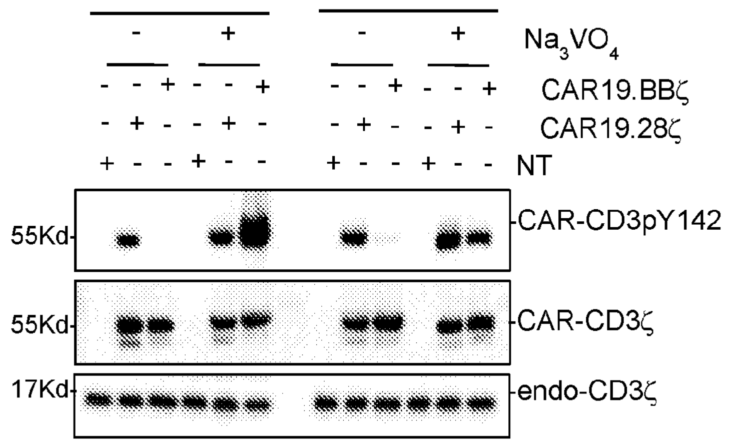
Figure 12:
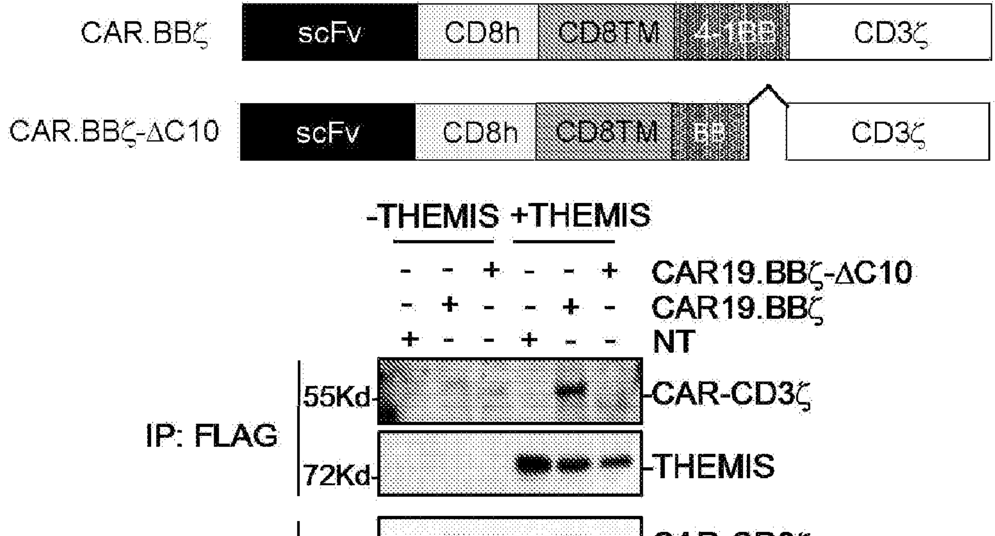
FIG. 12 shows that a c-terminal deletion of 4-1BB abolishes its interaction with THEMIS. Deletion construct is annotated as CAR.BBζ-ΔC10, versus complete construct as CAR.BBζ. NT stands for non-transduced.

THEMIS-SHP1 counteracts the effect of LCK in the CAR synapse of CAR-T cells encoding 4-1BB. Although co-receptors bring LCK into the CAR19.BBζ synapse (FIG. 2D, and Table 2), very low basal phosphorylation of the CAR-CD3ζ was observed, suggesting that 4-1BB may recruit phosphatases to the CAR synapse that counter the LCK-mediated phosphorylation. Indeed, the tyrosine phosphatase inhibitor $Na_3$ $VO_4$ promoted antigen-independent phosphorylation of CAR-CD3ζ in CAR19.BBζ-T cells (FIG. 2E). Accordingly, Co-IP-MS demonstrated that THEMIS is more abundantly associated with CAR19.BBζ than CAR19.28ζ (Table 2). While THEMIS does not have direct phosphatase activity, it binds to the phosphatase SHP1, and then the THEMIS/SHP1 complex is recruited by LAT to the TCR synapse to regulate T cell activation. THEMIS pull-down in T cells and Jurkat cells co-expressing THEMIS and CARs confirmed a stronger interaction between THEMIS and CAR19.BBζ than THEMIS and CAR19.28ζ. Knock-down of THEMIS or SHP1 in CAR19.BBζ-T cells using siRNAs increased their CAR-CD3ζ basal phosphorylation (FIG. 2F), indicating that the THEMIS-SHP1 complex negatively regulates CAR-CD3ζ phosphorylation of CAR19.BBζ. To map the domain of 4-1BB interacting with THEMIS, 4-1BB mutants were generated and it was observed that the COOH-terminal deletion of 10 amino acids abolishes 4-1BB interaction with THEMIS (FIG. 12), leading to increased CAR-CD3ζ phosphorylation (FIG. 2G), $Ca^{2+}$ influx (FIG. 13), CD69 expression and IFNγ release (FIG. 14) by the activated CAR19.BBζ-T cells. These data support the conclusion that the THEMIS-SHP1 complex selectively attenuates CAR-CD3ζ phosphorylation in CAR-T cells expressing 4-1BB.

Figure 3:
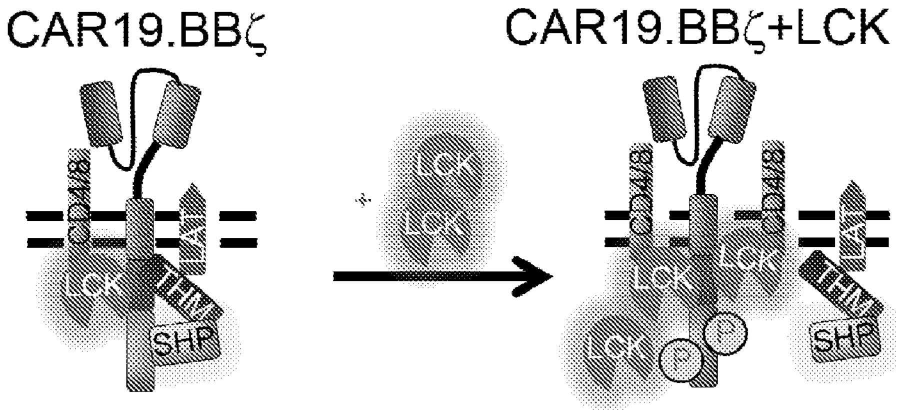
FIG. 3 shows a schema illustrating LCK engineering to counter the phosphatase activity of the THEMIS/SHP1 complex in CAR19.BBζ-T cells.
Figure 4:
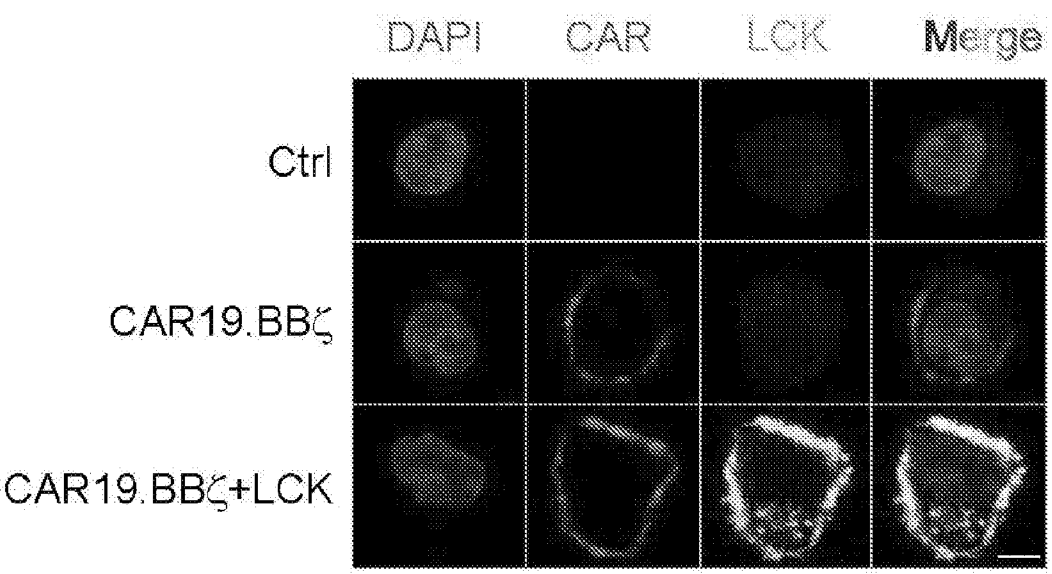
FIG. 4 shows confocal microscopy showing the LCK accumulation in the membrane in CAR19.BBζ-T cells co-transduced with the FLAG-tagged LCK. Scale bar represents 5 μm. The experiment was replicated in 3 donors.
Figure 5:
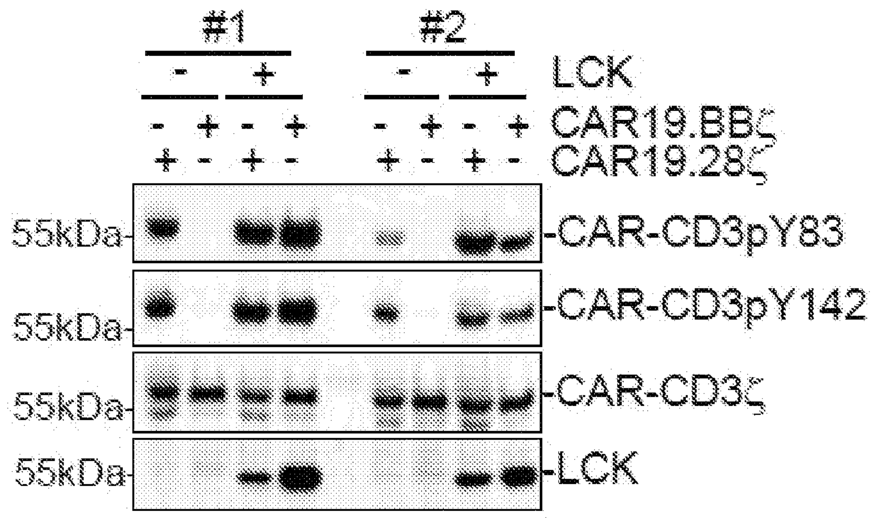
FIG. 5 shows phosphorylation of the CAR-CD3ζ Y83 and Y142 in CAR19.28ζ-T and CAR19.BBζ-T cells expressing the FLAG-tagged LCK (n=3).
Figure 6:
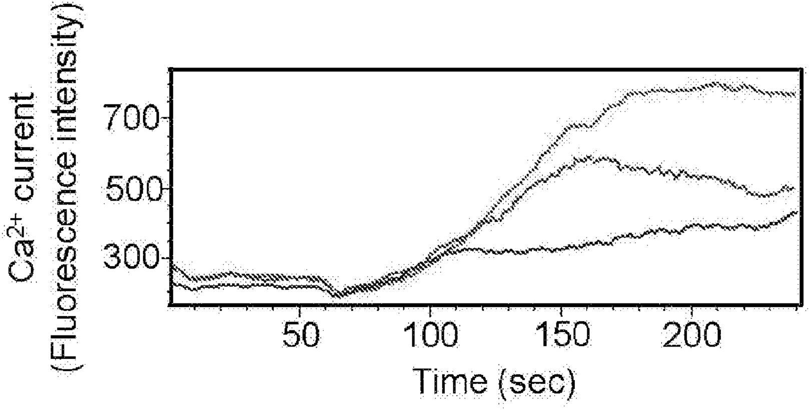
FIG. 6 shows representative and quantification of $Ca^{2+}$ influx in CAR19.28ζ-T cells, CAR19.BBζ-T cells with or without co-expression of FLAG-tagged LCK. Two-tailed unpaired t-test; (n=3).
Figure 6:
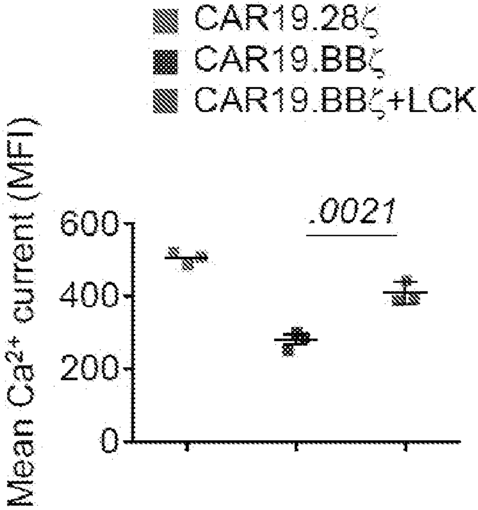
Figure 7:
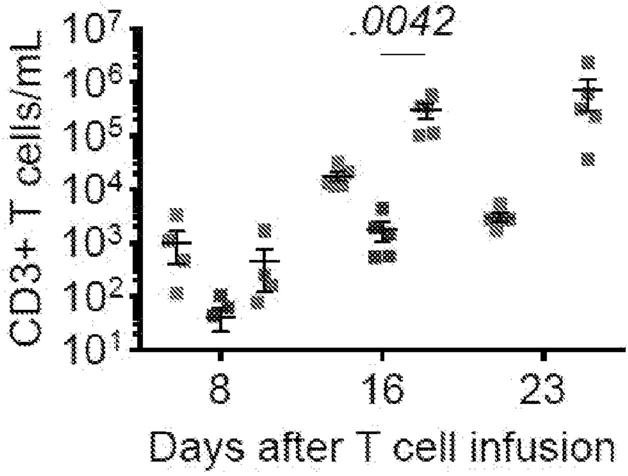
FIG. 7 shows quantification of T cells in the peripheral blood in NSG mice engrafted with the $CD19^+$ Daudi cells and infused with CAR19.28ζ-T cells, CAR19.BBζ-T cells with or without FLAG-tagged LCK. Re-challenging with Daudi cells were performed at day 32 and 47 after initial tumor infusion (indicated by arrows). Two-tailed unpaired t-test; (n=5 mice per group).
Figure 8A:
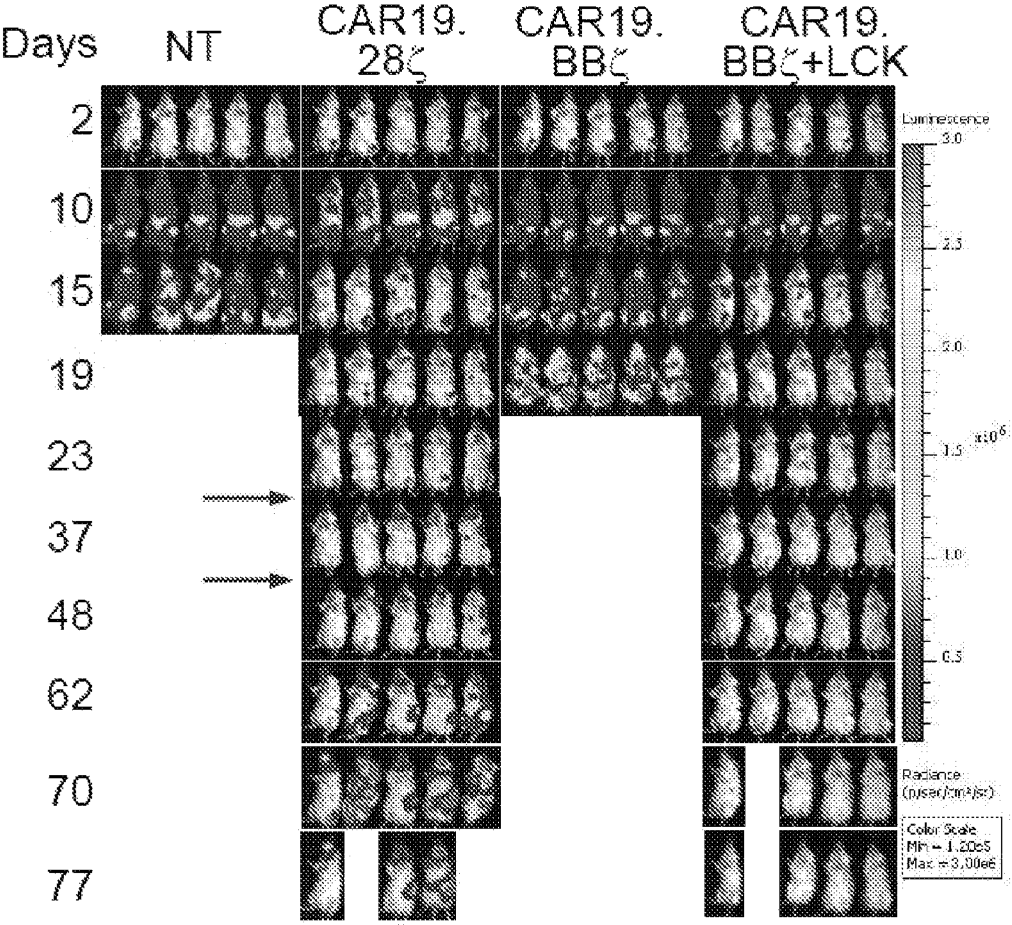
FIG. 8A shows tumor growth monitored by bioluminescence imaging (BLI) in the mice of FIG. 7.
Figure 8B:
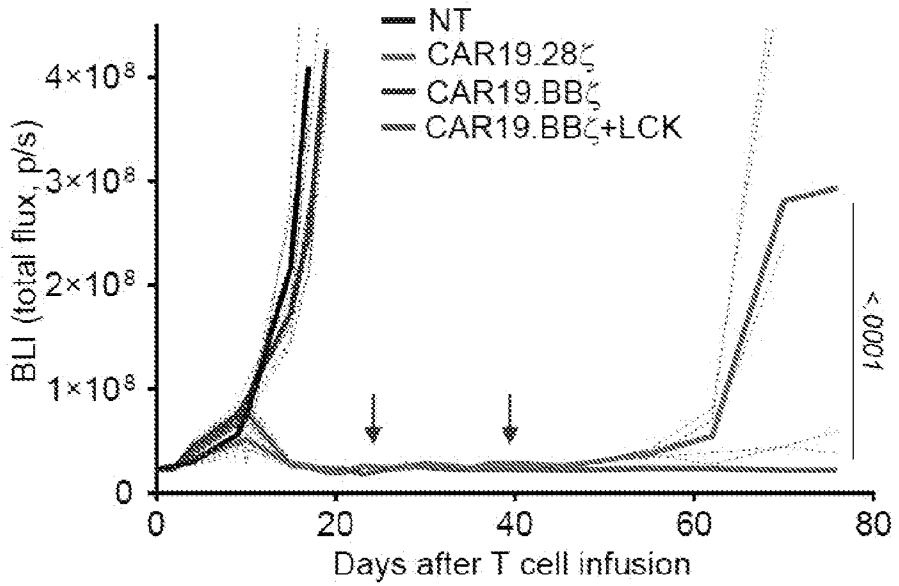
FIG. 8B shows tumor growth monitored by BLI in NSG mice engrafted with the $CD19^+$ Daudi cells and infused with suboptimal dose of CAR19.28ζ-T or CAR19.BBζ-T cells with or without LCK (n=5, two-way ANOVA).
Figure 8C:
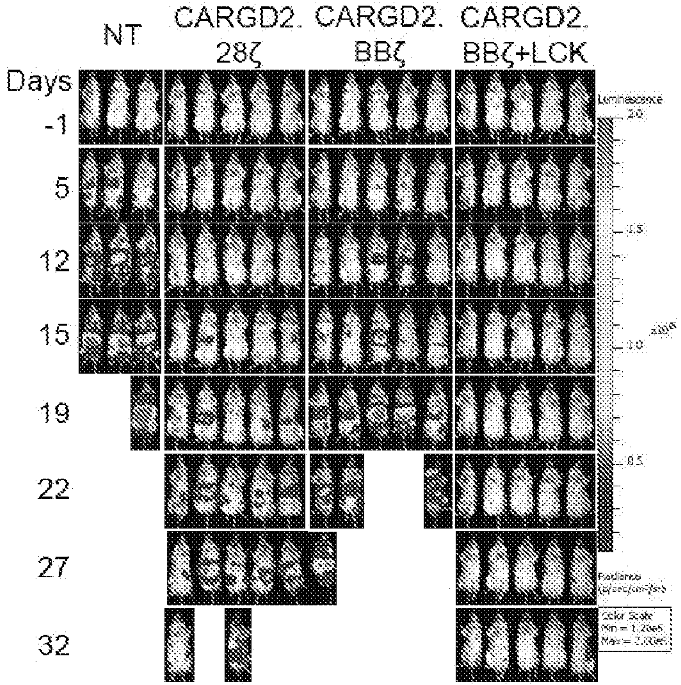
FIG. 8C shows tumor growth monitored by BLI in NSG mice engrafted with the neuroblastoma tumor cell line CHLA-255 and infused with either CARGD2.28ζ-T or CARGD2.BBζ-T cells with or without LCK.
Figure 8D:
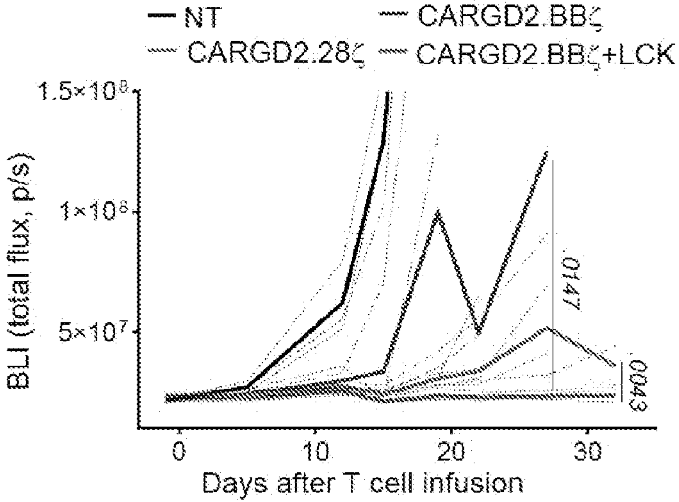
FIG. 8D shows tumor growth monitored by BLI in NSG mice engrafted with the neuroblastoma tumor cell line CHLA-255 and infused with suboptimal dose of either CARGD2.28ζ-T or CARGD2.BBζ-T cells with or without LCK (n=3 in NT (non-transduced) group, n=5 in other groups, two-way ANOVA).
Figures 8E, 8F:
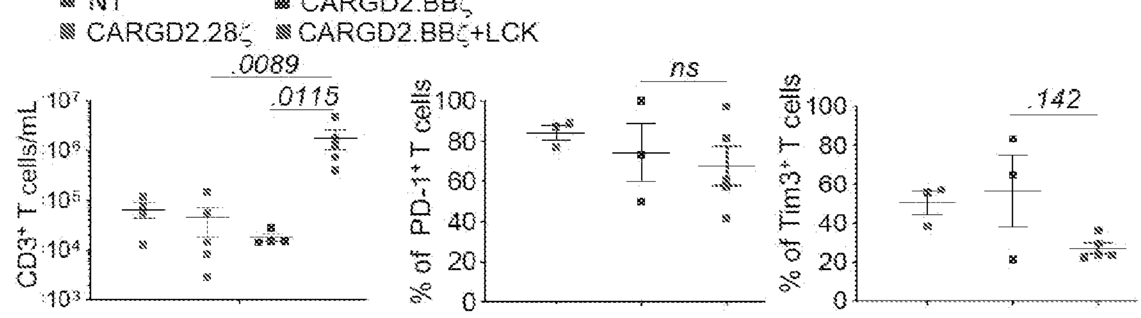
FIG. 8E shows T cell number at day 18 in circulating CAR-T cells in mice engrafted with the neuroblastoma tumor cells and treated as described in FIG. 8C (n=3 in NT group, n=5 in other groups, one-way ANOVA).
FIG. 8F shows expression of PD-1 and TIM3 at day 22 in circulating CAR-T cells in mice engrafted with the neuroblastoma tumor cells and treated as described in FIG. 8C (n=3 in NT group, n=5 in other groups, one-way ANOVA).

Engineering LCK kinas fine-tunes the antitumor activity of CAR-T cells encoding 4-1BB. LCK has access to the CAR19.BBζ synapse, but its kinase activity is limited by the presence of the THEMIS-SHP1 complex. While the COOH-terminal deletion of 10 amino acids abolishing the 4-1BB interaction with THEMIS promotes the rapid activation of CAR19.BBζ-T cells, this deletion also abrogates the binding to TRAF2, which would compromise 4-1BB signaling. In contrast, LCK overexpression in CAR19.BBζ-T cells may break the balance of kinases and phosphatases within the CAR synapse and promote basal CAR-CD3ζ phosphorylation (FIG. 3). Overexpressed LCK was found to retain its native N-terminal myristoylation and palmitoylation, and thus accumulate in the cell membrane of CAR19.BBζ-T cells (FIG. 4), increasing the basal phosphorylation of CAR-CD3ζ (FIG. 5) and $Ca^{2+}$ influx upon antigen stimulation (FIG. 4 and FIG. 6). CAR19.BBζ-T cells co-expressing LCK expanded numerically in vivo in a lymphoma tumor mouse model and showed better control of tumor growth at a suboptimal cell dose as compared to CAR19.BBζ-T cells (FIGS. 7, 8A, and 8B). Moreover, CAR19.BBζ-T cells co-expressing LCK better controlled tumor growth after tumor re-challenge as compared to CAR19.28ζ-T cells (FIGS. 8A and 8B). The beneficial effect of LCK overexpression in CAR-T cells encoding 4-1BB was also observed in a neuroblastoma model targeting the GD2 antigen (FIGS. 8C, 8D, and 8E) without causing any increase in the expression of PD-1 and TIM3 in CAR-T cells (FIG. 8F). These data support the conclusion that LCK overexpression in CAR-T cells expressing 4-1BB promotes faster antitumor activity without compromising their intrinsic enhanced persistence.

Figure 15:
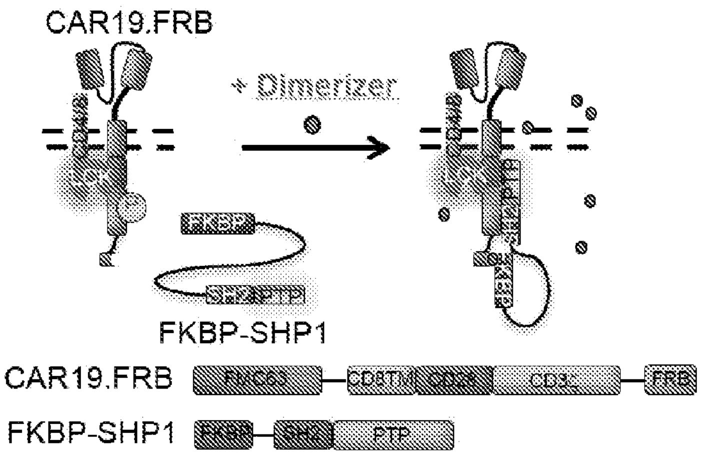
FIG. 15 shows a schema of the FRB and FKBP domain engineering of SHP1 and CARs to pharmacologically control SHP1 recruitment to the CAR19.28ζ synapse.
Figure 16:
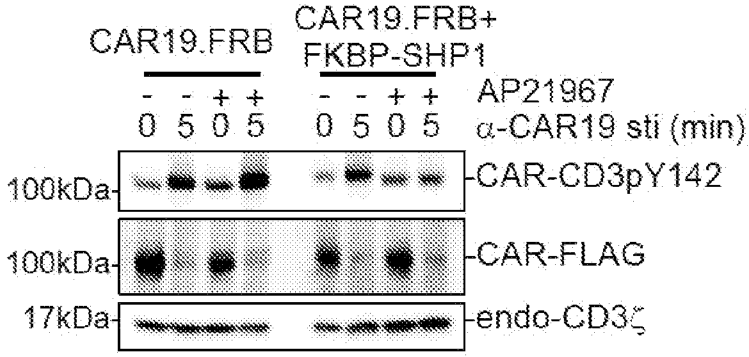
FIG. 16 shows phosphorylation of CAR-CD3ζpY142 in CAR19.28ζ.FRB-T cells alone or co-transduced with FKBP-SHP1 after the stimulation with anti-CAR19 antibody in the presence of vehicle (ethanol) or 1 μM AP21967. The experiment was replicated in 3 donors.
Figure 17:
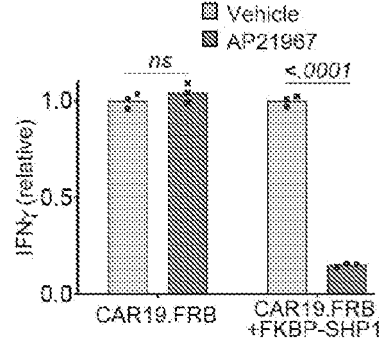
FIG. 17 shows IFNγ released in the supernatant by CAR19.28ζ.FRB-T cells alone or co-transduced with FKBP-SHP1 and incubated with the CD19$^+$ BV173 tumor cell line at a 1:5 ratio in the presence of vehicle or AP21967. n=3, values were normalized to average values in vehicle groups, two-way ANOVA; representative of 3 donors.
Figure 18:
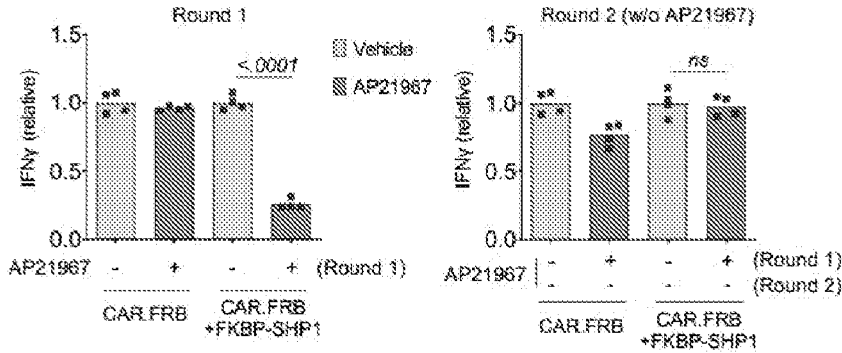
FIG. 18 IFNγ release in the supernatant by CAR19.28ζ.FRB-T cells alone or co-expressing FKBP-SHP1 and incubated with the CD19$^+$ BV173 tumor cell line at a 1:5 ratio. CAR-T cells were co-cultured in the presence of vehicle or AP21967 during round #1. Vehicle or AP21967 were added to the co-cultures every day. At day 3, cells were washed and transferred into a new well with BV173 cells without AP21967 during round #2 (n=4, values were normalized to average values in vehicle group, two-way ANOVA; representative of 2 donors).
Figure 19A:
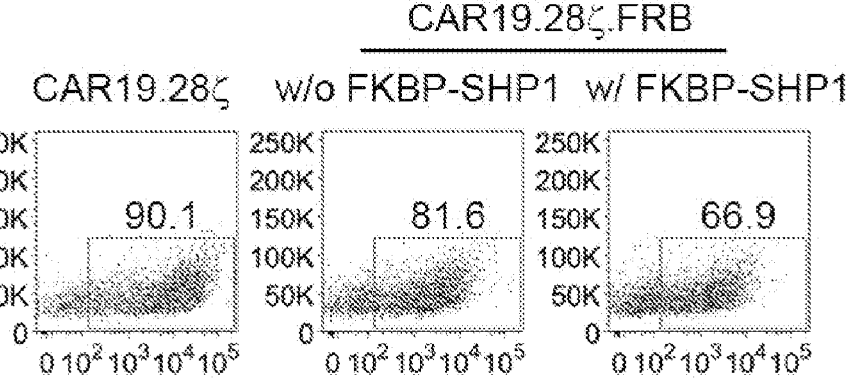
FIG. 19A shows representative flow plots of the expression of CAR in CAR19.28ζ-T or CAR19.28ζ.FRB.FLAG-T cells without or with co-transduction of FKBP-SHP1.
Figure 19B:
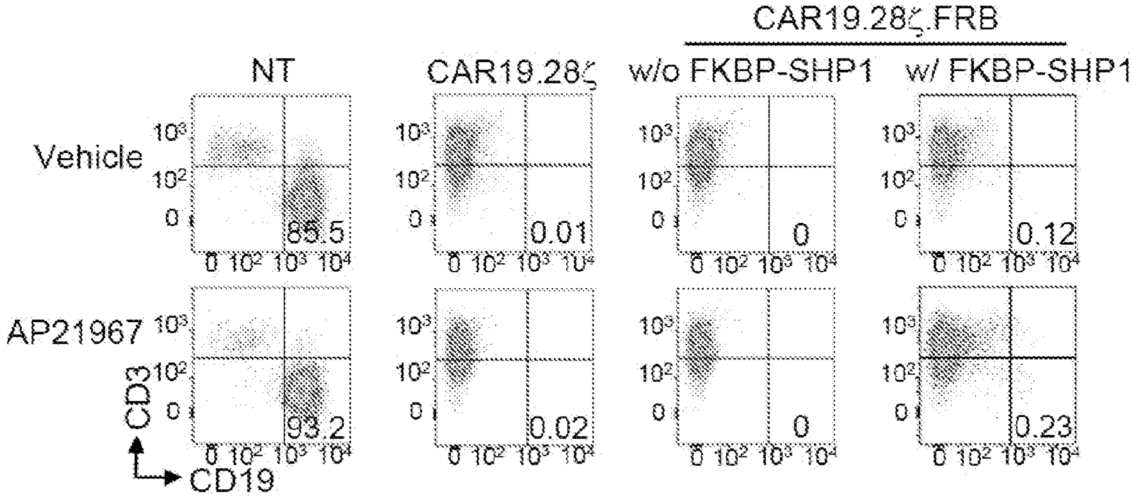
FIG. 19B shows CD19$^+$ BV173 tumor cells that were co-cultured with NT, CAR19.28ζ-T and CAR19.28ζ.FRB.FLAG-T cells co-transduced without or with FKBP-SHP1 for 3 days. Vehicle (ethanol) or AP21967 (1 μM) was added to the co-cultures every day. At day 3, cells were collected to evaluate the presence of T cells and tumor cells by flow cytometry. The experiment was replicated in 3 donors.
Figure 20A:
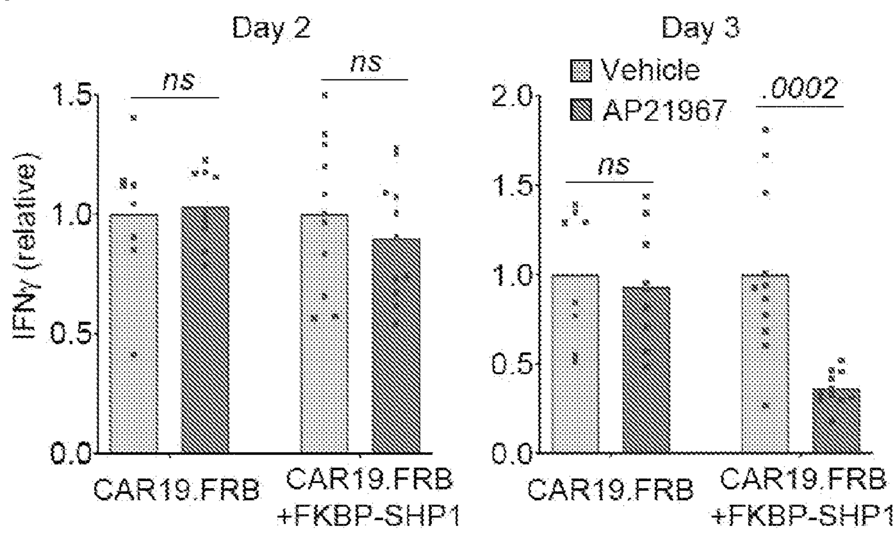
FIG. 20A shows IFNγ level in the plasma of mice before (Day 2) and after (Day 3) the administration of vehicle or AP21967 (n=9-11, values were normalized to average values in vehicle groups, two-way ANOVA; pooled data from 2 independent experiments).
Figure 20B:
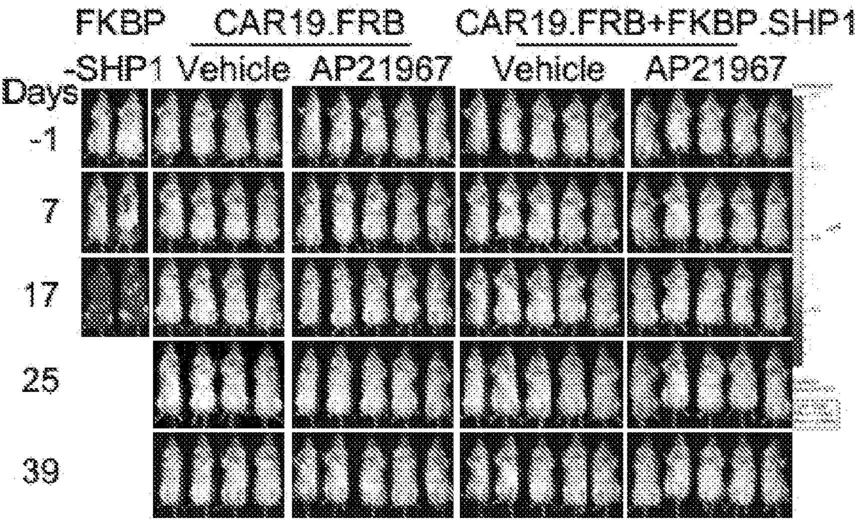
FIG. 20B shows representative tumor growth monitored by BLI in NSG mice (n=4-5, representative of 2 independent experiments).

Engineering SHP1 phosphatase fine-tunes the effector function of CAR-T cells encoding CD28. CAR-T cells infused in patients with significant leukemia or lymphoma tumor burden cause cytokine release syndrome (CRS). While the administration of a monoclonal antibody blocking the IL-6 receptor has been demonstrated effective in attenuating CRS, the implementation of a precise pharmacologic control of CAR-T cells remains highly appealing. In this study, SHP1 was modified allowing it to be pharmacologically recruited to the CAR synapse via the FKBP-FRB heterodimerization process (FIGS. 15 and 19A). In response to the heterodimerization small molecule AP21967, FKBP-SHP1 forms heterodimers with CAR19.28ζ tunes down CAR-CD3ζ phosphorylation upon antigen binding (FIG. 16), and reduces IFNγ release by CAR19.28ζ-T cells in a reversible manner without compromising their antitumor activity in vitro (FIGS. 17 and 18). Similarly, in a xenograft lymphoma model wherein tumor cells were inoculated at day −7, T cells were infused at day 0, AP21967 was administered twice on day 2, blood was sampled on days 2 and 3, and tumor growth was measured on days 7-39, the administration of the AP21967 in vivo reduced IFNγ release by CAR19.28ζ-T cells co-expressing SHP1, without impairing their antitumor effects (FIGS. 20A-20B).

Figure 2F:
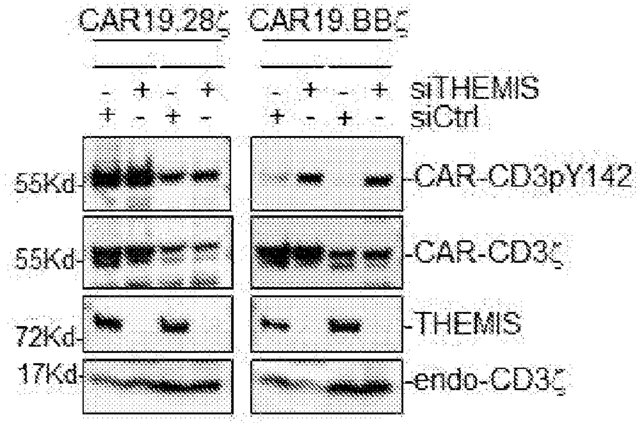
Figure 2G:
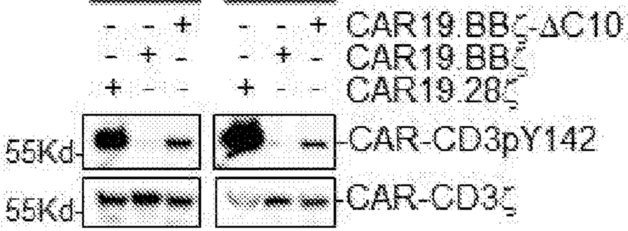
Figure 21A:
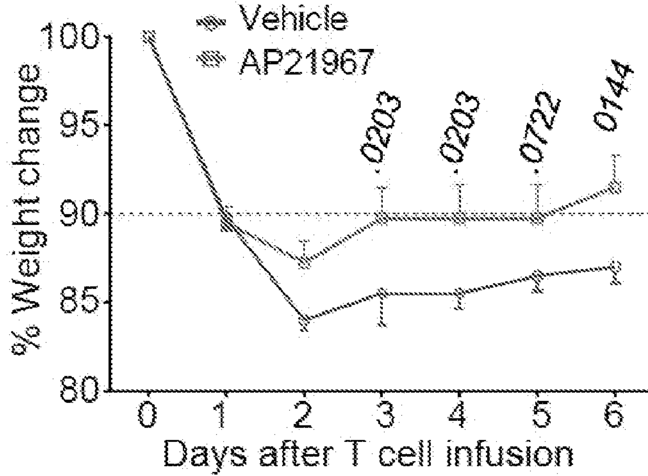
FIG. 21A shows weight change in humanized NSG mice after CAR-T cell infusion. Weight was normalized to the starting weight before CAR-T cell infusion. Human IFN□ and IL-6 were detected before (D1) and after (D2) the administration of vehicle or AP21967 (n=4, two-way ANOVA).
Figure 21B:
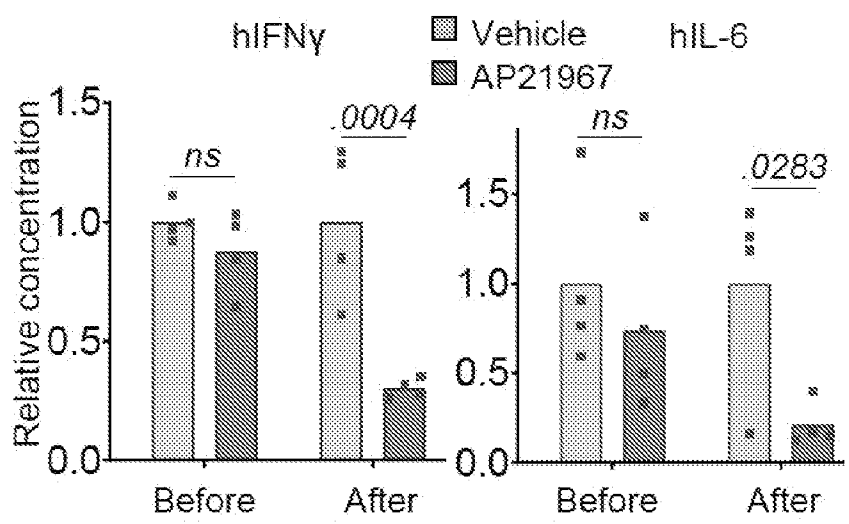
FIG. 21B shows cytokine detection under the same conditions as described for FIG. 21A.
Figure 21C:
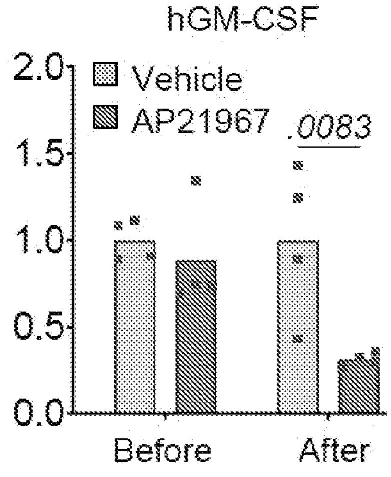
FIG. 21C shows cytokine production and FIG. 21D shows cell counts in humanized mice infused with CAR-T cells. Human GM-CSF and TNFα were detected before (Day 1) and after (Day 2) the administration of vehicle or AP21967. Human B and T cells in the peripheral blood were counted by flow cytometry before and 3 weeks after CAR-T cell infusion (n=4, values were normalized to average values in vehicle groups in d, two-way ANOVA).
Figure 21C:
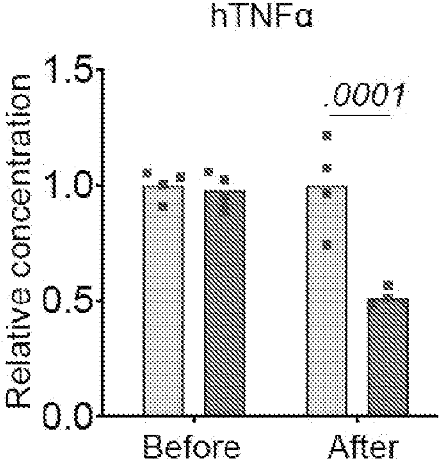
Figure 21D:
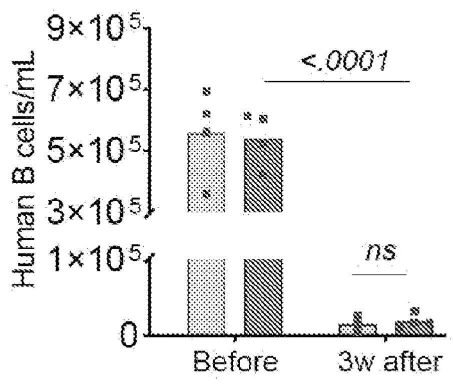
Figure 21D:
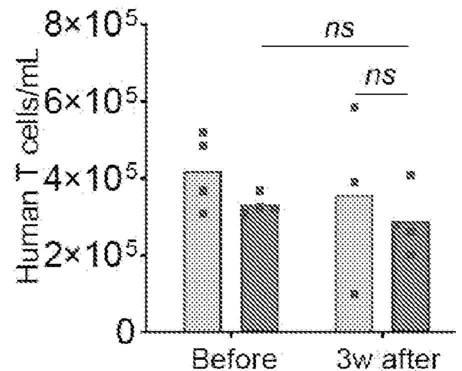
Figure 21E:
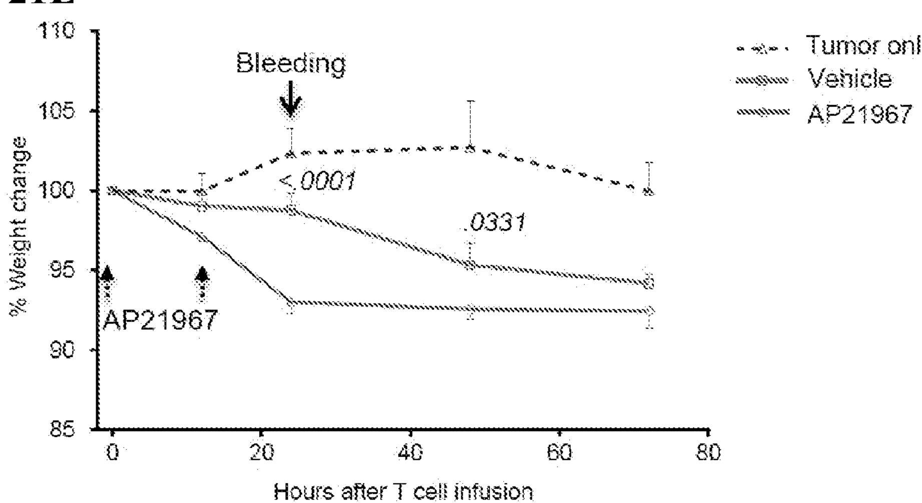
FIG. 21E shows weight change and FIG. 21F shows cytokine detection in tumor bearing SCID-beige mice infused with CAR-T cells. Raji-FFluc tumor cells were injected intraperitoneally at day −21. Vehicle or AP21967 was injected i.p. 1 hour before and 12 hours after CAR19.FRB+FKBP-SHP1-T cell infusion. Human IFNγ, GM-CSF, TNFα, and murine IL-6 were detected in the plasma at 24 hour (n=5-7 in FIG. 21E, mouse weight was normalized to starting weight before CAR-T cell infusion, two-way ANOVA, p value between vehicle and AP21967 groups; n=10-12 in FIG. 21F, values were normalized to average values in vehicle group, one-way ANOVA).
Figure 21F:
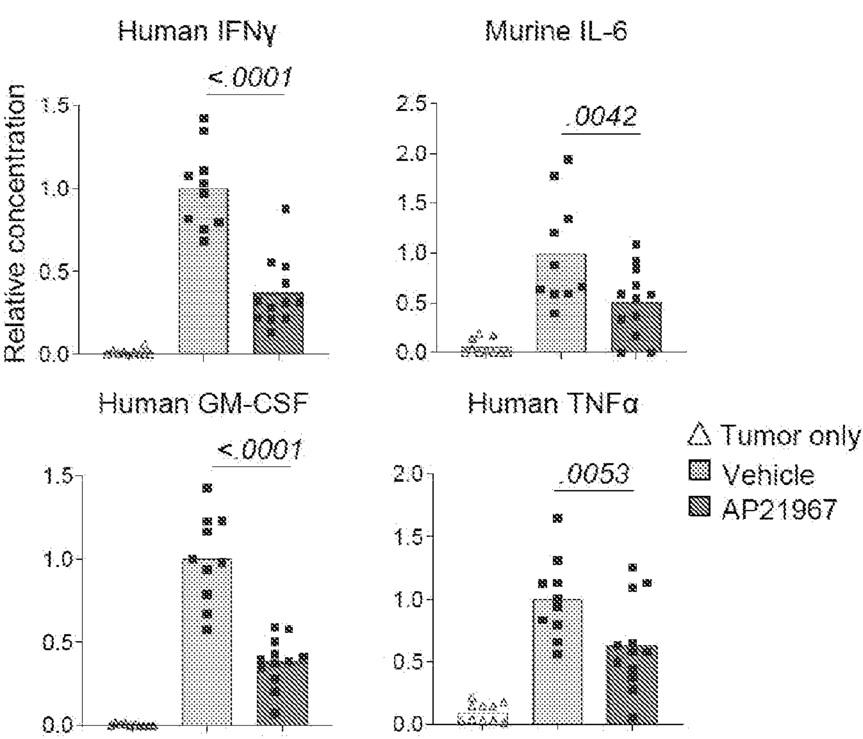

Since NSG immunodeficient mice are not appropriate models for CRS, a humanized mouse model in which CAR-T cell inoculation causes the release of human IL-6 in the plasma of treated mice was used instead. In these humanized mice, CAR-T cells were infused on day 0, AP21967 was administered twice on day 1, blood was sampled on days 1 and 2, and cell counts were measured on day 21. SHP1 recruitment induced by the transient administration of AP21967 alleviated their weight loss (FIG. 21A) and significantly reduced the release in the plasma of human IFNγ, IL-6, GM-CSF, and TNFα (FIGS. 21B-21C). Importantly, the transient use of AP21967 did not impair the therapeutic effect of CAR19.28ζ-T cells in vivo (FIG. 21D). The effect of SHP1 heterodimerization in vivo on cytokine release was further validated in another CRS model, using SCID-beige mice (FIGS. 21E-2F). Taken together, these data demonstrate that the transient recruitment of SHP1 within the CAR19.28ζ synapse by the heterodimerization small molecule AP21967 can tune down the severity of CRS without impairing the antitumor effects of CAR-T cells.

Costimulation plays a fundamental role in promoting the antitumor effects and persistence of CAR-redirected T cells. This study demonstrates that CD28 and 4-1BB endodomains incorporated into CAR molecules differentially regulate the equilibrium of phosphorylation and dephosphorylation of the CAR-CD3ζ endodomain and this in turn regulates the magnitude of CAR-T cell activation. Furthermore, this study provides data supporting the notion that the equilibrium of LCK/THEMIS-SHP1 can be genetically manipulated to modulate efficacy and safety of CAR-T cells.

It has been recognized in clinical trials that CD19-specific CAR-T cells encoding either CD28 or 4-1BB costimulatory endodomains promote equal antitumor activity in patients with B cell malignancies. However, preclinical models showed that CD28 and 4-1BB have fundamental biological differences that may be critical in inducing antitumor effects and in promoting persistence of CAR-T cells. CD28 costimulation is generally associated with a very rapid tumor clearance as compared to 4-1BB, but also more pronounced propensity to exhaustion (Zhao et al. 2015 *Cancer Cell*

28:415-428; Long et al. 2015 *Nat. Med.* 21:581-591). Here the rapid kinetics of CD28 expressing CAR-T cells are mechanistically linked with the basal phosphorylation of the CAR-CD3ζ endodomain. The basal phosphorylation is caused by LCK recruited within the CAR synapse, which is largely mediated by co-receptors rather than the CD28 incorporated within the CAR, and imprints CAR-T cells to higher magnitude of response immediately upon encountering the antigen. In sharp contrast, the synapse formed by CAR molecules containing the 4-1BB endodomain selectively recruits the THEMIS-SHP1 complex that dephosphorylates the CAR-CD3ζ endodomain and attenuates T cell activation. This study demonstrated a direct interaction between THEMIS and 4-1BB encoded within the CAR by overexpressing a tagged THEMIS, though it was not possible to show the direct interaction with the endogenous TEHMIS. This may be attributable to a lack of appropriate reagents to immune precipitate to endogenous THEMIS. However, all performed experiments highlight the biological relevance of the discovered interaction between THEMIS and 4-1BB in CAR molecules.

These mechanistic discoveries have immediate translational implications because kinases and phosphatases can be engineered in CAR-T cells to either enhance or tune down their activation. It is demonstrated herein that LCK when overexpressed in CAR19.BBζ-T cells breaks the balance of kinases and phosphatases within the CAR synapse increasing the basal phosphorylation of CAR-CD3ζ and the speed of their antitumor effects. However, while CD28 costimulation prone CAR-T cells to exhaustion, LCK overexpression in 4-1BB costimulated CAR-T cells does not affect the intrinsic property of 4-1BB signaling to protect T cells from exhaustion since the antitumor response is maintained after tumor re-challenge. Enhancing the kinetics of antitumor activity of 4-1BB, while preserving longevity, may be critical in controlling rapidly progressive solid tumors.

Toxicities associated with CAR-T cells such as CRS remain of great concern. Pharmacologic and remote control of CAR-T cells has been explored to modulate CAR-T cell expansion in vivo and mitigate side effects. While the remote control of T cell proliferation remains challenging in the clinical setting, the mechanistic observations of this study suggest that a temporary break of T cell activation can be achieved via phosphatase engineering. Phosphatases play a critical role in attenuating CAR signaling and herein is demonstrated that SHP1 can be pharmacologically recruited to the CAR synapse and temporarily attenuate T cell function without eliminating CAR-T cells.

In summary, CD28 and 4-1BB differentially regulate the equilibrium of phosphorylation and dephosphorylation of the CAR-CD3ζ, which in turn regulates the magnitude of CAR-T cell activation. Engineering kinases and phosphatases can be used to tune CAR-T cell function for adoptive immunotherapy.

Example 2: CAR and LCK Overexpression Construct

CAR-Ts with CD28 show faster kinetics of activity and lower activation threshold than CAR-Ts with 4-1BB, leading to in vivo control of tumor at lower dose. We have found that this phenomenon is due to the imbalance of kinase and phosphatase among CAR.28ζ and CAR.BBζ synapse, while more kinase activity in CAR.28ζ synapse resulting from LCK recruited by the co-receptors. Therefore, we modified CAR.BBζ-Ts with overexpression of LCK to achieve faster response and meanwhile maintain their advantage of better persistence. We anticipate this invention will further improve the clinical outcomes of different CAR-T therapies for corresponding cancers.

Overexpression of LCK can break the balance of kinase and phosphatase in CAR19.BBC synapse. Overexpress LCK kinase in CAR19.BBζ-Ts can potentially improve its antitumor activity. CAR19.28ζ-Ts shows faster response to tumor cells and better tumor control at lower doses comparing to CAR19.BBζ-T cells (v.d. Stegen et al. 2015 *Nat. Rev. Drug Discov.* 14(7):499-509; Zhao et al. 2015 *Cancer Cell* 28(4):415-428; Kawalekar et al. 2016 *Immunity* 44(3); 712). This phenomenon is due to the presence of antigen independent CAR-CD3ζ phosphorylation and lower activation threshold of CAR19.28ζ-T cells (Salter et al. 2018 *Sci. Signal.* 11:544). We have found that the imbalance of kinase and phosphatase in CAR synapse is the cause of this phenomenon. CAR19.28ζ has more kinase activity (LCK) while CAR19.BBζ recruits more phosphatase (THEMIS-SHP1) in the synapse. Therefore, overexpressing LCK in CAR19.BBζ-Ts will increase the kinase activity to counteract the effect of phosphatase. However, this modification will only affect the CD3ζ phosphorylation and early phase CAR-T activation without abolishing 4-1BB functions, thus CAR19.BBζ-Ts will still persist better over CAR19.28ζ-Ts (FIG. 3).

LCK overexpressed in CAR19.BBζ-Ts is accumulated in cell membrane. To overexpress LCK, two retroviruses (encoding CAR19.BBζ and LCK-FLAG, respectively) were used to co-transduce activated T cells. This allows the expression of both proteins at high level. To assess the expression level and the localization of these proteins, immunofluorescence was performed with confocal microscopy on control (Ctrl), CAR19.BBζ-only and CAR19.BBζ+LCK transduced T cells. LCK was found to be enriched in the regions of cell membrane (stained by CAR, FIG. 4), consistent with the reports that this is due to the N-terminal myristoylation and palmitoylation of LCK, allowing its binding to inner cell membrane. This result indicated that LCK overexpressed in CAR19.BBζ-Ts are co-localized with CAR19.BBζ and can potentially increase the antigen independent CAR-CD3ζ phosphorylation of CAR19.BBζ.

Overexpression of LCK in CAR19.BBζ-Ts increased antigen independent CAR-CD3ζ phosphorylation and $Ca^{2+}$ influx upon antibody stimulation. To confirm the direct effect of LCK overexpression in CAR19.BBζ-Ts, the CAR-CD3ζ phosphorylation of CAR19.BBζ was assessed in three different donors at day 10 of in vitro expansion by western blot. CAR19.BBζ shows very low antigen independent CAR-CD3ζ phosphorylation comparing to CAR19.28ζ while overexpressing LCK dramatically increased CAR-CD3ζ phosphorylation of CAR19.BBζ to a comparable level as CAR19.28ζ (FIG. 5). LCK also enhanced CAR-CD3ζ phosphorylation in CAR19.28ζ-Ts, implicating that even CAR19.28ζ not reach its full potential under the resting status. The increase of antigen independent CAR-CD3ζ phosphorylation by LCK overexpression could also translate into functional readout, as the $Ca^{2+}$ influx of CAR-Ts stimulated with α-CAR19 antibody is correspondingly increased in those T cells with LCK overexpression (FIG. 6).

Co-expression of LCK in CAR19.BBζ-Ts increases circulating T cells in vivo and improves antitumor activity of CAR19.BBζ-Ts. To evaluate the functional benefits of LCK overexpression in CAR19.BBζ-Ts, their antitumor activity was tested in $CD19^+$ tumor engrafted NSG mice comparing to CAR19.28ζ-Ts and CAR19.BBζ-Ts. Because increased CAR-CD3 phosphorylation leads to faster activation and potentially better proliferation, we first accessed the number of circulating T cells in the peripheral blood of the mice at first three weeks after T cell infusion. Indeed, co-expressing LCK in CAR19.BBζ-Ts significantly increased circulating T cells in vivo (FIG. 7), which translated into more profound antitumor effect of CAR19.BBζ-Ts with LCK than the ones without and is comparable to that of CAR19.28ζ-Ts (FIG. 8A). Overall, these results indicated that overexpression of LCK can increase the activation magnitude of CAR19.BBζ-Ts while maintain the better persistence, leading to improved tumor control in vivo.

Example 3: CAR-FRB Construct

More kinase activity in CAR.28ζ synapse resulting from LCK recruited by the co-receptors, while recruitment of THEMIS/SHP1 phosphatase complex in CAR.BBζ synapse counteracts the effect of LCK. Therefore, we engineered SHP1 phosphatase as a representative regulator to allow its pharmacological recruitment into CAR synapse. This allows fine-tuning of the cytokine production and cytotoxicity of CAR-Ts, to avoid potential cytokine release syndrome during CAR-T therapy without ablating CAR-T cells.

Figure 9:
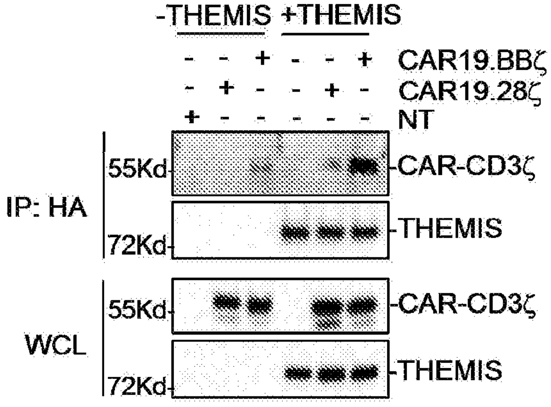
FIG. 9 shows results of a co-IP of THEMIS with CAR in CAR19.28ζ-T cells and CAR19.BBζ-T cells.

CAR.BBζ recruits THEMIS/SHP1 phosphatase complex into CAR synapse. We have found in our study that LCK kinase is recruited into CAR.28ζ synapse to induce basal CD3ζ phosphorylation of the CAR, leading to high magnitude of activation of CAR.28ζ-Ts. However, we did not observe the same effect in CAR.BBζ-Ts although LCK was also seen in the pull-down product of CAR.BBζ. We reasoned that there might be phosphatase(s) that counteract the effect of LCK in CAR.BBζ synapse. Indeed, by Co-IP coupled mass spectrometry, we identified that THEMIS is more enriched in CAR.BBζ synapse (Table 2). Co-IP results further confirmed the presence of THEMIS in CAR.BBζ complex but not in CAR.28ζ complex (FIG. 9).

Figure 10:
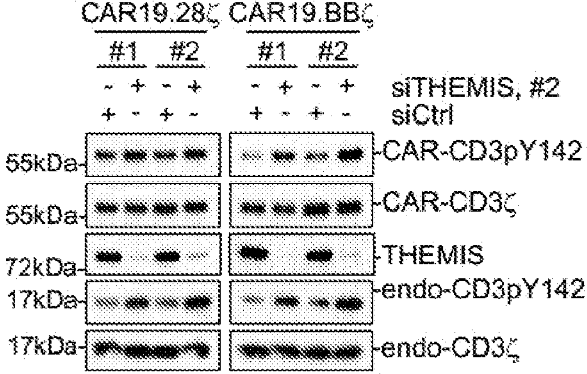
FIG. 10 shows siRNA knockdown of THEMIS increases CAR-CD3ζ phosphorylation in CAR19.BBζ-T cells but not in CAR19.28ζ-T cells.
Figure 11:
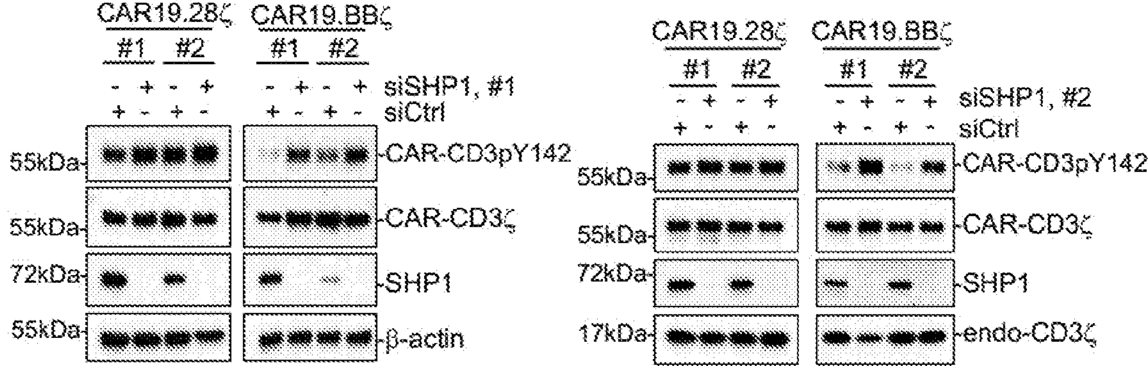
FIG. 11 shows siRNA knockdown of SHP1 increases CAR-CD3ζ phosphorylation in CAR19.BBζ-T cells but not in CAR19.28ζ-T cells.

THEMIS/SHP1 in CAR.BBζ synapse counteracts the effect of LCK to increase the magnitude of activation. While THEMIS does not have direct phosphatase activity, it binds to the phosphatase SHP1, and the complex THEMIS/SHP1 is recruited by LAT in the TCR synapse to regulate T cell activation. Knockdown of THEMIS or SHP1 in CAR.BBζ-Ts by siRNAs increased the basal CD3ζ phosphorylation of CAR, mimicking the effect of LCK in CAR.CD28ζ synapse (FIGS. 10 and 11).

Figure 13:
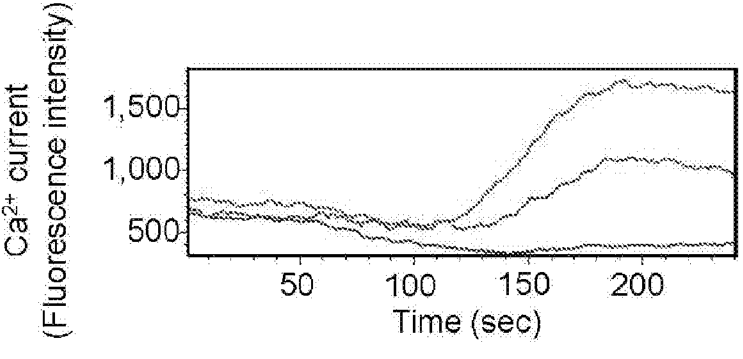
FIG. 13 shows Ca2+ influx in CAR19.28ζ-T cells, CAR19.BBζ-T cells and CAR19.BB-ΔC10-T cells following stimulation with the anti-CAR19 antibody.
Figure 13:
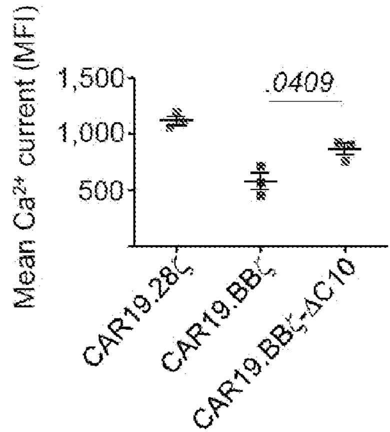
Figure 14:
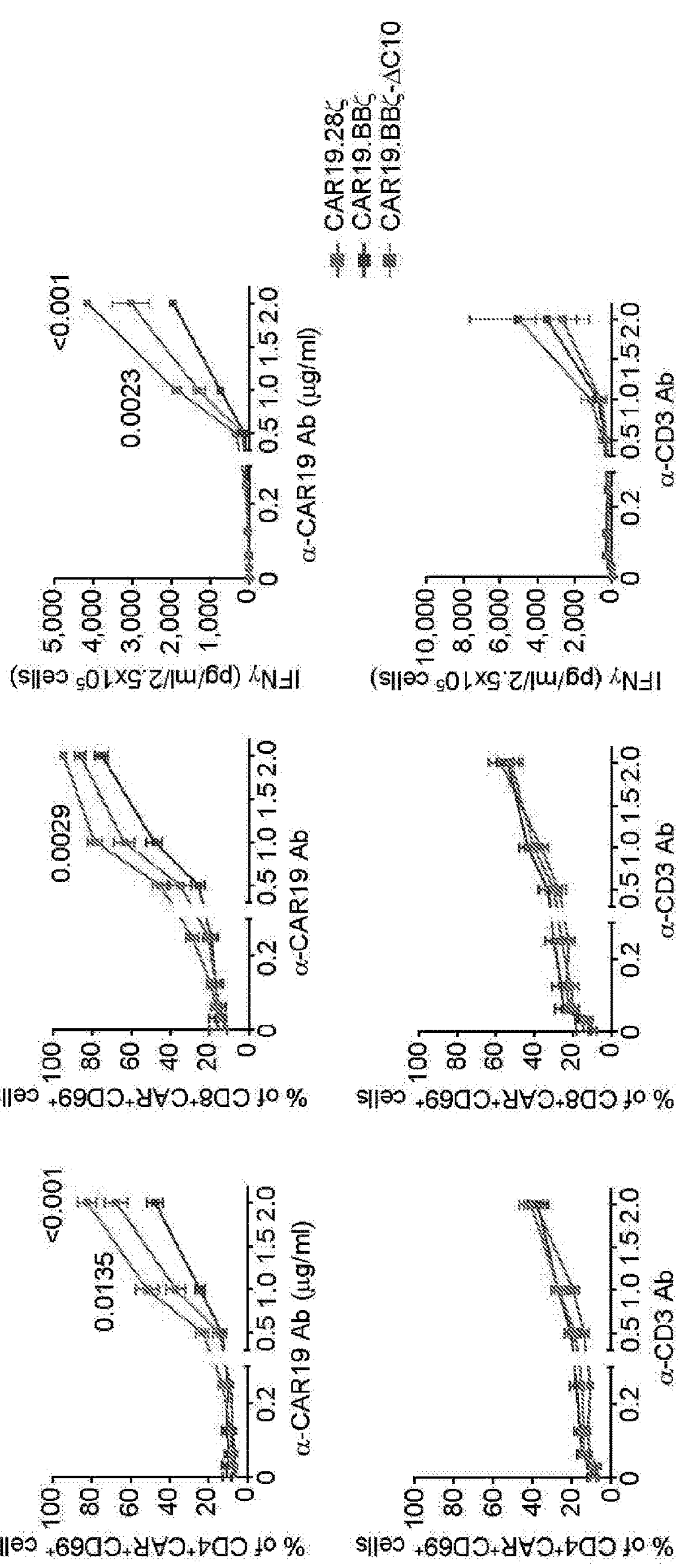
FIG. 14 shows CD69 expression and IFNγ release in CAR19.28ζ-T cells, CAR19.BBζ-T cells and CAR19.BBζ-ΔC10-T cells upon anti-CAR19 antibody stimulation. Two-way ANOVA; (n=5 for CD69 expression and n=3 for IFNγ release).

To map the domain of 4-1BB that mediates its interaction with THEMIS, several deletion mutants were created. A 10-amino acid deletion of the C terminus of 4-1BB abolished its interaction with THEMIS (FIG. 12), leading to increased $Ca^{2+}$ influx (FIG. 13) and magnitude of CAR-mediated activation (FIG. 14).

Pharmacological recruitment of FKBP-SHP1 can control the cytokine release and cytotoxicity of CAR-Ts. Pharmacologic and remote control of CAR-Ts has been explored to control CAR-T expansion in vivo and its related side effects. Regulated phosphatase activity in CAR-Ts can be used as an adjustable switch to fine-tune the activation and cytotoxicity of CAR-Ts without ablating these cells. For this purpose, we modified SHP1 allowing it to be pharmacologically recruited via FKBP/FRB heterodimerization in the CAR synapse (FIG. 13). In response to AP21967, FKBP-SHP1 forms heterodimers with CAR19.28ζ and can reduce antigen-independent CAR-CD3ζ phosphorylation of CAR19.28ζ-Ts (FIG. 16), leading to reversible regulation of IFNγ production and controlled cytotoxicity (FIG. 17).

Example 4: Methods Using Examples 1-3

293T cells were cultured in IMDM (Gibco, Invitrogen) supplemented with 10% fetal bovine serum (FBS, HyClone, Thermo Scientific), 2 mM GlutaMax, 100 I.U./mL penicillin and 10011 g/mL streptomycin (Invitrogen). BV173, Jurkat and Daudi-FFLuc cell lines were cultured in RPMI-1640 (Gibco, Invitrogen) supplemented with 10% FBS (HyClone), 2 mM GlutaMax, 100 I.U./mL Penicillin and 10011 g/mL Streptomycin (Invitrogen). All cell lines were routinely tested for mycoplasma.

CD19-specific CARs were constructed using the scFv from the FMC63 monoclonal antibody (Ab), the CD8α stalk including hinge and transmembrane domain, and CD3ζ chain intracytoplasmic domain (Diaconu et al. 2017 Mol. Ther. 25:580-592). CAR19.28ζ and CAR19.BBζ contained CD28 and 4-1BB endoplasmic domains, respectively. CAR19.28AAAζ mutation of PYAPP to AYAAA), CAR19.28YFζ (mutation of PYAPP to PFAPP), CAR19.28AFAAζ (mutation of PYAPP to AFAAA) and CAR19.BBζ-ΔC10 were generated by overlapping PCR. CARGD2 (targeting the GD2 antigen) and CAR138 (targeting the CD138 antigen) were generated by replacing the scFv of CAR19. CARs with the IgG1 hinge or the CD28 transmembrane domain were cloned by overlapping PCR to replace CD8α hinge or transmembrane domain. CAR19.28.CD3Y6Ft and CAR19.BB.CD3Y6Fζ were generated by gene synthesis (GeneArt, Thermo Scientific) and cloned into the original CAR19.28ζ construct. The full-length human THEMIS (accession_NM_001164685.1) and LCK (accession_NM_001042771.2) were PCR amplified from a cDNA library of activated T cells, and cloned into the SFG retroviral vector after the addition of the HA or FLAG tags. Gene expression was verified in both 293T and T cells by western blot. FRB and FKBP domains were cloned by PCR from plasmid PM-FRB-mRFP-T2A-FKBP-5-ptase (Addgene #40896). SHP1 full length (accession_NM_002831.5) was PCR amplified from a T cell cDNA library, and cloned into the SFG vector with FKBP. CAR19.28ζ.FRB.FLAG was generated by overlapping PCR. Lentiviral constructs encoding siRNAs were obtained from UNC shRNA Core Lab and tested for knockdown efficiency in primary T cells. Two functional shRNAs were selected for functional assays.

To prepare retroviral supernatants, 293T cells were transfected with 3 plasmids (retroviral transfer vector, Peg-Pam-e encoding gag-pol, and RDF encoding the RD114 envelope), using GeneJuice transfection reagent (Novagen). Supernatants were collected at 48 and 72 hours. Lentiviral supernatants were produced in 293T cells with 3 different plasmids (lentiviral transfer vector, ps.pAX2 for lentiviral gag-pol and pMD.2G for VSV-G envelope). Supernatant was collected at 48 hours for transduction of T cells.

For the transduction and expansion of human T cells, Buffy coats from healthy donors were obtained through the Gulf Coast Regional Blood Center, Houston, TX. Peripheral blood mononuclear cells (PBMCs) were isolated with Lymphoprep density separation (Fresenius Kabi Norge) and activated using 1 μg/mL anti-CD3 (Miltenyi Biotec) and 1 μg/mL anti-CD28 (BD Biosciences) mAb coated plates. Forty eight hours later, T lymphocytes were transduced with retroviral or lentiviral supernatants using retronectin-coated plates (Takara Bio), and expanded in complete medium (45% RPMI-1640 and 45% Click's medium (Irvine Scientific), 10% FBS (Hyclone), 2 mM GlutaMAX, 100 I.U./mL of Penicillin and 100 μg/mL of Streptomycin) with IL-7 (10 ng/mL; PeproTech) and IL-15 (5 ng/mL; PeproTech) or IL-2 (50 U/ml; R&D). Four to seven days later, cells were collected for in vitro or in vivo experiments. Lentiviral transduced cells were selected in 1 μg/ml puromycin (Sigma) for 3-5 days before T cells were used in functional assays.

CAR19 expression on T cells was detected with CAR19 anti-idiotype antibody followed by a goat anti-mouse APC secondary Ab (BD bioscience). Murine anti-human CD3, CD4, CD8, CD45, CD69 and CD19 Abs were obtained from BD Bioscience. Samples were acquired on a Canto II or Fortessa flow cytometer from BD and data were analyzed using the FlowJo software (Tree star).

For activation of CD19-specific CAR-T cells with the anti-idiotype Ab or $CD19^{+}$ tumor cells, anti-CAR19 and anti-CD3 Abs were serially diluted 2-fold, and coated on non-tissue culture treated 96-well plates for 16 hours. Plates were washed twice before plating T cells ($2.5\times10^{5}$ cells/well). Plates were centrifuged at 1,000 g for 5 min, and incubated at 37° C. for 6 hours. Plates were then briefly spun, and 200 μl of the supernatant was collected for ELISA. Cells were collected and stained with anti-CAR19, CD4-PE, CD69-FITC Abs and Zombie Aqua™ dye (Biolegend) at 4° C. for 30 min. Samples were fixed and stored for flow cytometry analysis. For tumor cell-mediated activation, $5\times10^{4}$ BV173 tumor cells were seeded in each well of 96-well plates, and T cells were serially diluted and seeded. Six hours later, supernatant was collected for ELISA.

Cytokines in culture supernatants and plasma were measured using enzyme-linked immunosorbent assay (ELISA) or magnetic luminex assay following manufacturer's instructions (R&D Systems). Data were collected and analyzed using the Lumina-200 System and the Bio-Plex Manager 6.1 software (Bio-Rad).

For $Ca^{2+}$ influx assays, T cells were incubated with $Ca^{2+}$ indicator as per manufacturer's instructions ($Ca^{2+}$ influx assay, BD Bioscience). Cells were incubated with anti-CAR19 Ab followed by goat anti-mouse secondary Ab on ice. $Ca^{2+}$ current was measured by flow cytometry for time-lapsed fluorescence change. Cells were first collected on ice as the baseline of the $Ca^{2+}$ current, and then activated at 37° C. for the $Ca^{2+}$ current during T cell activation.

For Immunoprecipitation (IP), assay, proteins from T cells were extracted in RIPA lysis buffer (Thermo Scientific) supplemented with 1×protease/phosphatase Inhibitors (Thermo Scientific). Equal amount of total proteins was used for IP. Rabbit/mouse IgG (Thermo Scientific) with protein G magnetic beads (Bio-Rad) was used to pre-clear the lysate and anti-CAR19, anti-HA or anti-FLAG Abs were incubated with lysate for 16 hours, and protein G beads were then used for the pull-down. IP products were dissolved in 2× SDS Laemmli buffer for Western blot analysis. For mass spectrometry, $>5\times10^{8}$ T cells were lysed and anti-CAR19 Ab was first crosslinked on protein G beads with Dimethyl pimelimidate (DMP, Thermo Scientific). 2× SDS Laemmli buffer without β-mercaptoethanol was used to dissolve the IP product, and β-mercaptoethanol was supplemented before western blot.

For western blot assays, protein lysate was normalized according to the amount of CAR expression and resolved on 4%-15% SDS polyacrylamide gel electrophoresis gels (SDS-PAGE, Bio-Rad). After protein transfer onto Polyvinylidene fluoride membranes (Bio-Rad), membranes were blocked in 5% non-fat milk in TBS-T and incubated with primary and secondary Abs in TBS-T with 1% milk. The following Abs were used: anti-CD3pY83 and anti-CD3pY142 (Abcam), anti-ZAP70pY319, anti-ZAP70, anti-LATpY191, anti-LAT, anti-LCK, anti-THEMIS, anti-SHP1 and anti-HA tag (Cell Signaling Technology), anti-CD3ζ, anti-FKBP, anti-β-actin (Santa Cruz), anti-FLAG (M2) (Sigma) and horseradish peroxidase conjugated secondary Abs (Goat-anti-mouse, Goat-anti-Rabbit from Thermo Scientific). Membranes were developed with SuperSignal West Femto Maximum Sensitivity Substrate (Thermo Scientific) on a Gel station (Bio-Rad).

For mass spectrometry (MS) assays, immunoprecipitated samples (3 biological replicates) were subjected to SDS-PAGE and stained with Coomassie blue dye. Lanes for each sample were excised and the proteins were reduced, alkylated, and in-gel digested with trypsin overnight at 37° C. Peptides were extracted, desalted with C18 spin columns (Pierce) and dried via vacuum centrifugation. Peptide samples were stored at −80° C. until further analysis. The peptide samples were analyzed by liquid chromatography coupled to tandem mass spectrometry (LC-MS/MS) in 3 separated experiments using a Thermo Easy nLC 1000 coupled to a QExactive HF or a Waters nanoAcquity coupled to a Thermo LTQ-Orbitrap Velos. Samples were injected onto a PepMap C18 column (75 μm id×25 cm, 2 μm particle size) (Thermo Scientific) and separated over a 90 or 120 min gradient where mobile phase A was 0.1% formic acid in water and mobile phase B consisted of 0.1% formic acid in ACN. The LTQ-Orbitrap Velos was operated in data-dependent mode where the 10 most abundant precursors were selected for CID fragmentation (35% CE). The QExactive HF was operated in data-dependent mode where the 15 most intense precursors were selected for subsequent HCD fragmentation (27 NCE). For the second replicate, a targeted analysis of THEMIS peptides was conducted. The QExactive HF was operated in PRM mode, and an inclusion list was used to target previously identified THEMIS peptides. Raw data files were processed using Proteome Discoverer version 2.1 (Thermo Scientific). Peak lists were searched against a reviewed Uniprot human database and appended with the CAR-T sequences using Sequest. The following parameters were used to identify tryptic peptides for protein identification: 10 ppm precursor ion mass tolerance; 0.02 Da product ion mass tolerance for QE HF data and 0.6 Da for Velos data; up to two missed trypsin cleavage sites; carbamidomethylation of Cys was set as a fixed modification; oxidation of Met, acetylation of N-terminus and phosphorylation of Ser, Thr and Tyr were set as variable modifications. The ptmRS node was used to localize the sites of phosphorylation. Peptide false discovery rates (FDR) were calculated by the Percolator node using a decoy database search and data were filtered using a 5% FDR cutoff.

Animal studies were performed in accordance with the Institutional Animal Care and Use Committee of UNC. For long-term in vivo cytotoxicity, male or female NSG (NOD-scid $IL2Rg^{null}$) mice were injected intravenously (i.v.) with $2\times10^{6}$ $CD19^{+}$ Daudi tumor cell line labeled with the Firefly luciferase gene (Daudi-FFLuc). Four to seven days later, mice received T cells control or expressing CARs intravenously (i.v.). For tumor re-challenging experiments, $2\times10^{6}$ $CD19^{+}$ Daudi-FFLuc cells were i.v. injected at indicated time point. Tumor growth was monitored every 2-3 days by injecting mice intraperitoneally (i.p.) with D-luciferin (150 mg/kg, Xenolight, PerkinElmer). Photon emission was analyzed using the Xenogen-IVIS Imaging System. For short-term in vivo T cell activation, NSG mice were injected with Daudi-FFLuc cells i.v. Two weeks later, CAR19.28ζ-Ts were labeled with Cell-trace Violet (Thermo Scientific) and CAR19.BBζ-Ts were labeled with CFSE (Thermo Scientific) as per manufacturer's instructions. Cells were mixed 1:1, and a total $1\times10^{7}$ cells were i.v. injected in each mouse. Peripheral blood, bone marrow, lung and spleen were harvested 6 hours after T cell injection, dissociated into single cells and stained with anti-human CD45-PE, CD3-APC and CD69-PE-Cy7 Abs. For the neuroblastoma metastatic model, 6-8-week-old male or female NSG mice were injected i.v. with CHLA-255-FFluc tumor cell line ($2\times10^{6}$ cells/mouse). Fourteen days after tumor inoculation, CAR-T cells were infused i.v. For the NSG mouse model to evaluate the effects of SHP1 heterodimerization in CAR-T cells in vivo, mice were injected i.v. with $2\times10^6$ Daudi-FFLuc cells. Seven days later, $2\times10^6$ T cells were infused i.v. AP21967 was administrated intraperitoneally twice at 10 mg/kg dose. Tumor growth was monitored twice a week.

For the humanized mouse model to evaluate the effects of SHP1 heterodimerization in CAR-T cells in vivo, humanized NSG (NOD-scid IL2Rg$^{null}$) mice (NSG-hu HSC) were generated. Briefly, human fetal liver tissues were obtained from elective or medically indicated termination of pregnancy through a non-profit intermediary working with outpatient clinics (Advanced Bioscience Resources). CD34$^+$ hematopoietic stem cells (HSC) were transplanted in newborn NSG mice through intra-liver injection of $2\times10^5$ purified HSC. Human immune cell engraftment was detected by flow cytometry 12 weeks after transplantation. Standard parameters of evaluation of CRS in humanized NSG mice was performed. Mice were infused with $5\times10^6$ CAR-T cells at day 0, and plasma was collected at days 1 and 2. AP21967 was administrated intraperitoneally at 10 mg/kg dose. Weight of each mouse was normalized to starting weight before CAR-T cell infusion. In a second CRS murine model, 7-10-week-old female C.B-Igh-1b/GbmsTac-Prkdc$^{scid}$-Lyst$^{bg}$N7 (SCID-beige, Taconic Biosciences) mice were injected i.p. with Raji-FFluc cells. After 21 days, mice were grouped based on the BLI (total flux). Mice were infused i.p. with $30\times10^6$ CAR-T cells. Weight of each mouse was normalized to starting weight before CAR-T cell infusion.

detect CAR19 expression. Cells were then fixed and permeabilized with Cytofix/Cytoperm solution (BD Bioscience) according to manufacturer's instructions. Intracellular FLAG-tagged LCK was detected with Rabbit anti-FLAG (Cell Signaling Technology) and goat anti-Rabbit IgG conjugated with AlexaFluor 488 (Invitrogen). Cells were then loaded on slides by Cytospin Cytocentrifuge (Thermo Scientific) and mounted with ProLong Diamond Antifade Mountant with DAPI (Thermo Scientific). Slides were imaged using confocal microscopy (Zeiss LSM710) and images were analyzed with Fiji software (ImageJ).

Data were presented as mean±SEM unless indicated otherwise. Statistical analyses were performed using GraphPad Prism software. Two-tailed unpaired t-test, one-way ANOVA, and two-way ANOVA were used. Bonferroni's correction for multiple comparisons was used to calculate adjusted p value when appropriate. The exact p values were shown in figures; ns, not significant. Specific statistical test used for each figure was described in the corresponding figure legend.

The foregoing examples are illustrative of the present invention, and are not to be construed as limiting thereof. Although the invention has been described in detail with reference to preferred embodiments, variations and modifications exist within the scope and spirit of the invention as described and defined in the following claims.

TABLE 1

Phosphorylation sites identified on CAR19.28ζ-T and CAR19.BBζ-T cells by LC-MS/MS analysis (SEQ ID NOs: 5-11 in descending order).

| Annotated sequence | Phosphoylation site in peptide | Phosphorylation site in protein CAR19.28ζ/CAR19.BBζ (native CD3ζ) | Peak area CAR19.28ζ | Peak area CAR19.BBζ |
|---|---|---|---|---|
| [R].LLHSDYMNMTPR.[R] | T10 | 356 | 2.93E+07 | ND |
| [K].HYQPYAPPR.[D] | Y5 | 370 | 3.74E+06 | ND |
| [R].SADAPAYQQGQNQLYNELNLGR.[R] | S1 | 388/389 | ND | 3.62E+07 |
| [R].SADAPAYQQGQNQLYNELNLGR.[R] | Y15 | 402 (Y72) | 4.60E+07 | ND |
| [R].REEYDVLDKR.[R] | Y4 | 413 (Y83) | ** | ND |
| [K].NPQEGLYNELQK.[D] | Y7 | 440/441(Y111) | 2.01E+07 | ND |
| [K].MAEAYSEIGMK.[G] | Y5 | 452/453 (Y123) | 1.41E+07 | ND |
| [R].GKGHDGLYQGLSTATK.[D] | Y8 | 471 (Y142) | 4.23E+07 | ND |

For co-culture assays, CD19$^+$ BV173 tumor cells were seeded into 24-well plates with $5\times10^5$ cells/well and T cells were added at different effector to target (E:T) ratios (E:T=1:1 or 1:5). After 24 hours, supernatant was collected for ELISA. Three days later, cells were collected and stained with anti-human CD3 and CD19 Abs for flow cytometry analysis.

For immunofluorescence and confocal microscopy, control and CAR19.BBζ-T cells with or without FLAG-tagged LCK at day 6 of culture were first stained with CAR19 anti-idiotype Ab followed by the goat anti-mouse IgG conjugated with AlexaFluor 647 (Invitrogen) secondary Ab to The peptide sequence containing the phosphosite identified is listed, along with the phosphosite within the peptide and protein (CAR19.28ζ and CAR19.BBζ, or corresponding site on native CD3ζ in parentheses). The phosphoRS probability node within Proteome Discoverer 2.1 was used to localize the phosphorylation sites and only phosphopeptides with a phosphoRS probability of 100% were considered. Peak areas for each phosphopeptide were extracted using the peak area node within Proteome Discoverer 2.1. Abbreviations: ND=not detected; **=detected, but peak area could not be extracted.

TABLE 2

Proteomics results for selected proteins in IP samples of CAR19.28ζ-T and CAR19.BBζ-T cells.

| | | CAR19.28ζ | | | | CAR19.BBζ | | | |
|---|---|---|---|---|---|---|---|---|---|
| Accession | Gene symbol | Peptides | Coverage | Area | SC | Peptides | Coverage | Area | SC |
| P06239 | LCK | 12 | 32% | 6.84E+08 | 60 | 13 | 34% | 4.48E+08 | 61 |
| Q8N1K5 | THEMIS | 2 | 3% | 1.89E+07 | 9 | 2 | 4% | 3.78E+07 | 14 |
| P27986 | PIK3R1 | 11 | 17% | 2.30E+08 | 40 | 1 | 2% | 1.51E+07 | 3 |
| O00329 | PIK3CD | 12 | 13% | 1.79E+08 | 39 | 2 | 2% | 5.10E+06 | 2 |
| Q13077 | TRAF1 | — | — | — | — | 4 | 15% | 2.31E+08 | 16 |
| Q12933 | TRAF2 | — | — | — | — | 6 | 14% | 5.52E+07 | 12 |
| P01732 | CD8A | 7 | 32% | 1.59E+08 | 17 | 6 | 32% | 7.34E+08 | 16 |

The number of peptides identified and percent coverage for each protein is averaged across three biological replicates. A peptide false discovery rate of 5% was used to filter all data. Areas and spectral counts (SC) were used as abundance measures. Areas are summed across all biological replicates and were calculated by averaging the peak areas of the top 3 (or less) unique peptides for each protein. SCs were calculated by summing the number of identified peptide spectrum matches for each protein across all biological replicates. Values not identified are denoted by "-".

SEQUENCE LISTING

```
<160> NUMBER OF SEQ ID NOS: 11

<210> SEQ ID NO 1
<211> LENGTH: 95
<212> TYPE: PRT
<213> ORGANISM: Artificial
<220> FEATURE:
<223> OTHER INFORMATION: FRB domain

<400> SEQUENCE: 1

Ser Arg Ile Leu Trp His Glu Met Trp His Glu Gly Leu Glu Glu Ala
1               5                   10                  15

Ser Arg Leu Tyr Phe Gly Glu Arg Asn Val Lys Gly Met Phe Glu Val
            20                  25                  30

Leu Glu Pro Leu His Ala Met Met Glu Arg Gly Pro Gln Thr Leu Lys
        35                  40                  45

Glu Thr Ser Phe Asn Gln Ala Tyr Gly Arg Asp Leu Met Glu Ala Gln
    50                  55                  60

Glu Trp Cys Arg Lys Tyr Met Lys Ser Gly Asn Val Lys Asp Leu Leu
65                  70                  75                  80

Gln Ala Trp Asp Leu Tyr Tyr His Val Phe Arg Arg Ile Ser Lys
                85                  90                  95


<210> SEQ ID NO 2
<211> LENGTH: 110
<212> TYPE: PRT
<213> ORGANISM: Artificial
<220> FEATURE:
<223> OTHER INFORMATION: FKBP domain

<400> SEQUENCE: 2

Met Leu Glu Gly Val Gln Val Glu Thr Ile Ser Pro Gly Asp Gly Arg
1               5                   10                  15

Thr Phe Pro Lys Arg Gly Gln Thr Cys Val Val His Tyr Thr Gly Met
            20                  25                  30

Leu Glu Asp Gly Lys Lys Val Asp Ser Ser Arg Asp Arg Asn Lys Pro
        35                  40                  45

Phe Lys Phe Met Leu Gly Lys Gln Glu Val Ile Arg Gly Trp Glu Glu
    50                  55                  60

Gly Val Ala Gln Met Ser Val Gly Gln Arg Ala Lys Leu Thr Ile Ser
65                  70                  75                  80
```

```
Pro Asp Tyr Ala Tyr Gly Ala Thr Gly His Pro Gly Ile Ile Pro Pro
                85                  90                  95

His Ala Thr Leu Val Phe Asp Val Glu Leu Leu Lys Leu Glu
            100                 105                 110


<210> SEQ ID NO 3
<211> LENGTH: 599
<212> TYPE: PRT
<213> ORGANISM: Artificial
<220> FEATURE:
<223> OTHER INFORMATION: Chimeric antigen receptor sequence

<400> SEQUENCE: 3

Met Glu Phe Gly Leu Ser Trp Leu Phe Leu Val Ala Ile Leu Lys Gly
1               5                   10                  15

Val Gln Cys Ser Arg Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Leu Lys
        115                 120                 125

Arg Gly Gly Gly Gly Ser Gly Gly Gly Gly Ser Gly Gly Gly Gly Ser
    130                 135                 140

Gly Gly Gly Gly Ser Glu Val Gln Leu Gln Gln Ser Gly Pro Gly Leu
145                 150                 155                 160

Val Ala Pro Ser Gln Ser Leu Ser Val Thr Cys Thr Val Ser Gly Val
                165                 170                 175

Ser Leu Pro Asp Tyr Gly Val Ser Trp Ile Arg Gln Pro Pro Arg Lys
            180                 185                 190

Gly Leu Glu Trp Leu Gly Val Ile Trp Gly Ser Glu Thr Thr Tyr Tyr
        195                 200                 205

Asn Ser Ala Leu Lys Ser Arg Leu Thr Ile Ile Lys Asp Asn Ser Lys
    210                 215                 220

Ser Gln Val Phe Leu Lys Met Asn Ser Leu Gln Thr Asp Asp Thr Ala
225                 230                 235                 240

Ile Tyr Tyr Cys Ala Lys His Tyr Tyr Tyr Gly Gly Ser Tyr Ala Met
                245                 250                 255

Asp Tyr Trp Gly Gln Gly Thr Ser Val Thr Val Ser Ser Thr Arg Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335
```

```
Thr Leu Tyr Cys Arg Ser Lys Arg Ser Arg Leu Leu His Ser Asp Tyr
            340                 345                 350

Met Asn Met Thr Pro Arg Arg Pro Gly Pro Thr Arg Lys His Tyr Gln
        355                 360                 365

Pro Tyr Ala Pro Pro Arg Asp Phe Ala Ala Tyr Arg Ser Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg Ser Gly Gly
                485                 490                 495

Gly Ser Ile Leu Trp His Glu Met Trp His Glu Gly Leu Glu Glu Ala
            500                 505                 510

Ser Arg Leu Tyr Phe Gly Glu Arg Asn Val Lys Gly Met Phe Glu Val
        515                 520                 525

Leu Glu Pro Leu His Ala Met Met Glu Arg Gly Pro Gln Thr Leu Lys
    530                 535                 540

Glu Thr Ser Phe Asn Gln Ala Tyr Gly Arg Asp Leu Met Glu Ala Gln
545                 550                 555                 560

Glu Trp Cys Arg Lys Tyr Met Lys Ser Gly Asn Val Lys Asp Leu Leu
                565                 570                 575

Gln Ala Trp Asp Leu Tyr Tyr His Val Phe Arg Arg Ile Ser Lys Asp
            580                 585                 590

Tyr Lys Asp Asp Asp Asp Lys
        595
```

<210> SEQ ID NO 4
<211> LENGTH: 714
<212> TYPE: PRT
<213> ORGANISM: Artificial
<220> FEATURE:
<223> OTHER INFORMATION: FKBP-SHP1 construct

<400> SEQUENCE: 4

```
Met Leu Glu Gly Val Gln Val Glu Thr Ile Ser Pro Gly Asp Gly Arg
1               5                   10                  15

Thr Phe Pro Lys Arg Gly Gln Thr Cys Val Val His Tyr Thr Gly Met
            20                  25                  30

Leu Glu Asp Gly Lys Lys Val Asp Ser Ser Arg Asp Arg Asn Lys Pro
        35                  40                  45

Phe Lys Phe Met Leu Gly Lys Gln Glu Val Ile Arg Gly Trp Glu Glu
    50                  55                  60

Gly Val Ala Gln Met Ser Val Gly Gln Arg Ala Lys Leu Thr Ile Ser
65                  70                  75                  80

Pro Asp Tyr Ala Tyr Gly Ala Thr Gly His Pro Gly Ile Ile Pro Pro
                85                  90                  95
```

```
His Ala Thr Leu Val Phe Asp Val Glu Leu Leu Lys Leu Glu Ser Gly
            100                 105                 110

Gly Gly Ser Gly Val Asp Leu Ser Arg Gly Trp Phe His Arg Asp Leu
        115                 120                 125

Ser Gly Leu Asp Ala Glu Thr Leu Leu Lys Gly Arg Gly Val His Gly
    130                 135                 140

Ser Phe Leu Ala Arg Pro Ser Arg Lys Asn Gln Gly Asp Phe Ser Leu
145                 150                 155                 160

Ser Val Arg Val Gly Asp Gln Val Thr His Ile Arg Ile Gln Asn Ser
                165                 170                 175

Gly Asp Phe Tyr Asp Leu Tyr Gly Gly Glu Lys Phe Ala Thr Leu Thr
            180                 185                 190

Glu Leu Val Glu Tyr Tyr Thr Gln Gln Gln Gly Val Leu Gln Asp Arg
        195                 200                 205

Asp Gly Thr Ile Ile His Leu Lys Tyr Pro Leu Asn Cys Ser Asp Pro
    210                 215                 220

Thr Ser Glu Arg Trp Tyr His Gly His Met Ser Gly Gly Gln Ala Glu
225                 230                 235                 240

Thr Leu Leu Gln Ala Lys Gly Glu Pro Trp Thr Phe Leu Val Arg Glu
                245                 250                 255

Ser Leu Ser Gln Pro Gly Asp Phe Val Leu Ser Val Leu Ser Asp Gln
            260                 265                 270

Pro Lys Ala Gly Pro Gly Ser Pro Leu Arg Val Thr His Ile Lys Val
        275                 280                 285

Met Cys Glu Gly Gly Arg Tyr Thr Val Gly Gly Leu Glu Thr Phe Asp
    290                 295                 300

Ser Leu Thr Asp Leu Val Glu His Phe Lys Lys Thr Gly Ile Glu Glu
305                 310                 315                 320

Ala Ser Gly Ala Phe Val Tyr Leu Arg Gln Pro Tyr Tyr Ala Thr Arg
                325                 330                 335

Val Asn Ala Ala Asp Ile Glu Asn Arg Val Leu Glu Leu Asn Lys Lys
            340                 345                 350

Gln Glu Ser Glu Asp Thr Ala Lys Ala Gly Phe Trp Glu Glu Phe Glu
        355                 360                 365

Ser Leu Gln Lys Gln Glu Val Lys Asn Leu His Gln Arg Leu Glu Gly
    370                 375                 380

Gln Arg Pro Glu Asn Lys Gly Lys Asn Arg Tyr Lys Asn Ile Leu Pro
385                 390                 395                 400

Phe Asp His Ser Arg Val Ile Leu Gln Gly Arg Asp Ser Asn Ile Pro
                405                 410                 415

Gly Ser Asp Tyr Ile Asn Ala Asn Tyr Ile Lys Asn Gln Leu Leu Gly
            420                 425                 430

Pro Asp Glu Asn Ala Lys Thr Tyr Ile Ala Ser Gln Gly Cys Leu Glu
        435                 440                 445

Ala Thr Val Asn Asp Phe Trp Gln Met Ala Trp Gln Glu Asn Ser Arg
    450                 455                 460

Val Ile Val Met Thr Thr Arg Glu Val Glu Lys Gly Arg Asn Lys Cys
465                 470                 475                 480

Val Pro Tyr Trp Pro Glu Val Gly Met Gln Arg Ala Tyr Gly Pro Tyr
                485                 490                 495

Ser Val Thr Asn Cys Gly Glu His Asp Thr Thr Glu Tyr Lys Leu Arg
            500                 505                 510
```

```
Thr Leu Gln Val Ser Pro Leu Asp Asn Gly Asp Leu Ile Arg Glu Ile
        515                 520                 525

Trp His Tyr Gln Tyr Leu Ser Trp Pro Asp His Gly Val Pro Ser Glu
    530                 535                 540

Pro Gly Gly Val Leu Ser Phe Leu Asp Gln Ile Asn Gln Arg Gln Glu
545                 550                 555                 560

Ser Leu Pro His Ala Gly Pro Ile Ile Val His Cys Ser Ala Gly Ile
                565                 570                 575

Gly Arg Thr Gly Thr Ile Ile Val Ile Asp Met Leu Met Glu Asn Ile
            580                 585                 590

Ser Thr Lys Gly Leu Asp Cys Asp Ile Asp Ile Gln Lys Thr Ile Gln
        595                 600                 605

Met Val Arg Ala Gln Arg Ser Gly Met Val Gln Thr Glu Ala Gln Tyr
    610                 615                 620

Lys Phe Ile Tyr Val Ala Ile Ala Gln Phe Ile Glu Thr Thr Lys Lys
625                 630                 635                 640

Lys Leu Glu Val Leu Gln Ser Gln Lys Gly Gln Glu Ser Glu Tyr Gly
                645                 650                 655

Asn Ile Thr Tyr Pro Pro Ala Met Lys Asn Ala His Ala Lys Ala Ser
            660                 665                 670

Arg Thr Ser Ser Lys His Lys Glu Asp Val Tyr Glu Asn Leu His Thr
        675                 680                 685

Lys Asn Lys Arg Glu Glu Lys Val Lys Lys Gln Arg Ser Ala Asp Lys
    690                 695                 700

Glu Lys Ser Lys Gly Ser Leu Lys Arg Lys
705                 710


<210> SEQ ID NO 5
<211> LENGTH: 12
<212> TYPE: PRT
<213> ORGANISM: Artificial
<220> FEATURE:
<223> OTHER INFORMATION: peptide sequence containing phosphosite

<400> SEQUENCE: 5

Leu Leu His Ser Asp Tyr Met Asn Met Thr Pro Arg
1               5                   10


<210> SEQ ID NO 6
<211> LENGTH: 9
<212> TYPE: PRT
<213> ORGANISM: Artificial
<220> FEATURE:
<223> OTHER INFORMATION: peptide sequence containing phosphosite

<400> SEQUENCE: 6

His Tyr Gln Pro Tyr Ala Pro Pro Arg
1               5


<210> SEQ ID NO 7
<211> LENGTH: 22
<212> TYPE: PRT
<213> ORGANISM: Artificial
<220> FEATURE:
<223> OTHER INFORMATION: peptide sequence containing phosphosite

<400> SEQUENCE: 7

Ser Ala Asp Ala Pro Ala Tyr Gln Gln Gly Gln Asn Gln Leu Tyr Asn
1               5                   10                  15

Glu Leu Asn Leu Gly Arg
```

-continued

```
           20


<210> SEQ ID NO 8
<211> LENGTH: 10
<212> TYPE: PRT
<213> ORGANISM: Artificial
<220> FEATURE:
<223> OTHER INFORMATION: peptide sequence containing phosphosite

<400> SEQUENCE: 8

Arg Glu Glu Tyr Asp Val Leu Asp Lys Arg
1               5                   10


<210> SEQ ID NO 9
<211> LENGTH: 12
<212> TYPE: PRT
<213> ORGANISM: Artificial
<220> FEATURE:
<223> OTHER INFORMATION: peptide sequence containing phosphosite

<400> SEQUENCE: 9

Asn Pro Gln Glu Gly Leu Tyr Asn Glu Leu Gln Lys
1               5                   10


<210> SEQ ID NO 10
<211> LENGTH: 11
<212> TYPE: PRT
<213> ORGANISM: Artificial
<220> FEATURE:
<223> OTHER INFORMATION: peptide sequence containing phosphosite

<400> SEQUENCE: 10

Met Ala Glu Ala Tyr Ser Glu Ile Gly Met Lys
1               5                   10


<210> SEQ ID NO 11
<211> LENGTH: 16
<212> TYPE: PRT
<213> ORGANISM: Artificial
<220> FEATURE:
<223> OTHER INFORMATION: peptide sequence containing phosphosite

<400> SEQUENCE: 11

Gly Lys Gly His Asp Gly Leu Tyr Gln Gly Leu Ser Thr Ala Thr Lys
1               5                   10                  15
```

That which is claimed is:

1. A method of reducing a T cell-mediated immune stimulation to a target cell population or tissue in a subject, comprising:

a) administering to the subject an effective amount of a T cell comprising a vector, wherein the vector comprises a first nucleic acid molecule encoding a chimeric antigen receptor (CAR) and a second nucleic acid molecule encoding a polypeptide comprising an FKBP linked to SHP1, wherein the CAR comprises a hinge region, a transmembrane domain, a CD3ζ domain, an scFv, a CD28 costimulatory molecule, and an FKBP-rapamycin binding domain (FRB), wherein the scFv binds to TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-β, SSEA-4, CD20, FRα, ERBB2(Her2/neu), MUC1, EGFR, NCAM, Prostase, PAP, ELF2M, EphB2, IGF-I receptor, CAIX, LMP2, gp100, bcr-abl, tyrosinase, EphA2, GM1, sLe, GM3, TGSS, HMWMAA, FRβ, TEM1/CD248, TEM7R, CLDN6, GPRCSD, CXORF61, CD97, CD179a, ALK, PSA, PLAC1, GloboH, NY-BR-1, UPK2, HAVCR1, ADRB3, PANX3, GPR20, LY6K, OR51E2, TARP, WT1, NY-ESO-1, LAGE-1a, MAGE-AL legumain, HPV E6, E7, MAGE A1, ETV6-AML, Sp17, XAGE1, Tie 2, MAD-CT-1, MAD-CT-2, FRA1, p53, p53 mutants, prostein, survivin, PCTA-1/Galectin8, MelanA/MART1, Ras, hTERT, ML-IAP, ER, TMPRSS2 ETS fusion gene, NA17, PAX3, AR, cyclin B1, MYCN, RhoC, TRP-2, CYP1B1, BORIS, SART3, PAX5, OY-TES1, LCK, AKAP-4, SSX2, RAGE-1, RU1, RU2, CEA, hsp70-2, CD79a, CD79b, CD72, LAIR1, FCAR, LILRA2, CD300LF, CLEC12A, BST2, EMR2, LY75, GPC3, CLN18.2, CLN6, FCRL5, IGLL1, or any variant thereof; and b) administering an effective amount of AP21967 and/or functional analogue thereof, wherein the AP21967 and/or functional analogue thereof dimerizes the CAR and the polypeptide, thereby reducing the T cell-mediated immune stimulation.

2. The method of claim 1, wherein the transmembrane domain of the CAR comprises a CD8, CD28, or CD4 transmembrane domain, and/or wherein the FRB domain is linked to the CD3ζ domain.

3. The method of claim 1, wherein the CAR comprises the amino acid sequence:

```
(SEQ ID NO: 3)
MEFGLSWLFLVAILKGVQCSRDIQMTQTTSSLSASLGDRVTISCR
ASQDISKYLNWYQQKPDGTVKLLIYHTSRLHSGVPSRFSGSGSGT
DYSLTISNLEQEDIATYFCQQGNTLPYTFGGGTKLELKRGGGGSG
GGGSGGGGSGGGGSEVQLQQSGPGLVAPSQSLSVTCTVSGVSLPD
YGVSWIRQPPRKGLEWLGVIWGSETTYYNSALKSRLTIIKDNSKS
QVFLKMNSLQTDDTAIYYCAKHYYYGGSYAMDYWGQGTSVTVSST
RTTTPAPRPPTPAPTIASQPLSLRPEACRPAAGGAVHTRGLDFAC
DIYIWAPLAGTCGVLLLSLVITLYCRSKRSRLLHSDYMNMTPRRP
GPTRKHYQPYAPPRDFAAYRSRVKFSRSADAPAYQQGQNQLYNEL
NLGRREEYDVLDKRRGRDPEMGGKPRRKNPQEGLYNELQKDKMAE
AYSEIGMKGERRRGKGHDGLYQGLSTATKDTYDALHMQALPPRSG
GGSILWHEMWHEGLEEASRLYFGERNVKGMFEVLEPLHAMMERGP
QTLKETSFNQAYGRDLMEAQEWCRKYMKSGNVKDLLQAWDLYYHV
FRRISKDYKDDDDK.
```

4. The method of claim 1, wherein the polypeptide comprises the amino acid sequence:

```
(SEQ ID NO: 4)
MLEGVQVETISPGDGRTFPKRGQTCVVHYTGMLEDGKKVDSSRDR
NKPFKFMLGKQEVIRGWEEGVAQMSVGQRAKLTISPDYAYGATGH
PGIIPPHATLVFDVELLKLESGGGSGVDLSRGWFHRDLSGLDAET
LLKGRGVHGSFLARPSRKNQGDFSLSVRVGDQVTHIRIQNSGDFY
DLYGGEKFATLTELVEYYTQQQGVLQDRDGTIIHLKYPLNCSDPT
SERWYHGHMSGGQAETLLQAKGEPWTFLVRESLSQPGDFVLSVLS
DQPKAGPGSPLRVTHIKVMCEGGRYTVGGLETFDSLTDLVEHFKK
TGIEEASGAFVYLRQPYYATRVNAADIENRVLELNKKQESEDTAK
AGFWEEFESLQKQEVKNLHQRLEGQRPENKGKNRYKNILPFDHSR
VILQGRDSNIPGSDYINANYIKNQLLGPDENAKTYIASQGCLEAT
VNDFWQMAWQENSRVIVMTTREVEKGRNKCVPYWPEVGMQRAYGP
YSVTNCGEHDTTEYKLRTLQVSPLDNGDLIREIWHYQYLSWPDHG
VPSEPGGVLSFLDQINQRQESLPHAGPIIVHCSAGIGRTGTIIVI
DMLMENISTKGLDCDIDIQKTIQMVRAQRSGMVQTEAQYKFIYVA
IAQFIETTKKKLEVLQSQKGQESEYGNITYPPAMKNAHAKASRTS
SKHKEDVYENLHTKNKREEKVKKQRSADKEKSKGSLKRK.
```

5. A method of reducing CAR T cell-mediated immune stimulation bystander cytotoxicity in a subject having cancer, comprising:

a) administering to the subject an effective amount of a T cell comprising a vector, wherein the vector comprises a first nucleic acid molecule encoding a chimeric antigen receptor (CAR) and a second nucleic acid molecule encoding a polypeptide comprising an FKBP linked to SHP1, wherein the CAR comprises a hinge region, a transmembrane domain, a CD3ζ domain, an scFv, a CD28 costimulatory molecule, and an FKBP-rapamycin binding domain (FRB), wherein the scFv binds to TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-β, SSEA-4, CD20, FRα, ERBB2(Her2/neu), MUC1, EGFR, NCAM, Prostase, PAP, ELF2M, EphB2, IGF-I receptor, CAIX, LMP2, gp100, bcr-abl, tyrosinase, EphA2, GM1, sLe, GM3, TGS5, HMWMAA, FRβ, TEM1/CD248, TEM7R, CLDN6, GPRC5D, CXORF61, CD97, CD179a, ALK, PSA, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6,E7, MAGE A1, ETV6-AML, Sp17, XAGE1, Tie 2, MAD-CT-1, MAD-CT-2, FRA1, p53, p53 mutants, prostein, survivin, PCTA-1/Galectin8, MelanA/MART1, Ras, hTERT, ML-IAP, ER, TMPRSS2 ETS fusion gene, NA17, PAX3, AR, cyclin B1, MYCN, RhoC, TRP-2, CYP1B1, BORIS, SART3, PAX5, OY-TES1, LCK, AKAP-4, SSX2, RAGE-1, RU1, RU2, CEA, hsp70-2, CD79a, CD79b, CD72, LAIR1, FCAR, LILRA2, CD300LF, CLEC12A, BST2, EMR2, LY75, GPC3, CLN18.2, CLN6, FCRL5, IGLL1, or any variant thereof; and b) administering an effective amount of AP21967 and/or functional analogue thereof, wherein the AP21967 and/or functional analogue thereof dimerizes the CAR and the polypeptide, thereby reducing the CAR T cell-mediated immune stimulation and bystander cytotoxicity.

6. The method of claim 5, wherein the transmembrane domain of the CAR comprises a CD8, CD28, or CD4 transmembrane domain, and/or wherein the FRB domain is linked to the CD3ζ domain.

7. The method of claim 5, wherein the CAR comprises the amino acid sequence:

```
(SEQ ID NO: 3)
MEFGLSWLFLVAILKGVQCSRDIQMTQTTSSLSASLGDRVTISCRASQD
ISKYLNWYQQKPDGTVKLLIYHTSRLHSGVPSRFSGSGSGTDYSLTISN
LEQEDIATYFCQQGNTLPYTFGGGTKLELKRGGGGSGGGGSGGGGSGGG
GSEVQLQQSGPGLVAPSQSLSVTCTVSGVSLPDYGVSWIRQPPRKGLEW
LGVIWGSETTYYNSALKSRLTIIKDNSKSQVFLKMNSLQTDDTAIYYCA
KHYYYGGSYAMDYWGQGTSVTVSSTRTTTPAPRPPTPAPTIASQPLSLR
PEACRPAAGGAVHTRGLDFACDIYIWAPLAGTCGVLLLSLVITLYCRSK
RSRLLHSDYMNMTPRRPGPTRKHYQPYAPPRDFAAYRSRVKFSRSADAP
```

-continued

```
AYQQGQNQLYNELNLGRREEYDVLDKRRGRDPEMGGKPRRKNPQEGLYN
ELQKDKMAEAYSEIGMKGERRRGKGHDGLYQGLSTATKDTYDALHMQAL
PPRSGGGSILWHEMWHEGLEEASRLYFGERNVKGMFEVLEPLHAMMERG
PQTLKETSFNQAYGRDLMEAQEWCRKYMKSGNVKDLLQAWDLYYHVFRR
ISKDYKDDDDK.
```

8. The method of claim 5, wherein the polypeptide comprises the amino acid sequence:

```
(SEQ ID NO: 4)
MLEGVQVETISPGDGRTFPKRGQTCVVHYTGMLEDGKKVDSSRDRNKPF
KFMLGKQEVIRGWEEGVAQMSVGQRAKLTISPDYAYGATGHPGIIPPHA
TLVFDVELLKLESGGGSGVDLSRGWFHRDLSGLDAETLLKGRGVHGSFL
ARPSRKNQGDFSLSVRVGDQVTHIRIQNSGDFYDLYGGEKFATLTELVE
YYTQQQGVLQDRDGTIIHLKYPLNCSDPTSERWYHGHMSGGQAETLLQA
KGEPWTFLVRESLSQPGDFVLSVLSDQPKAGPGSPLRVTHIKVMCEGGR
YTVGGLETFDSLTDLVEHFKKTGIEEASGAFVYLRQPYYATRVNAADIE
NRVLELNKKQESEDTAKAGFWEEFESLQKQEVKNLHQRLEGQRPENKGK
NRYKNILPFDHSRVILQGRDSNIPGSDYINANYIKNQLLGPDENAKTYI
ASQGCLEATVNDFWQMAWQENSRVIVMTTREVEKGRNKCVPYWPEVGMQ
RAYGPYSVTNCGEHDTTEYKLRTLQVSPLDNGDLIREIWHYQYLSWPDH
GVPSEPGGVLSFLDQINQRQESLPHAGPIIVHCSAGIGRTGTIIVIDML
MENISTKGLDCDIDIQKTIQMVRAQRSGMVQTEAQYKFIYVAIAQFIET
TKKKLEVLQSQKGQESEYGNITYPPAMKNAHAKASRTSSKHKEDVYENL
HTKNKREEKVKKQRSADKEKSKGSLKRK.
```

9. A method of treating a CD19-expressing cancer in a subject in need thereof, comprising:

a) administering to the subject an effective amount of a T cell comprising a vector, wherein the vector comprises a first nucleic acid molecule encoding a chimeric antigen receptor (CAR) and a second nucleic acid molecule encoding a polypeptide comprising an FKBP linked to SHP1, wherein the CAR comprises a hinge region, a transmembrane domain, a CD35 domain, an scFv, a CD28 costimulatory molecule, and an FKBP-rapamycin binding domain (FRB), wherein the scFv binds to CD19 or any variant thereof; and b) administering an effective amount of AP21967 and/or functional analogue thereof, wherein the AP21967 and/or functional analogue thereof dimerizes the CAR and the polypeptide, thereby treating the subject having a CD19-expressing cancer.

10. The method of claim 9, wherein the transmembrane domain of the CAR comprises a CD8, CD28, or CD4 transmembrane domain, and/or wherein the FRB domain is linked to the CD3ζ domain.

11. The method of claim 9, wherein the CAR comprises the amino acid sequence:

```
(SEQ ID NO: 3)
MEFGLSWLFLVAILKGVQCSRDIQMTQTTSSLSASLGDRVTISCRASQD
ISKYLNWYQQKPDGTVKLLIYHTSRLHSGVPSRFSGSGSGTDYSLTISN
LEQEDIATYFCQQGNTLPYTFGGGTKLELKRGGGGSGGGGSGGGGSGGG
GSEVQLQQSGPGLVAPSQSLSVTCTVSGVSLPDYGVSWIRQPPRKGLEW
LGVIWGSETTYYNSALKSRLTIIKDNSKSQVFLKMNSLQTDDTAIYYCA
KHYYYGGSYAMDYWGQGTSVTVSSTRTTTPAPRPPTPAPTIASQPLSLR
PEACRPAAGGAVHTRGLDFACDIYIWAPLAGTCGVLLLSLVITLYCRSK
RSRLLHSDYMNMTPRRPGPTRKHYQPYAPPRDFAAYRSRVKFSRSADAP
AYQQGQNQLYNELNLGRREEYDVLDKRRGRDPEMGGKPRRKNPQEGLYN
ELQKDKMAEAYSEIGMKGERRRGKGHDGLYQGLSTATKDTYDALHMQAL
PPRSGGGSILWHEMWHEGLEEASRLYFGERNVKGMFEVLEPLHAMMERG
PQTLKETSFNQAYGRDLMEAQEWCRKYMKSGNVKDLLQAWDLYYHVFRR
ISKDYKDDDDK.
```

12. The method of claim 9, wherein the polypeptide comprises the amino acid sequence:

```
(SEQ ID NO: 4)
MLEGVQVETISPGDGRTFPKRGQTCVVHYTGMLEDGKKVDSSRDRNKPF
KFMLGKQEVIRGWEEGVAQMSVGQRAKLTISPDYAYGATGHPGIIPPHA
TLVFDVELLKLESGGGSGVDLSRGWFHRDLSGLDAETLLKGRGVHGSFL
ARPSRKNQGDFSLSVRVGDQVTHIRIQNSGDFYDLYGGEKFATLTELVE
YYTQQQGVLQDRDGTIIHLKYPLNCSDPTSERWYHGHMSGGQAETLLQA
KGEPWTFLVRESLSQPGDFVLSVLSDQPKAGPGSPLRVTHIKVMCEGGR
YTVGGLETFDSLTDLVEHFKKTGIEEASGAFVYLRQPYYATRVNAADIE
NRVLELNKKQESEDTAKAGFWEEFESLQKQEVKNLHQRLEGQRPENKGK
NRYKNILPFDHSRVILQGRDSNIPGSDYINANYIKNQLLGPDENAKTYI
ASQGCLEATVNDFWQMAWQENSRVIVMTTREVEKGRNKCVPYWPEVGMQ
RAYGPYSVTNCGEHDTTEYKLRTLQVSPLDNGDLIREIWHYQYLSWPDH
GVPSEPGGVLSFLDQINQRQESLPHAGPIIVHCSAGIGRTGTIIVIDML
MENISTKGLDCDIDIQKTIQMVRAQRSGMVQTEAQYKFIYVAIAQFIET
TKKKLEVLQSQKGQESEYGNITYPPAMKNAHAKASRTSSKHKEDVYENL
HTKNKREEKVKKQRSADKEKSKGSLKRK.
```

* * * * *